(12) United States Patent
Randolph et al.

(10) Patent No.: US 8,808,710 B2
(45) Date of Patent: *Aug. 19, 2014

(54) METHOD OF PREPARING AN IMMUNOLOGICALLY-ACTIVE ADJUVANT-BOUND DRIED VACCINE COMPOSITION

(71) Applicant: The Regents of the University of Colorado, Denver, CO (US)

(72) Inventors: Theodore Randolph, Niwot, CO (US); Amber Clausi, Easton, PA (US); John F Carpenter, Littleton, CO (US); Daniel K. Schwartz, Boulder, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/898,249

(22) Filed: May 20, 2013

(65) Prior Publication Data

US 2013/0315966 A1 Nov. 28, 2013

Related U.S. Application Data

(63) Continuation of application No. 12/532,225, filed as application No. PCT/US2008/057355 on Mar. 18, 2008, now Pat. No. 8,444,991.

(60) Provisional application No. 60/896,429, filed on Mar. 22, 2007.

(51) Int. Cl.
*A61K 39/02* (2006.01)
*A61K 39/00* (2006.01)
*A61K 45/00* (2006.01)

(52) U.S. Cl.
USPC ............. 424/234.1; 424/184.1; 424/239.1; 424/278.1; 424/489; 426/384

(58) Field of Classification Search
USPC ............. 424/184.1, 234.1, 239.1, 278.1, 489; 34/284, 288; 426/384
See application file for complete search history.

*Primary Examiner* — Rodney P Swartz
(74) *Attorney, Agent, or Firm* — Lewis Kohn & Fitzwilliam LLP; David M. Kohn; Kari Moyer-Henry

(57) ABSTRACT

The disclosure provides a method of preparing an immunologically-active adjuvant-bound freeze dried vaccine composition. A specific embodiment provides a stable vaccine composition comprising an aluminum-salt adjuvant, a recombinant *Clostridium botulinum* neurotoxin protein and a glass-forming agent. These vaccine compositions are useful in the treatment of humans and other animals at risk of infection from *Clostridium botulinum* neurotoxin.

16 Claims, 33 Drawing Sheets

BotNE Sequence:

```
       1          11         21         31         41         51
       |          |          |          |          |          |
  1  MGESQQELNS MVTDTLNNSI PFKLSSYTDD KILISYFNKF FKRIKSSSVL
NMRYKNDKYV    60
 61  DTSGYDSNIN INGDVYKYPT NKNQFGIYND KLSEVNISQN DYIIYDNKYK
NFSISFWVRI   120
121  PNYDNKIVNV NNEYTIINCM RDNNSGWKVS LNHNEIIWTL QDNAGINQKL
AFNYGNANGI   180
181  SDYINKWIFV TITNDRLGDS KLYINGNLID QKSILNLGNI HVSDNILFKI
VNCSYTRYIG   240
241  IRYFNIFDKE LDETEIQTLY SNEPNTNILK DFWGNYLLYD KEYYLLNVLK
PNNFIDRRKD   300
301  STLSINNIRS TILLANRLYS GIKVKIQRVN NSSTNDNLVR KNDQVYINFV
ASKTHLFPLY   360
361  ADTATTNKEK TIKISSSGNR FNQVVVMNSV GNNCTMNFKN NNGNNIGLLG
FKADTVVAST   420
421  WYYTHMRDHT NSNGCFWNFI SEEHGWQEK
```

SEQ ID NO: 1

BotNC Sequence:

```
       1          11         21         31         41         51
       |          |          |          |          |          |
  1  MTIPFNIFSY TNNSLLKDII NEYFNNINDS KILSLQNRKN TLVDTSGYNA
EVSEEGDVQL    60
 61  NPIFPFDFKL GSSGEDRGKV IVTQNENIVY NSMYESFSIS FWIRINKWVS
NLPGYTIIDS   120
121  VKNNSGWSIG IISNFLVFTL KQNEDSEQSI NFSYDISNNA PGYNKWFFVT
VTNNMMGNMK   180
181  IYINGKLIDT IKVKELTGIN FSKTITFEIN KIPDTGLITS DSDNINMWIR
DFYIFAKELD   240
241  GKDINILFNS LQYTNVVKDY WGNDLRYNKE YYMVNIDYLN RYMYANSRQI
VFNTRRNNND   300
301  FNEGYKIIIK RIRGNTNDTR VRGGDILYFD MTINNKAYNL FMKNETMYAD
NHSTEDIYAI   360
361  GLREQTKDIN DNIIFQIQPM NNTYYYASQI FKSNFNGENI SGICSIGTYR
FRLGGDWYRH   420
421  NYLVPTVKQG NYASLLESTS THWGFVPVSE
```

SEQ ID NO: 2

BotNA sequence

```
        1          11         21         31         41         51
        |          |          |          |          |          |
   1  MSTFTEYIKN IINTSILNLR YESNHLIDLS RYASKINIGS KVNFDPIDKN
QIQLFNLESS    60
  61  KIEVILKNAI VYNSMYENFS TSFWIRIPKY FNSISLNNEY TIINCMENNS
GWKVSLNYGE   120
 121  IIWTLQDTQE IKQRVVFKYS QMINISDYIN RWIFVTITNN RLNNSKIYIN
GRLIDQKPIS   180
 181  NLGNIHASNN IMFKLDGCRD THRYIWIKYF NLFDKELNEK EIKDLYDNQS
NSGILKDFWG   240
 241  DYLQYDKPYY MLNLYDPNKY VDVNNVGIRG YMYLKGPRGS VMTTNIYLNS
SLYRGTKFII   300
 301  KKYASGNKDN IVRNNDRVYI NVVVKNKEYR LATNASQAGV EKILSALEIP
DVGNLSQVVV   360
 361  MKSKNDQGIT NKCKMNLQDN NGNDIGFIGF HQFNNIAKLV ASNWYNRQIE
RSSRTLGCSW   420
 421  EFIPVDDGWG ERPL
                                    SEQ ID NO: 3
```

BotNB Sequence

```
        1          11         21         31         41         51
        |          |          |          |          |          |
   1  MANKYNSEIL NNIILNLRYK DNNLIDLSGY GAKVEVYDGV ELNDKNQFKL
TSSANSKIRV    60
  61  TQNQNIIFNS VFLDFSVSFW IRIPKYKNDG IQNYIHNEYT IINCMKNNSG
WKISIRGNRI   120
 121  IWTLIDINGK TKSVFFEYNI REDISEYINR WFFVTITNNL NNAKIYINGK
LESNTDIKDI   180
 181  REVIANGEII FKLDGDIDRT QFIWMKYFSI FNTELSQSNI EERYKIQSYS
EYLKDFWGNP   240
 241  LMYNKEYYMF NAGNKNSYIK LKKDSPVGEI LTRSKYNQNS KYINYRDLYI
GEKFIIRRKS   300
 301  NSQSINDDIV RKEDYIYLDF FNLNQEWRVY TYKYFKKEEE KLFLAPISDS
DELYNTIQIK   360
 361  EYDEQPTYSC QLLFKKDEES TDEIGLIGIH RFYESGIVFE EYKDYFCISK
WYLKEVKRKP   420
 421  YNLKLGCNWQ FIPKDEGWTE
                                    SEQ ID NO: 4
```

FIGURE 32

BotNF Sequence

```
            1          11         21         31         41         51
            |          |          |          |          |          |
     1 MSYTNDKILI LYFNKLYKKI KDNSILDMRY ENNKFIDISC YGSNISINGD VYIYSTNRNQ    60
    61 FGIYSSKPSE VNIAQNNDII YNGRYQNFSM SFWVRIPKYF NKVNLNNEYT IIDCIRNNNS   120
   121 GWKISLNYNK IIWTLQDTAG NNQKLVFNYT QMISISDYIN KWIFVTITNN RLGNSRIYIN   180
   181 GNLIDEKSIS NLGDIHVSDN ILFKIVGCND TRYVGIRYFK VFDTELGKTE IETLYSDEPD   240
   241 PSILKDFWGN YLLYNKRYYL LNLLRTDKSI TQNSNFLNIN QQRGVYQKPN IFSNTRLYTG   300
   301 VEFIIRKNGS TDISNTDNFV RKNDLAYINV VDRDVEYRLN ADISIAKPEK IIKLIRTSNS   360
   361 NNSLGQIIVM DSIGNNCTMN FQNNNGGNIG LLGFHSNNLV ASSWYYNNIR KNTSSNGCFW   420
   421 SFISKEHGWQ EN
```

SEQ ID NO: 5

FIGURE 33

METHOD OF PREPARING AN IMMUNOLOGICALLY-ACTIVE ADJUVANT-BOUND DRIED VACCINE COMPOSITION

CROSS REFERENCES TO RELATED APPLICATIONS

This application is being filed on May 21, 2013, as a continuation of U.S. application Ser. No. 12/532,225, filed Jan. 29, 2010, now issued U.S. Pat. No. 8,444,991, and claims the benefit of priority from International Patent application No. PCT/US08/57355 filed Mar. 18, 2008, which claims the benefit of priority from U.S. Provisional Application No. 60/896,429, filed Mar. 22, 2007, the entire contents of which are incorporated herein by reference.

STATEMENT OF FEDERALLY FUNDED RESEARCH

This invention was partially sponsored by National Institutes of Health (NIH) grant number: HIAID 1 U01 AI056514-01, project Number 1540422 to HTD Biosystems Inc.; 551C Linus Pauling Drive; Hercules, Calif. 94547.

TECHNICAL FIELD

The disclosure provides a method of preparing an immunologically-active adjuvant-bound freeze dried vaccine composition. A specific embodiment provides a vaccine composition comprising an aluminum-salt adjuvant, a recombinant *Clostridium botulinum* neurotoxin protein and a glass-forming agent. These vaccine compositions are useful in the treatment of humans and other animals at risk of infection from *Clostridium botulinum* neurotoxin.

BACKGROUND ART

Vaccines containing recombinant proteins require an adjuvant to elicit an immune response. (Callahan et al., 1991, The importance of surface charge in the optimization of antigen-adjuvant interactions, Pharm. Res. 8(7):851-858). Aluminum-salt adjuvants are currently the most widely used adjuvant for general use in humans.

The mechanisms of action of aluminum-salt adjuvants are poorly understood, but likely due to several different mechanisms. (Lindblad 2004. "Aluminium compounds for use in vaccines" Immunol. Cell. Biol. 82(5):497-505; Gupta and Siber, 1995, Adjuvants for Human Vaccines—Current Status, Problems and Future-Prospects. Vaccine 13(14):1263-1276; Gupta and Rost, 2000, Aluminum Compounds as Vaccine Adjuvants, In O'Hagan D, editor Vaccine Adjuvants: Preparation Methods and Research Protocols, ed., Totowa, N.J.: Humana Press Inc. p 65-89; Cox and Coulter, 1997, Adjuvants—a classification and review of their modes of action, Vaccine 15(3):248-256).

Common proposed mechanisms are that the adjuvant acts as a depot at the site of injection, wherein the antigen is slowly released after administration. (Cox and Coulter, 1997). Another proposed mechanism is that the adjuvant aids in delivery of the antigen to antigen-presenting cells (Lindblad 2004). A further proposed mechanism is that the adjuvant serves as an immunostimulator and elicits Th2 cytokines (Grun and Maurer 1989, Different T helper cell subsets elicited in mice utilizing two different adjuvant vehicles: the role of endogenous interleukin 1 in proliferative responses. Cell Immunol 121(1):134-145). Yet another proposed mechanism is that the adjuvant destabilizes protein antigens on the surface of the adjuvant making them more susceptible to proteolytic degradation (Jones et al., 2005, Effects of adsorption to aluminum salt adjuvants on the structure and stability of model protein antigens. J Biol Chem 280(14):13406-13414; and That et al., 2004. "Antigen stability controls antigen presentation" J. Biol. Chem. 279(48):50257-50266).

Vaccines based on recombinant protein antigens must be formulated with an adjuvant for maximum potency. (Singh and O'Hagan 1999, Advances in vaccine adjuvants, Nat Biotechnol 17(11): 1075-81; and O'Hagan et al., 2001, Recent developments in adjuvants for vaccines against infectious diseases, Biomol Eng 18(3): 69-85). The only adjuvants currently appearing in FDA-approved vaccines are the aluminum salt adjuvants, aluminum hydroxide and aluminum phosphate. It has been suggested that to provide adequate immunogenicity, antigens must be adsorbed on the surface of the adjuvant. (Gupta et al., 1995, Adjuvant Properties of Aluminum and Calcium Compounds. Pharmaceutical Biotechnology. 6: 229-248; and White and Hem, 2000, Characterization of aluminium-containing adjuvants, Dev Biol (Basel) 103: 217-28). This adsorption is typically facilitated through electrostatic interactions between the antigen and adjuvant, and the formulation pH is usually chosen so that the antigen and adjuvant are oppositely charged (Callahan et al. 1991). The surface charge on the adjuvant also can be modified by surface exchange reactions with buffer salts such as phosphate, succinate, and citrate (Hem and White, 1984, Characterization of aluminum hydroxide for use as an adjuvant in parenteral vaccines. J Parenter Sci Technol, 38(1): p. 2-10; Chang et al., 1997, Role of the electrostatic attractive force in the adsorption of proteins by aluminum hydroxide adjuvant. PDA J Pharm Sci Technol, 51(1): p. 25-9; and Rinella et al., 1996, Treatment of aluminium hydroxide adjuvant to optimize the adsorption of basic proteins. Vaccine, 14(4): p. 298-300.)

Although the mechanism of action is not fully understood, it is likely that surface area, surface charge, and morphology of the adjuvant are important factors dictating the immune response to antigens adsorbed onto these adjuvants (Hem and White 1984). It is generally theorized that the smaller the particle size of the vaccine adjuvant, the more immunogenic the vaccine preparation (Maa et al., 2003. Stabilization of alum-adjuvanted vaccine dry powder formulations: mechanism and application. J Pharm Sci 92(2):319-332., Diminsky et al., 1999. Physical, chemical and immunological stability of CHO-derived hepatitis B surface antigen (HBsAg) particles. Vaccine 18(1-2):3-17).

Lyophilization (freeze drying) is a process frequently utilized to improve long term stability of various protein preparations. However, when vaccines formulated with aluminum-salt adjuvants are processed in an attempt to improve stability through freezing and lyophilization, a loss of potency is often reported. Previous studies have suggested that a freeze-dried vaccine product containing an adjuvant cannot be produced due to aggregation of the adjuvant particles. (Diminsky et al., 1999; Maa et al., 2003).

A number of theories were previously set forth to explain possible mechanisms responsible for the loss of potency following lyophilization of vaccines formulated with aluminum-salt adjuvants. For example, the aggregation of aluminum hydroxycarbonate and magnesium hydroxide gels after freezing and thawing has been attributed to ice crystal formation which forces particles together, resulting in irreversible aggregation. (Zapata et al., 1984, Mechanism of freeze-thaw instability of aluminum hydroxycarbonate and magnesium hydroxide gels. J Pharm Sci 73(1):3-8). This explanation has been echoed by Maa et al., 2003 who propose that faster cooling rates result in a greater rate of ice nucleation and the formation of smaller ice crystals, which would not force alum particles into an aggregate. Nygaard et al. showed that the particle diameter, and thus surface area and number of particles, and not mass or volume, is the dominant property in the immunological response of polystyrene particles in mice (Nygaard et al., 2004). Many of these proposed mechanisms have since been shown to be incorrect.

Roser et al., U.S. Pat. No. 6,890,512 disclose a method of preventing aggregation during dehydration and rehydration of particulates in suspension by adding to a particulate suspension of aluminum hydroxide at least 15% (w/v) of trehalose. However, Roser et al. does not discuss freezing rate.

The capacity of particles to increase allergic sensitization is predicted by particle number and surface area, not by particle mass. Toxicol Sci 82(2):515-524). Moorefield et al. showed that the degree of antigen internalization of adjuvant particles is inversely related to the particle size of the adjuvant aggregates (Moorefield et al., 2005. "Role of aluminum-containing adjuvants in antigen internalization by dendritic cells in vitro" Vaccine 23(13):1588-1595). While it is likely that the particle size is an important characteristic parameter for immunogenicity, there has yet to be a comprehensive study examining the particle size distribution (PSD) as a function of formulation and cooling rates along with other physical properties of the products produced.

The genus Clostridium is comprised of gram-positive, anaerobic, spore-forming bacilli. The natural habitat of these organisms is the environment and the intestinal tracts of humans and other animals. Indeed, clostridia are ubiquitous; they are commonly found in soil, dust, sewage, marine sediments, decaying vegetation, and mud. (See e.g., P. H. A. Sneath et al., 1986, "Clostridium," Bergey's Manual® of Systematic Bacteriology, Vol. 2, pp. 1141-1200, Williams & Wilkins). Only a few of the approximately 100 species of Clostridium have been recognized as etiologic agents of medical and veterinary importance. However, these species are associated with very serious diseases, including botulism, tetanus, anaerobic cellulitis, gas gangrene, bacteremia, pseudomembranous colitis, and clostridial gastroenteritis. In most cases, the pathogenicity of these organisms is related to the release of powerful exotoxins or highly destructive enzymes. (Hatheway, 1990, Clin. Microbiol. Rev., 3:66-98).

The botulinum neurotoxin is one of the most poisonous substances known, and hence it has been identified as a potential threat for biological warfare (Gill 1982, Bacterial toxins: a table of lethal amounts, Microbiol Rev 46(1): 86-94; Caya 2001, Clostridium botulinum and the ophthalmologist: a review of botulism, including biological warfare ramifications of botulinum toxin, Surv Ophthalmol 46(1): 25-34). The lethal human dose is $10^{-9}$ mg/kg bodyweight for toxin in the bloodstream. Produced by the bacteria Clostridium botulinum, the neurotoxin exists as seven structurally similar but serologically different variants, identified as A through G (Oguma, et al., 1995, Structure and function of Clostridium botulinum toxins, Microbiol Immunol 39(3): 161-8; Caya 2001). There is little, if any, antibody cross-reactivity between the seven BoNT serotypes A to G. The proteins are comprised of a 100 kDa heavy chain containing binding and internalization domains, and a 50 kDa light chain comprising the catalytic domain, connected by a disulfide bond. Botulinum neurotoxin blocks nerve transmission to the muscles, resulting in flaccid paralysis. When the toxin reaches airway and respiratory muscles, it results in respiratory failure that can cause death. (Amon, 1986, J. Infect. Dis. 154:201-206).

Botulism disease is grouped into four types, based on the method of introduction of toxin into the bloodstream. Foodborne botulism results from ingesting improperly preserved and inadequately heated food that contains botulinal toxin. (MacDonald et al., 1986, Am. J. Epidemiol. 124:79). Wound-induced botulism results from C. botulinum penetrating traumatized tissue and producing toxin that is absorbed into the bloodstream. (Swartz, 1990 "Anaerobic Spore-Forming Bacilli: The Clostridia," pp. 633-646, in B. D. Davis et al., (eds.), Microbiology, 4th edition, J. B. Lippincott Co.). Infectious infant botulism results from C. botulinum colonization of the infant intestine with production of toxin and its absorption into the bloodstream. It is likely that the bacterium gains entry when spores are ingested and subsequently germinate. (Amon 1986). Inhalation botulism results when the toxin is inhaled. Inhalation botulism has been reported as the result of accidental exposure in the laboratory (E. Holzer, Med. Klin. 41:1735 (1962)) and could arise if the toxin is used as an agent of biological warfare (Franz et al., in Botulinum and Tetanus Neurotoxins, B. R. DasGupta, ed., Plenum Press, New York (1993), pp. 473-476).

Different strains of Clostridium botulinum each produce antigenically distinct toxin designated by the letters A-G. Serotype A toxin has been implicated in 26% of the cases of food botulism; types B, E and F have also been implicated in a smaller percentage of the food botulism cases. (Sugiyama 1980, Clostridium botulinum neurotoxin, Microbiol. Rev. 44:419-448). Sequence variation within various C. botulinum neurotoxin serotypes are described in Smith et al. (Smith et al., Sequence variation within Botulinum Neurotoxin Serotypes impacts antibody binding and neutralization. Infection Immun. 2005, 73 (9): 5450-5457).

Currently available protein therapies against these toxins are inadequate because of limited availability, high production costs, and potential side effects (Eubanks et al., 2007, An in vitro and in vivo disconnect uncovered through high-throughput identification of botulinum neurotoxin A antagonists, Proc. Nat. Acad. Sci., 104(8):2602-2607) Immunization of subjects with toxin preparations has been done in an attempt to induce immunity against botulinal toxins. A C. botulinum vaccine comprising chemically inactivated (i.e., formaldehyde-treated) type A, B, C, D and E toxin is commercially available for human usage. However, this vaccine preparation has several disadvantages. First, the efficacy of this vaccine is variable (in particular, only 78% of recipients produce protective levels of anti-type B antibodies following administration of the primary series). Second, immunization is painful (deep subcutaneous inoculation is required for administration), with adverse reactions being common (moderate to severe local reactions occur in approximately 6% of recipients upon initial injection; this number rises to approximately 11% of individuals who receive booster injections) (Informational Brochure for the Pentavalent (ABCDE) Botulinum Toxoid, Centers for Disease Control). Third, preparation of the inactivated vaccine is dangerous as active toxin must be handled by laboratory workers.

Recombinant proteins and peptides derived from the Clostridium botulinum neurotoxin are useful as immunogens for the production of vaccine compositions of the present disclosure. For example, several such recombinant protein sequences, recombinant production techniques and immunological assays are described in U.S. Pat. No. 5,919,665, which is incorporated herein by reference. Recombinant protein antigens for the seven serotypes have been created as part of the development of a heptavalent vaccine against the neurotoxins (Smith 1998, Development of recombinant vaccines for botulinum neurotoxin, Toxicon 36(11): 1539-48; and Smith et al., 2004, Roads from vaccines to therapies, Mov Disord 19 Suppl 8: S48-52). These protein antigens (identified as rBoNTA(Hc)-rBoNTG(Hc)) consist of 50 kDa portions of the C-terminal domain of the heavy chains and have no neurotoxin activity (DePaz et al., 2005, Formulation of Botulinum Neurotoxin Heavy Chain Fragments for Vaccine Development: Mechanisms of Adsorption to an Aluminum-Containing Adjuvant, Vaccine 23: 4029-4035).

Paralysis-inducing neurotoxins produced by the bacterium *Clostridium botulinum* are highly toxic proteins to humans and are classified as category A bioagents by the U.S. government. There is a continuing need to improve vaccine safety and stability without the loss of vaccine immunogenicity. Due to potential bioterrorism threats, there is also an increased need for safe, stable and effective vaccine compositions for administration to those at risk of exposure to *C. botulinum* neurotoxins.

One way to accomplish these goals is to develop methods of production of stable, immunologically-active freeze dried vaccine preparations which may incorporate recombinant antigens.

SUMMARY OF THE DISCLOSURE OF INVENTION

The disclosure provides a method of production of stable, freeze dried vaccine preparations which are immunologically active. The disclosure further provides a method of production of immunologically-active, stable, freeze dried vaccine preparations in which the vaccine antigens are recombinant antigens. The disclosure also provides a stable, immunologically active vaccine composition comprising a recombinant *Clostridium botulinum* neurotoxin protein.

In one embodiment, the disclosure provides a method of preparing an immunologically-active adjuvant-bound dried vaccine composition, the method comprising: combining at least one aluminum-salt adjuvant, at least one buffer system, at least one glass-forming agent, and at least one antigen to create a liquid vaccine formulation; freezing the liquid vaccine formulation to create a frozen vaccine formulation; and lyophilizing the frozen vaccine formulation to create a dried vaccine composition, where the composition is capable of eliciting an immune response in a subject. The immune response developed by the subject may be humoral immunity and/or cell-mediated immunity specific to the antigen. In one aspect, the one or more aluminum-salt adjuvants is selected from the group consisting of aluminum hydroxide, aluminum phosphate and aluminum sulfate. In another aspect, the aluminum-salt adjuvant is aluminum hydroxide. In a further aspect, the one or more buffer systems is selected from the group consisting of acetate, succinate, citrate, prolamine, histidine, borate, carbonate and phosphate buffer systems. In one aspect, the one or more buffer systems is selected from succinate and phosphate buffer systems. In another aspect, the one or more glass-forming agents is selected from the group consisting of trehalose, sucrose, ficoll, dextran, maltotriose, lactose, mannitol, hydroxyethyl starch, glycine, cyclodextrin, povidone, and potassium salts. In a further aspect, the glass-forming agent is trehalose. In one aspect, the glass-forming agent trehalose is present in a weight to volume concentration of from about 5% to about 20% in the liquid vaccine formulation. In another aspect, the glass-forming agent trehalose is present in a weight to volume concentration of from about 7% to about 15% in the liquid vaccine formulation. In a further aspect, the freezing step comprises one of tray freezing, shelf freezing, spray-freezing and shell-freezing. In one aspect, the freezing step comprises spray-freezing.

In one aspect, the antigen is selected from or derived from the group consisting of Rotavirus, Foot and mouth disease virus, influenza A virus, influenza B virus, influenza C virus, H1N1, H2N2, H3N2, H5N1, H7N7, H1N2, H9N2, H7N2, H7N3, H10N7, human parainfluenza type 2, herpes simplex virus, Epstein Barr virus, varicella virus, porcine herpesvirus 1, cytomegalovirus, Lyssavirus, Poliovirus, Hepatitis A, Hepatitis B, Hepatitis C, Hepatitis E, distemper virus, venezuelan equine encephalomyelitis, feline leukemia virus, Reovirus, Respiratory syncytial virus, Lassa fever virus, polyoma tumor virus, canine parvovirus, Papilloma virus, tick borne encephalitis virus, Rinderpest virus, human rhinovirus species, Enterovirus species, Mengo virus, Paramyxovirus, avian infectious bronchitis virus, Human T-cell leukemia-lymphoma virus 1, Human immunodeficiency virus-1, Human immunodeficiency virus-2, lymphocytic choriomeningitis virus, Parovirus B19, Adenovirus, rubella virus, yellow fever virus, dengue virus, Bovine respiratory syncitial virus, Corona virus, *Bordetella pertussis, Bordetella bronchiseptica, Bordetella parapertussis, Brucella abortus, Brucella melitensis, Brucella suis, Brucella ovis, Brucella* species, *Escherichia coli, Salmonella* species, *salmonella typhi*, Streptococci, *Vibrio cholerae, Vibrio parahaemolyticus, Shigella, Pseudomonas*, tuberculosis, avium, Bacille Calmette Guerin, *Micobacterium leprae*, Pneumococci, Staphylococci, *Enterobacter* species, *Rochalimaea henselae, Pasteurella haemolytica, Pasteurella multocida, Chlamydia trachomatis, Chlamydia psittaci, Lymphogranuloma venereum, Treponema pallidum, Haemophilus* species, *Mycoplasma bovigenitalium, Mycoplasma pulmonis, Mycoplasma* species, *Borrelia burgdorferi, Legionella pneumophila, Colstridium botulinum, Corynebacterium diphtheriae, Yersinia entercolitica, Rickettsia rickettsii, Rickettsia typhi, Rickettsia prowazekii, Ehrlichia chaffeensis, Anaplasma phagocytophilum, Plasmodium falciparum, Plasmodium vivax, Plasmodium malariae*, Schistosomes, Trypanosomes, *Leishmania* species, Filarial nematodes, Trichomoniasis, Sarcosporidiosis, *Taenia saginata, Taenia solium, Leishmania, Toxoplasma gondii, Trichinella spiralis*, Coccidiosis, *Eimeria tenella, Cryptococcus neoformans, Candida albicans, Apergillus fumigatus*, Coccidioidomycosis, *Neisseria gonorrhoeae*, Malaria circumsporozoite protein, Malaria merozoite protein, Trypanosome surface antigen protein, Pertussis, Alphaviruses, Adenovirus, Diphtheria toxoid, Tetanus toxoid, meningococcal outer membrane protein, Streptococcal M protein, Influenza hemagglutinin, cancer antigen, tumor antigens, toxins, exotoxins, Neurotoxins, cytokines, cytokine receptors, monokines, monokine receptors, plant pollens, animal dander, and dust mites.

In a specific aspect, the antigen is derived from one or more of *Clostridium botulinum* neurotoxins A, B, C, D, E, F and G. In a further specific aspect, the antigen is recombinant botulinum neurotoxin E (SEQ ID NO: 1). In another specific aspect, the antigen is recombinant botulinum neurotoxin C (SEQ ID NO: 2). In a further specific aspect, the antigen is recombinant botulinum neurotoxin A (SEQ ID NO: 3). In a further specific aspect, the antigen is recombinant botulinum neurotoxin B (SEQ ID NO: 4). In another specific aspect, the antigen is recombinant botulinum neurotoxin F (SEQ ID NO: 5).

In another embodiment, the disclosure provides a freeze dried vaccine composition, the composition comprising: an aluminum-salt adjuvant, a glass-forming agent, a buffer salt, and a recombinant antigen derived from a *Clostridium botulinum* neurotoxin. In one aspect, the aluminum-salt adjuvant in the composition is selected from aluminum hydroxide and aluminum phosphate. In another aspect, the glass-forming agent is trehalose. In a further aspect, the buffer salt is selected from one or more of the group consisting of sodium succinate, potassium succinate, sodium phosphate and potassium phosphate. In a specific aspect, the antigen is recombinant botulinum neurotoxin E (SEQ ID NO: 1). In another specific aspect, the antigen is recombinant botulinum neurotoxin C (SEQ ID NO: 2). In a further specific aspect, the antigen is recombinant botulinum neurotoxin A (SEQ ID NO: 3). In a further specific aspect, the antigen is recombinant botulinum neurotoxin B (SEQ ID NO: 4). In another specific aspect, the antigen is recombinant botulinum neurotoxin F (SEQ ID NO: 5).

In one embodiment, the disclosure provides a method of controlling particle size in an adjuvant-bound dried vaccine composition, the method comprising: combining at least one aluminum-salt adjuvant, at least one buffer system, at least one glass-forming agent, and at least one antigen to create a liquid vaccine formulation; freezing the liquid vaccine formulation to create a frozen vaccine formulation; and lyophilizing the frozen vaccine formulation to create a dried vaccine composition, wherein following dilution of the dried vaccine composition with an aqueous diluent to form a reconstituted vaccine composition the mean particle diameter of the reconstituted vaccine composition is less than 10 micrometers. In another aspect, the one or more aluminum-salt adjuvants is selected from the group consisting of aluminum hydroxide, aluminum phosphate and aluminum sulfate. In a further aspect, the aluminum-salt adjuvant is aluminum hydroxide. In another aspect, the one or more buffer systems is selected from the group consisting of acetate, succinate, citrate, prolamine, histidine, borate, carbonate and phosphate buffer systems. In a further aspect, the one or more buffer systems is selected from succinate and phosphate buffer systems. In one aspect, the one or more glass-forming agents is selected from the group consisting of trehalose, sucrose, ficoll, dextran, maltotriose, lactose, mannitol, hydroxyethyl starch, glycine, cyclodextrin, povidone, and potassium salts. In a specific aspect, the glass-forming agent is trehalose. In a further specific aspect, the glass-forming agent trehalose is present in a weight to volume concentration of from about 5% to about 20% in the liquid vaccine formulation. In another aspect, the glass-forming agent trehalose is present in a weight to volume concentration of from about 7% to about 15% in the liquid vaccine formulation. In one aspect, the freezing step comprises one of tray freezing, shelf freezing, spray-freezing and shell-freezing. In another aspect, the freezing step comprises spray-freezing. In a further aspect, the mean particle diameter of the reconstituted vaccine composition is less than 6 micrometers. In one aspect, the concentration of the glass forming agent in the selecting step is decreased as the rate of cooling the liquid vaccine formulation to a frozen state in the cooling step is increased.

In one embodiment, the disclosure provides an adjuvant composition for use in a dried vaccine composition, the adjuvant composition comprising: an aluminum-salt adjuvant, a glass-forming agent, and a buffer salt. In one aspect, the aluminum-salt adjuvant is selected from aluminum hydroxide and aluminum phosphate. In another aspect, the glass-forming agent is trehalose. In a further aspect, the buffer salt is selected from one or more of the group consisting of sodium succinate, potassium succinate, sodium phosphate and potassium phosphate.

In one embodiment, the disclosure provides an adjuvant-bound dried vaccine composition having limited mean particle diameter, the composition produced by a method comprising: blending at least one adjuvant, at least one glass forming agent, and at least one antigen in a buffer system to create a liquid vaccine formulation; cooling the liquid vaccine formulation rapidly to a frozen state to create a frozen vaccine formulation; and lyophilizing the frozen vaccine formulation to create a dried vaccine composition, wherein following dilution of the dried vaccine composition with an aqueous diluent to form a reconstituted vaccine composition, the mean particle diameter of the reconstituted vaccine composition is less than 10 micrometers.

In another embodiment, the disclosure provides a method of controlling particle size in a frozen vaccine formulation, the method comprising: combining at least one aluminum-salt adjuvant, at least one buffer system, at least one glass-forming agent, and at least one antigen to create a liquid vaccine formulation; freezing the liquid vaccine formulation to create a frozen vaccine formulation; and lyophilizing the frozen vaccine formulation to create a dried vaccine composition, wherein following thawing and dilution of the dried vaccine composition with an aqueous diluent to form a reconstituted vaccine composition the mean particle diameter of the reconstituted vaccine composition is less than 10 micrometers. In one aspect, the one or more aluminum-salt adjuvants is selected from the group consisting of aluminum hydroxide, aluminum phosphate and aluminum sulfate. In another aspect, the aluminum-salt adjuvant is aluminum hydroxide. In a further aspect, the one or more buffer systems is selected from the group consisting of acetate, succinate, citrate, prolamine, histidine, borate, carbonate and phosphate buffer systems. In one aspect, the one or more buffer systems is selected from succinate and phosphate buffer systems. In another aspect, the one or more glass-forming agents is selected from the group consisting of trehalose, sucrose, ficoll, dextran, maltotriose, lactose, mannitol, hydroxyethyl starch, glycine, cyclodextrin, povidone, and potassium salts. In a specific aspect, the glass-forming agent is trehalose. In a further specific aspect, the glass-forming agent trehalose is present in a weight to volume concentration of from about 5% to about 20% in the liquid vaccine formulation. In another specific aspect, the glass-forming agent trehalose is present in a weight to volume concentration of from about 7% to about 15% in the liquid vaccine formulation. In one aspect, the freezing step comprises one of tray freezing, shelf freezing, spray-freezing and shell-freezing. In another aspect, the freezing step comprises spray-freezing. In a further aspect, the mean particle diameter of the reconstituted vaccine composition is less than 6 micrometers.

In one aspect, the liquid vaccine formulation is prepared as a hypertonic mixture prior to freezing, wherein upon dilution of the dried vaccine composition with an aqueous diluent to form a reconstituted vaccine composition, the tonicity of the reconstituted vaccine composition is adjusted to isotonic levels.

BRIEF DESCRIPTION OF DRAWINGS

FIG. 11 shows amino acid sequences of recombinant botulinum neurotoxin E (SEQ ID NO: 1) and recombinant botulinum neurotoxin C (SEQ ID NO: 2) proteins.

FIG. 19 shows the percentage of monomer remaining during incubation determined by SDS-PAGE Gel (reducing condition) at (A) 4° C. incubation and (B) 30° C. incubation.

FIG. 22 shows the fraction of soluble rBoNTE recovered in AH-free FD (circles) and SFD (triangles) formulations stored at 4° C. (closed symbols) and 40° C. (open symbols).

FIG. 25 shows (a.) primary and (b.) secondary IgG1 responses to liquid rBoNTE(Hc) vaccines formulated with AH. Samples were stored at 4° C. (black bars with white markers) and 30° C. (gray bars with black markers).

FIG. 26 shows (a.) primary and (b.) secondary IgG1 responses to liquid rBoNTE(Hc) vaccines formulated without AH. AH was added prior to injection. Samples were stored at 4° C. (black bars with white markers) and 30° C. (gray bars with black markers).

FIG. 27 shows (a.) primary and (b.) secondary IgG1 responses to FD rBoNTE(Hc) vaccines formulated with AH. Samples were stored at 4° C. (black bars with white markers) and 40° C. (gray bars with black markers).

FIG. 29 shows (a.) primary and (b.) secondary IgG1 responses to SFD rBoNTE(Hc) vaccines formulated with AH. Samples were stored at 4° C. (black bars with white markers) and 40° C. (gray bars with black markers).

FIG. 30 shows (a.) primary and (b.) secondary IgG1 responses to SFD rBoNTE(Hc) vaccines formulated without AH. AH was added during reconstitution. Samples were stored at 4° C. (black bars with white markers) and 40° C. (gray bars with black markers).

FIG. 32 shows amino acid sequences of recombinant botulinum neurotoxin A (SEQ ID NO: 3) and recombinant botulinum neurotoxin B (SEQ ID NO: 4) proteins.

FIG. 33 shows the amino acid sequence of recombinant botulinum neurotoxin F (SEQ ID NO: 5).

MODES FOR CARRYING OUT THE INVENTION

Figure 1:
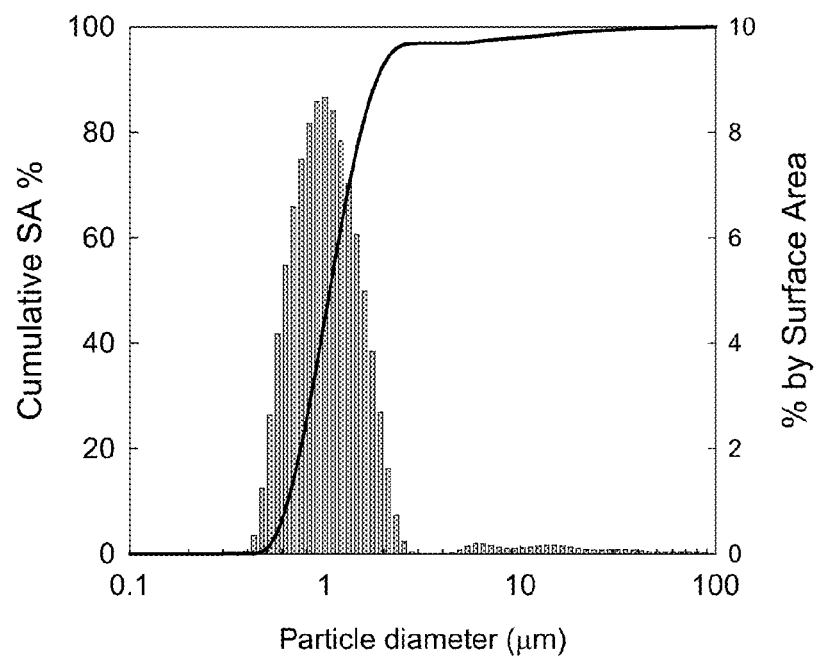
FIG. 1 shows particle size distribution of a solution of Alhydrogel™ measured by a Beckman-Coulter LS230 laser diffraction system prior to freezing.

The disclosure provides a method of production of an immunologically-active adjuvant-bound freeze dried vaccine preparation. In one embodiment, an aluminum-salt adjuvant is combined in a buffer system with a glass-forming agent and a vaccine antigen; then lyophilized to produce a lyophilized vaccine composition. The lyophilized vaccine composition thus produced is reconstituted in an aqueous buffer system and used to immunize an animal. Compared to a liquid vaccine composition, the lyophilized vaccine composition has improved stability and comparable or improved immunogenicity.

The term "lyophilization" refers to freezing of a material at low temperature followed by dehydration by sublimation, usually under a high vacuum. Lyophilization is also known as freeze drying. Many techniques of freezing are known in the art of lyophilization such as tray freezing, shelf freezing, spray-freezing, shell-freezing and liquid nitrogen immersion. Each technique will result in a different rate of freezing. Shell freezing may be automated or manual. For example, flasks can be automatically rotated by motor driven rollers in a refrigerated bath containing alcohol, acetone, liquid nitrogen, or any other appropriate fluid. A thin coating of product is evenly frozen around the inside "shell" of a flask, permitting a greater volume of material to be safely processed during each freeze drying run. Tray freezing may be performed by, for example, placing the samples in lyophilizer, equilibrating 1 hr at a shelf temperature of 0° C., then cooling the shelves at 0.5° C./min to −40° C. Spray-freezing, for example, may be performed by spray freezing into liquid, dropping by ~20 µl droplets into liquid $N_2$, spray freezing into vapor over liquid, or by other techniques known in the art.

The term "antigen" refers to any molecule that is capable of eliciting an immune response, whether a cell-mediated or humoral immune response, whether in the presence or absence of an adjuvant. An antigen can be any type of molecule, e.g., a peptide or protein, a nucleic acid, a carbohydrate, a lipid, and combinations thereof A "vaccine antigen" is an antigen that can be used in a vaccine preparation. A "therapeutic antigen" is an antigen that can be used for therapeutic purposes.

The terms "polypeptide", "peptide", and "protein" are used interchangeably herein to refer to a polymer comprising amino acid residues predominantly bound together by covalent amide bonds. The terms apply to amino acid polymers in which one or more amino acid residue may be an artificial chemical mimetic of a naturally occurring amino acid, as well as to naturally occurring amino acid polymers and non-naturally occurring amino acid polymers. As used herein, the terms encompass amino acid chains of any length, including full length proteins, wherein the amino acids are linked by covalent peptide bonds. The protein or peptide may be isolated from a native organism, produced by recombinant techniques, or produced by synthetic production techniques known to one skilled in the art.

The term "recombinant protein" refers to a polypeptide of the present disclosure which is produced by recombinant DNA techniques, wherein generally, DNA encoding a polypeptide is inserted into a suitable expression vector which is in turn used to transform a heterologous host cell (e.g. a microorganism or yeast cell) to produce the heterologous protein.

Likewise the term "recombinant nucleic acid" or "recombinant DNA" refers to a nucleic acid or DNA of the present disclosure which is produced by recombinant DNA techniques, wherein generally, DNA encoding a polypeptide is inserted into a suitable expression vector which is in turn used to transform a host cell to produce the heterologous protein.

The term "vaccine" is used to define an antigenic preparation used to produce active immunity to a disease, in order to prevent or ameliorate the effects of infection. The antigenic moiety making up the vaccine can be either a live or killed microorganism, or a natural product purified from a microorganism or other cell including, but not limited to tumor cells, a synthetic product, a genetically engineered protein, peptide, polysaccharide or similar product or an allergen.

The term "cell-mediated immune response" is defined as an immune response mediated by cells or the products they produce, such as cytokines, rather than by antibodies. It includes, but is not limited to, delayed type hypersensitivity and cytotoxic T cells.

The term "humoral immune response" is an immune response that is mediated by B cells (B lymphocytes) which produce antibodies. Secreted antibodies bind to antigens on the surfaces of invading microbes, which marks them for destruction.

The term "immunogen" refers to an antigen which elicits a strong immune response, particularly in the context of protective immunity to pathogenic organisms.

The term "immunologically active" refers to the ability to raise one or more of a humoral response or a cell mediated response specific to an antigen.

The term "adjuvant" means compounds that, when used in combination with specific vaccine antigens in formulations, augment or otherwise alter or modify the resultant immune responses. An adjuvant combined with a vaccine antigen increases the immune response to the vaccine antigen over that induced by the vaccine antigen alone. An adjuvant may augment humoral immune responses or cell-mediated immune responses or both humoral and cell-mediated immune responses against vaccine antigens.

The term "excipient" refers to an inactive or inert substance which is added to a drug or vaccine formulation, usually to provide stability or bulk.

The term "animal" refers to vertebrates, preferably mammals, and most preferably humans. Likewise, a "patient" or "subject" to be treated by the method of the disclosure can mean either a human or a non-human animal.

The term "pharmaceutically acceptable" means a material that is not biologically or otherwise undesirable, i.e., the material may be administered to an individual along with the selected compound without causing any undesirable biological effects or interacting in a deleterious manner with any of the other compounds of the pharmaceutical composition in which it is contained.

The phrase "derived from", with respect to a recombinant gene, is meant to include within the meaning of "recombinant protein" those proteins having an amino acid sequence of a native polypeptide, or an amino acid sequence similar thereto which is generated by mutations including substitutions, insertions, and deletions (including truncation) of a naturally occurring form of the polypeptide.

The term "zeta potential" refers to a physical measurement of a colloidal system by electrophoresis. It gives the value of the potential (in mV) of a colloid in a suspension at the boundary between the Stern layer and the diffuse layer. In other words, the zeta potential in a colloidal system is the difference in potential between the immovable layer attached to the surface of the dispersed phase and the dispersion medium. The zeta potential is related to stability of suspensions of particles. Zeta potential may be adjusted, in part, for example, by adjusting the concentration of an electrolyte in the buffer system.

The term "particle size distribution" refers to classification of powdered materials as determined by various testing methods defining the particle sizes and quantities in a given sample.

The term "glass-forming agent" refers to a material, or excipient, which solidifies into an amorphous solid material at the materials glass transition temperature. Examples of these glass-forming agents may be found, for example in Hatley and Blair "Stabilisation and delivery of labile materials by amorphous carbohydrates and their derivatives" J.

Molecular Catalysis B: Enzymatic 7: 11-19 (1999). A partial list of glass-forming agents includes trehalose, sucrose, ficoll, dextran, maltotriose, lactose, and mannitol. In addition, hydroxyethyl starch, glycine, cyclodextrin, povidone (polyvinylpyrrolidone), and potassium salts may be used as excipients in this capacity. In one embodiment, one or more of trehalose, sucrose, ficoll, dextran, maltotriose, lactose, mannitol, hydroxyethyl starch, glycine, cyclodextrin and povidone are used as glass-forming agents. In one aspect, the glass-forming agent is a crystallization-inhibiting agent. In one aspect, sucrose is the glass-forming agent. In another aspect, trehalose is the glass-forming agent.

The term "buffer" or "buffer system" refers to a pharmaceutically acceptable aqueous buffer system comprising pyrogen-free water system with the ability to resist a change in pH upon addition of an inorganic compound, organic compound, acid, alkali, or dilution with a solvent or diluent. Buffer characteristics are defined in detail in, for example, Remington's Pharmaceutical Sciences, 18th Ed. Gennaro Ed., Mack Publishing Co., Easton Pa. (1990) pp. 241-243. In one aspect, the buffer system of the present disclosure is selected to optionally maximize binding between protein and adjuvant. In another aspect, the buffer system is selected to maximize antigen stability. The buffer of the present disclosure is additionally selected to avoid significant pH changes during freezing. Buffers that are suitable for use in the present disclosure comprise, for example, sodium or potassium buffer salts of one or more of acetate, succinate, citrate, prolamine, histidine, borate, carbonate and phosphate buffers. In one embodiment, sodium or potassium buffer salts are employed in the buffer system. In one aspect, the pH of the buffer system may be adjusted by addition of a conjugate acid of the buffer salt, another acid or a base. In one aspect, the pH of the buffer system is selected to maintain the antigen in a specific ionized or non-ionized form to tailor the interaction and binding of the antigen to the adjuvant. In another aspect, the pH of the buffer is selected to optimize the absorption characteristics of the adjuvant vaccine composition in the physiological environment at the site of administration, such as intramuscular, intradermal, mucosal (e.g. intranasal), oromucosal, or subcutaneous environments. In one aspect of the disclosure, the buffer system is selected from either, or a combination of, a succinate and a phosphate buffer system. In one specific aspect, 25 mM sodium succinate, 15 mM sodium phosphate, at pH 5.0. In another specific aspect, the buffer system is 25 mM sodium succinate, pH 4.0.

The term "diluent" refers to any liquid or solid material used to dilute the lyophilized vaccine composition. In one embodiment, the diluent is a pharmaceutically acceptable diluent which is suitable for injection. In one aspect, the diluent is an aqueous, pharmaceutically acceptable diluent which is used to solubilize the lyophilized vaccine composition. In another aspect, the diluent is used to prepare the lyophilized vaccine composition for administration to a patient in need thereof.

The "route of administration" refers to the method by which the adjuvant vaccine composition is administered to the patient in need. In one embodiment, the route of administration is selected from one or more of intramuscular, intradermal, mucosal (e.g. intranasal), oromucosal, and subcutaneous environments. It is further contemplated that the initial immunization by one route of administration does not limit the site, or route of administration of subsequent, or booster, immunizations.

The term "aluminum-salt adjuvant" refers to an adjuvant substantially comprising aluminum hydroxide (e.g. Alhydrogel™), aluminum phosphate (e.g. Adju-Phos™), or aluminum sulfate (alum).

The term "Alhydrogel™" refers to a commercially available aluminum hydroxide gel, (AlO(OH), boehmite). Aluminum hydroxide gel has many biomedical applications as an adjuvant in bacterins and vaccines.

Aluminum hydroxide adjuvant, chemically aluminum oxyhydroxide or boehmite, consists of primarily needle-like particles with diameters of 2 $nm^3$. These particles form stable aggregates with diameters of 1-10 μm in solution and have a surface area of around 510 $m^2/g$ when measured by x-ray diffraction and water sorption (Johnston C T, Wang S L, Hem S L 2002, "Measuring the surface area of aluminum hydroxide adjuvant. J Pharm Sci 91(7):1702-1706"; Lindblad EB 2004. "Aluminium compounds for use in vaccines" Immunol Cell Biol 82(5):497-505).

Aluminum hydroxide has a point of zero charge (PZC, i.e. the pH where the net surface charge on the particles is zero) in the range of pH 9-11, and thus has a positive surface charge at pH values below pH 7 (Callahan et al., 1991; Goldberg S, Davis J A, Hem J D. 1996. "The Surface Chemistry of Aluminum Oxides and Hydroxides". In Sposito G, editor The Environmental Chemistry of Aluminum, 2nd ed., Boca Raton, Fla.: Lewis Publishers. p 271-331). The PZC of the adjuvant, and thus surface charge, can be modified by the adsorption of buffer salts. Phosphate and citrate anions are able to substitute for hydroxyl groups on the surface of this adjuvant, lowering its PZC, and allowing proteins with a wide range of isoelectric points to adsorb to it. (Hem and White 1984; Rinella et al., 1996; Chang et al., 1997, Role of the electrostatic attractive force in the adsorption of proteins by aluminum hydroxide adjuvant. PDA J Pharm Sci Technol 51(1):25-29; Vessely et al., 2007, Effects of Solution Conditions and Surface Chemistry on the Adsorption of Three Recombinant Botulinum Neurotoxin Antigens to Aluminum Salt Adjuvants, J. Pharmaceut. Sci., 96, (9): 2375-2389; Chang et al., 2001. Degree of antigen adsorption in the vaccine or interstitial fluid and its effect on the antibody response in rabbits, Vaccine 19(20-22):2884-2889; Iyer et al., 2003, Relationship between the degree of antigen adsorption to aluminum hydroxide adjuvant in interstitial fluid and antibody production, Vaccine 21(11-12):1219-1223). For the case of phosphate ion, adsorption to aluminum hydroxide does not change the primary crystalline dimension of the adjuvant, indicating that the adsorption is primarily on the surface of the adjuvant particles. (Chang et al., 1997).

Although freezing of suspensions containing aluminum-salt adjuvants causes freeze-concentration, it is unlikely that high adjuvant concentration alone is responsible for the observed aggregation. Without being bound by theory, it is possible freeze-concentration-induced phase changes and ion-exchange reactions on aluminum hydroxide particle surfaces initiate aggregation during freezing and lyophilization. The extent to which these phase changes and reactions occur will affect the resulting particle aggregation. It is one object of the disclosure to control, or limit, aggregation of the adjuvant.

In one embodiment of the disclosure, adjuvant aggregation and crystallization is limited or controlled by changing the kinetics of freezing and the addition of a suitable glass-forming excipient. The resulting preparations are characterized by particle size distribution (PSD), zeta potential, and X-ray powder diffraction (XRPD).

Figure 3:
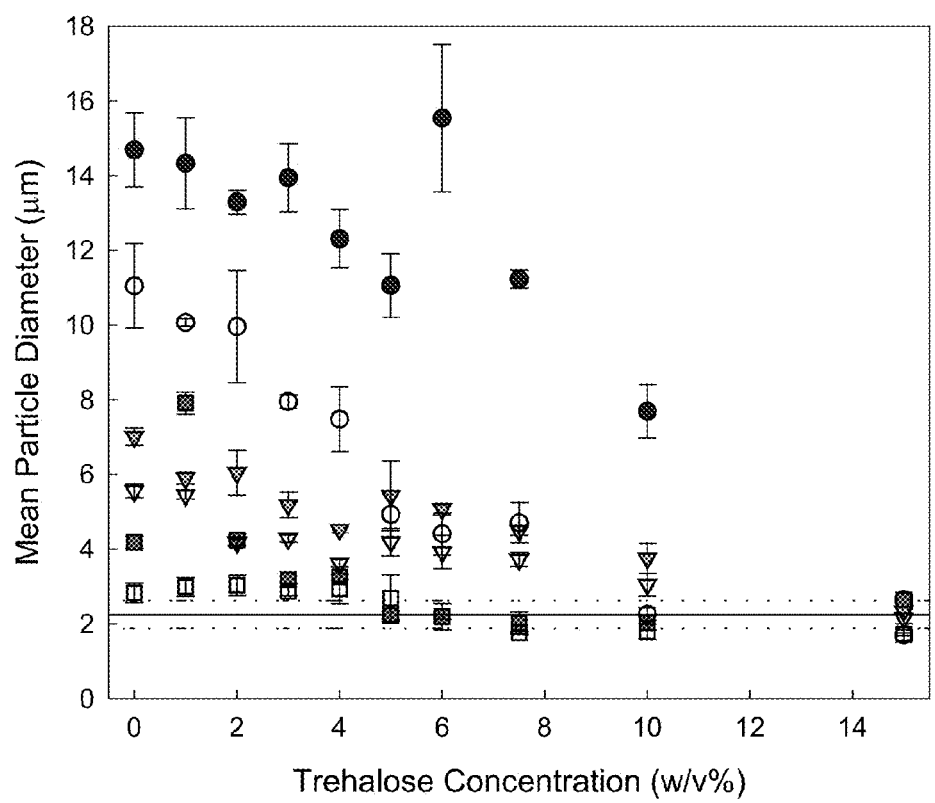
FIG. 3 shows the surface area weighted mean particle diameter of 0.2% Alhydrogel™ after processing in 25 mM sodium succinate (pH 4.0) as a function of trehalose concentration and processing. Samples were cooled at various rates to a frozen solid: (○) tray frozen at 0.5° C./min, (□) frozen by immersion of bottom of vial in liquid nitrogen, and (∆) spray-frozen. Solid markers indicate samples following freeze-drying and reconstitution, open markers frozen and thawed. Solid and dashed lines indicate unprocessed Alhydrogel™+/−standard deviation respectively.

The kinetics of freezing are varied by utilization of various conventional lyophilization techniques such as tray freezing, freezing of individual sample vials by immersion in liquid nitrogen, and spray freezing. The effects of different cooling rates on mean particle diameter of Alhydrogel™ is shown in FIG. 3. In one embodiment of the disclosure, the method comprises freezing the adjuvant-vaccine composition by tray freezing, immersion in liquid nitrogen, or spray freezing. In one aspect, the method comprises spray freezing of the adjuvant-vaccine composition prior to lyophilization.

Figure 2:
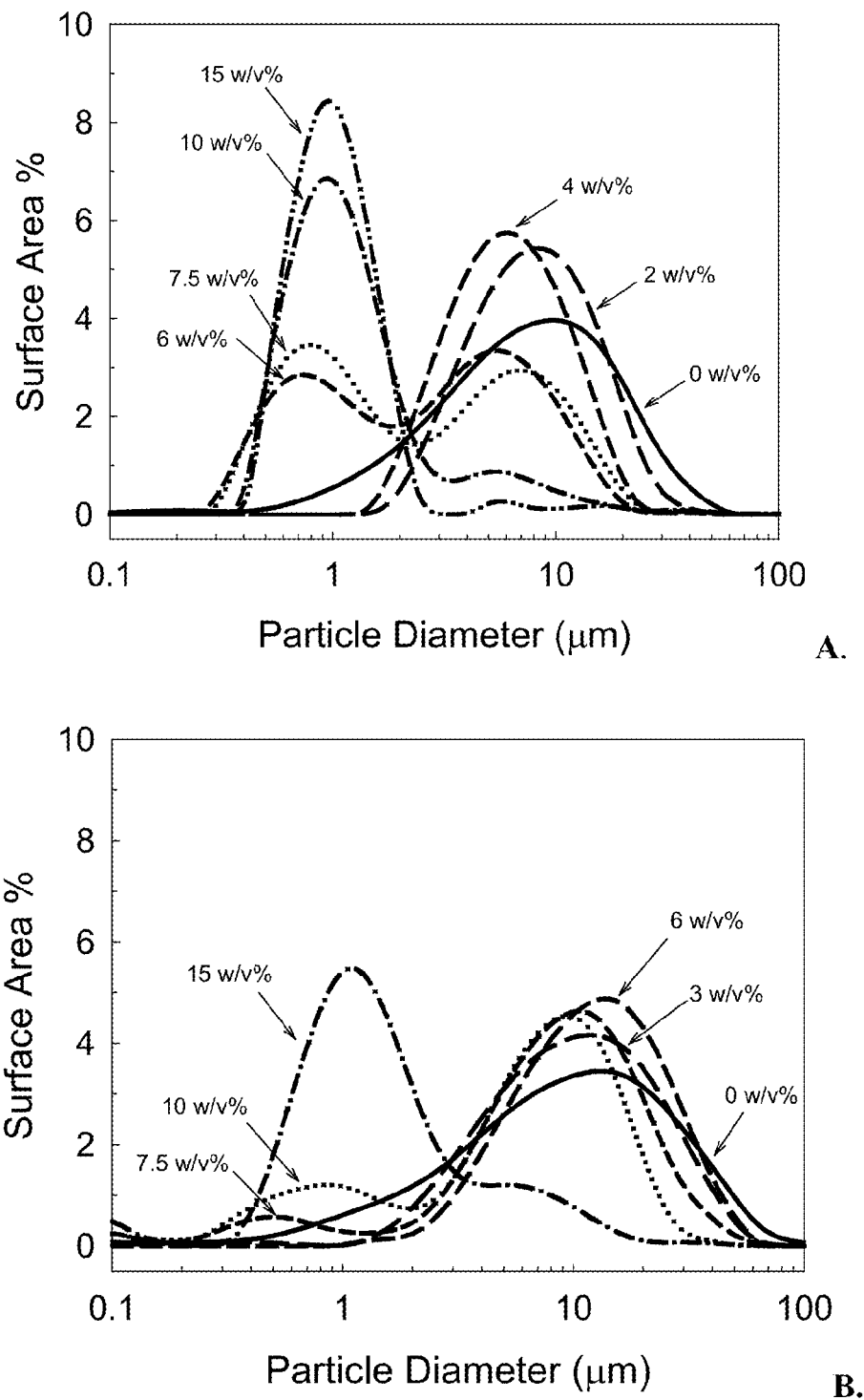
FIG. 2 shows particle size distribution of 0.2% Alhydrogel™ following A.) freezing and thawing and B.) freeze-drying and reconstitution with varying trehalose weight/volume concentrations.

In another embodiment of the disclosure, adjuvant aggregation and crystallization is limited or controlled by the addition of a suitable glass-forming agent or excipient. Particle size distributions (PSD) of Alhydrogel™ on addition of various concentrations of the glass-forming agent trehalose following freeze-thawing and freeze-drying and reconstitution are shown in FIG. 2. Mean particle diameter as a function of trehalose concentration (0 to 15% w/v) is shown in FIG. 3. In one embodiment, the glass forming agent is trehalose. In a specific aspect of the method, trehalose in a w/v range from about 5% to about 20% is used as the glass-forming agent. In further a specific aspect, trehalose in a w/v range of from about 7.5% to about 15% is used as the glass-forming agent.

In one aspect of the disclosed method, the cooling rate of samples to a frozen state affects the particle size distribution (PSD) of the adjuvant particles in solution. The faster the cooling rate of samples to a frozen state, the less aggregation occurs and a lower concentration of a glass forming agent is required to control aggregation of the adjuvant and the vaccine-adjuvant composition. In one aspect of the disclosure, the technique of spray-freezing the sample results in a relatively faster cooling rate. The technique of freezing the sample by immersion of the sample vial into liquid nitrogen results in a relatively moderate cooling rate to a frozen state. The technique of tray freezing results in a relatively slower rate of cooling to a frozen state. The technique of freezing may be selected based upon the scale of the procedure, and a slower cooling rate to a frozen state may be compensated by an increase in the concentration of glass former to control aggregation and crystallization of the adjuvant vaccine composition.

In a further aspect of the disclosure, a combination of cooling rate, and adjustment of the type and concentration of buffer salts with addition of one or more glass-forming agents or excipients is used to control and limit aggregation and crystallization of the lyophilized vaccine composition. In one aspect, spray freeze-drying and switching to potassium buffer salts from sodium salts reduces the overall crystallinity and limits the monobasic salt crystallization. In another aspect, sodium buffer salts are used to limit aggregation. In one aspect, addition of sodium or potassium buffer salts is used to alter the zeta potential of the formulation.

In vaccine formulations that contain adjuvants, both the antigen and the adjuvant must be stabilized against degradation during storage. Lyophilization is often the most practical approach to stabilize therapeutic protein formulations for long-term storage, and it would be desirable to apply this strategy to adjuvanted vaccine formulations as well. Unfortunately, when vaccines formulated with aluminum-salt adjuvants are frozen or lyophilized, a loss of potency is often reported. (Diminsky, et al., 1999, Physical, chemical and immunological stability of CHO-derived hepatitis B surface antigen (HBsAg) particles, Vaccine 18(1-2): 3-17; Maa et al., 2003). This loss has previously been attributed to aggregation of the adjuvant particles during freezing (Maa et al. 2003). In one aspect, adjuvant aggregation during freezing and lyophilization is avoided by manipulating the kinetics of freezing and/or the glass-forming propensities of added excipients to manufacture thermally stable, adjuvanted vaccines with long storage lifetimes.

Antigens to be used in the vaccines of the present disclosure are compounds which, when introduced into a mammal, will result in the formation of antibodies and optionally cell mediated immunity. Representative of the antigens that can be used according to the present disclosure include, but are not limited to, natural, recombinant or synthetic products derived from viruses, bacteria, fungi, parasites and other infectious agents in addition to autoimmune diseases, hormones or tumor antigens which might be used in prophylactic or therapeutic vaccines and allergens. The viral or bacterial products can be components which the organism produced by enzymatic cleavage or can be components of the organism that were produced by recombinant DNA techniques that are well-known to those of ordinary skill in the art. The following is a partial list of representative antigens: Viruses: Rotavirus, Foot and mouth disease, Influenza, Parainfluenza, Herpes species (Herpes simplex, Epstein Barr virus, Chicken pox, pseudorabies, Cytomegalovirus), Rabies, Polio, Hepatitis A, Hepatitis B, Hepatitis C, Hepatitis E, Measles, Distemper, Venezuelan equine encephalomyelitis, Feline leukemia virus, Reovirus, Respiratory syncytial virus, Lassa fever virus, Polyoma tumor virus, Canine parvovirus, Papilloma virus, Tick borne encephalitis, Rinderpest, Human rhinovirus species, Enterovirus species, Mengo virus, Paramyxovirus, Avian infectious bronchitis virus, HTLV 1, HIV-1, HIV-2, Influenza A and B, LCMV (lymphocytic choriomeningitis virus), Parovirus, Adenovirus, Togavirus (rubella, yellow fever, dengue fever), Bovine respiratory syncicial virus, Corona virus Bacteria: *Bordetella pertussis, Brucella abortus, Escherichia coli, Salmonella* species, *salmonella typhi*, Streptococci, *Vibrio* (*V. cholerae, V. parahaemolyticus*), *Shigella, Pseudomonas, Brucella* species, *Mycobacteria* species (tuberculosis, avium, BCG, leprosy,), Pneumococci, Staphylococci, *Enterobacter* species, *Rochalimaea henselae, Pasteurella* (*P. haemolytica, P. multocida*), *Chlamydia* (*C. trachomatis, C. psittaci, Lymphogranuloma venereum*), Syphilis (*Treponema pallidum*), *Haemophilus* species, Mycoplasmosis, Lyme disease (*Borrelia burgdorferi*), Legionnaires' disease, Botulism (*Clostridium botulinum*), *Corynebacterium diphtheriae, Yersinia entercolitica*

Ricketsial Infections, Rocky mountain spotted fever, Typhus, *Ehrlichia* Parasites and Protozoa: Malaria (*Plasmodium falciparum, P. vivax, P. malariae*), Schistosomes, Trypanosomes, *Leishmania*, Filarial nematodes, Trichomoniasis, Sarcosporidiasis, *Taenia* (*T. saginata, T. solium*), *Leishmania, Toxoplasma gondii*, Trichinelosis (*Trichinella spiralis*), Coccidiosis (*Eimeria* species)

Fungus: *Cryptococcus neoformans; Candida albicans; Apergillus fumigatus*, Coccidioidomycosis Subunit recombinant proteins: Herpes simplex, Epstein Barr virus, Hepatitis B, Pseudorabies, Flavivirus (Denge, Yellow fever), *Neisseria gonorrhoeae*, Malaria (circumsporozoite protein, merozoite protein), Trypanosome surface antigen protein, Pertussis, Alphaviruses, Adenovirus Proteins: Diphtheria toxoid, Tetanus toxoid, meningococcal outer membrane protein (OMP), Streptococcal M protein, Hepatitis B, Influenza hemagglutinin, Cancer antigen, tumor antigens, Toxins, Exotoxins, Neurotoxins, Cytokines and Cytokine receptors, Monokines and monokine receptors Synthetic or recombinant peptides: Malaria, Influenza, Foot and mouth disease virus, Hepatitis B, Hepatitis C, Botulinum Neurotoxin C, Botulinum Neurotoxin E Polysaccharides: Pneumococcal polysaccharide, Haemophilis influenza (polyribosyl-ribitolphosphate (PRP)), *Neisseria meningitides, Pseudomonas aeruginosa, Klebsiella pneumoniae*

Oligosaccharides: Pneumococcal
Allergens: Plant pollens, Animal dander, dust mites.

In one embodiment of the disclosure, the vaccine antigen is a recombinant protein. In a specific embodiment, the antigen is a *Clostridium botulinum* neurotoxin recombinant protein.

In one specific aspect, the antigen is *C. botulinum* neurotoxin E, the amino acid sequence of which is shown in FIG. 11 (SEQ ID NO: 1). In another aspect, the antigen is botulinum neurotoxin C the amino acid sequence of which is shown in FIG. 11 (SEQ ID NO: 2). In another aspect, the antigen is botulinum neurotoxin A the amino acid sequence of which is shown in FIG. 32 (SEQ ID NO: 3). In another aspect, the antigen is botulinum neurotoxin B the amino acid sequence of which is shown in FIG. 32 (SEQ ID NO: 4). In another aspect, the antigen is botulinum neurotoxin F the amino acid sequence of which is shown in FIG. 33 (SEQ ID NO: 5).

In one embodiment, the antigen is selected from one or more of seven recombinant protein antigens created as part of the development of a heptavalent vaccine against the neurotoxins (Smith 1998; Smith et al. 2004). These protein antigens (identified as rBoNTA(Hc)-rBoNTG(Hc)) consist of 50 kDa portions of the C-terminal domain of the heavy chains and have no neurotoxin activity (DePaz et al., 2005). The seven antigens rBoNTA(Hc)-rBoNTG(Hc) are distinct proteins with different properties. The isoelectric points for the seven serotypes range from 5.6 to 9.3, complicating formulation strategies for maximizing binding of the antigens to adjuvants and for providing long-term stability for each antigen. (ewDux et al., 2006, Purification and scale-up of a recombinant heavy chain fragment C of botulinum neurotoxin serotype E in *Pichia pastoris* GS115, Protein Expr Purif 45(2): 359-67). Vessely et al. 1997 observed differences in the ability of rBoNTA(Hc), rBoNTB(Hc) and rBoNTE(Hc) to bind to and subsequently desorb from aluminum salt adjuvants. Estey et al. observed time-dependent changes in desorption of rBoNTA(Hc), rBoNTB(Hc) and rBoNTE(Hc) antigens from aluminum hydroxide adjuvant as well as evidence of chemical degradation such as oxidation and deamidation in stored aqueous monovalent (rBoNTA(Hc), rBoNTB(Hc) or rBoNTE(Hc)) and trivalent (rBoNTABE(Hc)) vaccines. (Estey et al., 2007, Effects of Solution Conditions and Surface Chemistry on the Adsorption of Three Recombinant Botulinum Neurotoxin Antigens to Aluminum Salt Adjuvants, Journal of Pharmaceutical Sciences, Volume 96, Issue 9, 2375-2389). The chemical degradation of a trivalent recombinant protein vaccine against botulinum neurotoxin by lysc peptide mapping and MALDI-TOF mass spectrometry"). Chemical degradation of antigens was accelerated in the presence of aluminum hydroxide adjuvant in aqueous solution (Carpenter, J. F. et A, Evaluation of Chemical Degradation of a Trivalent Recombinant Protein Vaccine Against Botulinum Neurotoxin by LysC Peptide Mapping and MALDI-TOF Mass Spectrometry, Journal of Pharmaceutical Sciences, submitted).

One embodiment of the present invention provides a stable immunologically-active adjuvant-bound dried vaccine composition comprising an adjuvant, a glass-forming agent, and one or more of rBoNTA(Hc) (SEQ ID NO: 3), rBoNTB(Hc) (SEQ ID NO: 4), rBoNTC(Hc) (SEQ ID NO: 2), rBoNTD (Hc), rBoNTE(Hc) (SEQ ID NO: 1), rBoNTF(Hc) (SEQ ID NO: 5), and rBoNTG(Hc).

Recombinant protein antigens may be produced and purified by methods known to one skilled in the art; see for example: ewDux et al., 2006 and Sinha et al., 2007, Cell bank characterization and fermentation optimization for production of recombinant heavy chain C-terminal fragment of botulinum neurotoxin serotype E (rBoNTE(H(c)): antigen E) by *Pichia pastoris*, J Biotechnol (2007) 127(3):462-474; each of which is incorporated herein by reference.

In a further embodiment of the disclosure, one or more of the vaccine antigens may be combined to create a bivalent or polyvalent vaccine composition.

In another embodiment, the antigen is a non-pathogenic protein which can be used as a model to determine immunogenicity and other characteristics of a vaccine composition. In one aspect, the non-pathogenic protein vaccine antigen is lysozyme.

Immunogenicity, or efficacy of protective immunity, of reconstituted freeze dried adjuvant-vaccine compositions can be determined by standard techniques known to those skilled in the art. For example, in vitro tests for immunogenicity include evaluation of antibody levels in the serum of immunized animals determined by enzyme-linked immunosorbent assays (ELISAs) or serum neutralization assays. One advantage of ELISA is that reactive antibody class and subclass may be determined. An example of an in vivo test of immunogenicity is animal survival upon challenge with pathogen (or pathogenic organism). Survival of immunized animals is compared to survival of non-immunized animals to determine immunogenicity.

EXAMPLES

Example 1

Particle Size Distribution (PSD) of Aluminum Hydroxide Adjuvant Materials

Trehalose dehydrate (high purity, low endotoxin) was obtained from Ferro Pfanstiehl (Cleveland, Ohio). Succinic acid was purchased from Sigma Chemical Company (St. Louis, Mo.). Alhydrogel™ 2.0% (aluminum hydroxide adjuvant), made by Brenntag Biosector, was purchased through E.M. Sergeant Pulp & Chemical Co, Inc (Clifton, N.J.). 3-ml and 5-ml lyophilization vials and caps were obtained from West Pharmaceutical Services.

Sample Preparation

Aqueous solutions were prepared containing different concentrations of trehalose (0-15 w/v %). Unless otherwise noted, samples were prepared in 25 mM sodium succinate at pH 4.0 and contained 0.2 w/v % Alhydrogel™. Samples were processed as one-ml aliquots. With the exception of the adjuvant, all aqueous solutions were passed through a 0.2 μm filter prior to formulation.

Particle Aggregation Studies in Liquid Suspensions of Alhydrogel™

To examine the effects of high concentration of adjuvant on the aggregation behavior of Alhydrogel™, solutions of the adjuvant were concentrated by centrifugation for 10 minutes. Following centrifugation, the volume of the supernatant was examined to determine the approximate concentration of adjuvant particles. The adjuvant was then gently resuspended by pipetting the pellet and the resulting PSD was determined.

To mimic freeze-concentration of buffer salts during lyophilization, Alhydrogel™ particles (0.2%) were incubated in 500 mM succinate, pH 4.0 at 4° C. The PSD of this solution was then examined after incubation.

Lyophilization

An FTS Systems Lyostar lyophilizer was used for the freeze-drying of samples. Samples were frozen at various cooling rates as follows from slowest to fastest: (i.) Frozen by placing the samples in lyophilizer, equilibrating 1 hr at a shelf temperature of 0° C., then cooling the shelves at 0.5° C./min to −40° C. ("tray-freezing"); (ii.) Frozen by immersion of bottom of vial into liquid $N_2$; and (iii.) Spray-freezing by dropping by ~20 μl droplets into liquid $N_2$. Tray-frozen and liquid $N_2$-immersed samples were processed in 3-ml lyophilization vials, while the spray-frozen samples were processed in 5-ml lyophilization vials. Vials containing samples frozen using liquid $N_2$ were quickly transferred to the lyophilizer placed on lyophilizer shelves pre-cooled to −40° C. Samples were spaced in the lyophilizer so that they were each separated from one another and were encircled with a row of vials containing water.

Primary drying of the samples was achieved by setting the shelf temperature to −20° C. and applying a vacuum at 60 mTorr for 20 hours, and was followed by secondary drying, in which shelf temperatures were ramped from −20° C. to 0° C. at 0.2° C./min, to 30° C. at 0.5° C./min and finally held at 30° C. for 5 hours. Samples were sealed under vacuum and reconstituted with DI water prior to analysis. Freeze-thaw samples were thawed on a laboratory bench (21° C.+/−2° C.) after freezing.

To examine the dependency of the temperature at which samples were thawed on the PSD of the adjuvant, samples were prepared in 7.5 w/v % trehalose, 25 mM sodium succinate pH 4 with 0.2% Alhydrogel™. Samples were tray-frozen to −40° C. and were then thawed either in a 37° C. water bath, on a laboratory bench top at ambient room temperature (21° C.+/−2° C.), or in the refrigerator (4° C.).

Particle Size Distributions

PSD's were measured using a Beckman-Coulter LS230 laser diffraction particle size analyzer. Three one-ml samples were required for each run, and three replicates of each run were completed per formulation. Reported PSD's are surface area weighted and are composites of three runs.

Zeta Potential Measurement

Zeta potential measurements were taken on a Nicomp 380ZLS from Particle Sizing Systems. Samples were freeze-dried ("tray-frozen") or spray freeze-dried according to the methods presented above in 7.5 w/v % trehalose, 25 mM sodium succinate, pH 4.0. The Alhydrogel™ concentration was 0.2 w/v %. The Alhydrogel™ samples were diluted six-fold in the formulation buffer prior to analysis. For the aging study, Alhydrogel™ was prepared as a 0.2 w/v % solution in 7.5 w/v % trehalose, 25 mM succinate at pH 4.0 and stored at 4° C. Five individual samples were prepared for analysis, and the zeta potential and pH were monitored over a two week period. The solutions were inverted gently on a daily basis to resuspend the particles.

Frozen pH Measurements

The pH of frozen succinate solutions was measured using a Friscolyte "B" electrode connector (Mettler Toledo) using a method described by Roy et al. (Roy, S., et al., "Effects of benzyl alcohol on aggregation of recombinant human interleukin-1-receptor antagonist in reconstituted lyophilized formulations" J Pharm Sci, 2005. 94(2): p. 382-96). Samples (3 ml aliquots) were placed inside a 15-ml Falcon tube (Becton Dickinson) which was placed inside a 250-ml container containing glycerol that was secured in a propylene glycol circulating bath. The level of the glycerol in the container was lower than the propylene glycol in the temperature-controlled circulating bath. The temperature of the samples was monitored with a T-type thermocouple (Omega Scientific). A calibration curve was prepared by measuring the millivolt (mV) readings for standard buffers at pH 4, 7, and 10 and at temperatures of 25, 10, and 0° C. A plot of known pH values versus the measured mV readings was constructed. The slopes and intercepts of these three curves were plotted against the reciprocal of absolute temperature. Solutions of 25 mM sodium succinate, pH 4.0 containing 0 or 7.5 w/v % trehalose and 0.2% Alhydrogel™ were placed in the sample container which had equilibrated overnight to −22° C. The mV reading was recorded after the temperature of the sample had equibrated to −20° C. The pH values of the frozen solutions were obtained by extrapolation of the calibration curves to −20° C.

X-Ray Powder Diffraction (XRPD)

The crystalline content of dried samples containing mixtures of sodium succinate, potassium succinate, trehalose, and Alhydrogel™ was characterized using a Scintag diffractometer with a CuK radiation source (wavelength 1.5405 Å). Samples were prepared as random powder mounts after grinding the dried samples using a mortar and pestle until a powder was formed. The diffractometer was operated at power settings of 25 mA and 40 kV. The scan measured diffraction angles from 5 to 60° with a step width of 0.02° at a scan rate of 2°/min.

Results

PSD of Aqueous Aluminum Hydroxide Adjuvant Suspensions

The particle size distribution of a solution of Alhydrogel™ measured by a Beckman-Coulter LS230 laser diffraction system prior to freezing is presented in FIG. 1.

The size of the aluminum hydroxide particles is centered around 1 micrometer. Aluminum hydroxide particles in samples stored at 2-8° C. settle after about a month of storage but were resuspended by gentle shaking. Despite the high concentration of particles in the settled fraction, the PSD of samples stored in this manner do not change over the course of a year (data not shown). Thus, high particle concentrations alone cannot explain the observed aggregation that occurs as a result of freeze-concentration.

To assess the extent to which ice crystals mechanically pushing adjuvant particles together is responsible for aggregation, samples of Alhydrogel™ suspensions were concentrated by centrifugation to a concentration about 5 times greater of that of the starting particle concentration. These samples were able to be resuspended after gentle mixing with no significant change in the PSD of the adjuvant particles, indicating that physically pushing together adjuvant particles does not result in aggregation.

PSD of Processed Aluminum Hydroxide Adjuvant Suspensions—Effect of Glass-Forming Excipients To assess the effect of glass-forming excipients on the PSD of Alhydrogel™ suspensions after freeze-thawing or freeze-drying, PSDs were measured for freeze-thawed or freeze-dried and reconstituted samples containing various concentrations of trehalose (0-15 w/v %). Three freezing methods were tested: (i.) tray freezing; (ii.) freezing by liquid $N_2$ immersion; and (iii.) spray-freezing. The PSD of the adjuvant particles for samples frozen utilizing the slowest cooling rate, 0.5° C./min, is shown in FIG. 2.

FIG. 2 shows particle size distribution of 0.2% Alhydrogel™ following (A.) freezing and thawing and (B.) freeze-drying and reconstitution in 25 mM sodium succinate, pH 4.0 with varying trehalose weight/volume concentrations of 0, 2, 4, 6, 7.5, 10, and 15%. Samples were frozen on a lyophilizer shelf at 0.5° C./min. Each data set is a composite of three runs, each utilizing three individual samples.

Samples frozen and thawed in low concentrations of trehalose (<4 w/v %) result in aggregation of the Alhydrogel™ particles to a size one order of magnitude greater than that of the stock adjuvant. Samples freeze-thawed with trehalose concentrations in the range of 5-10 w/v % result in two populations of particles after freeze-thawing: one remaining at the size of the Alhydrogel™ particles seen before lyophilization, and a second, aggregated population with a size about an order of magnitude larger than that of the starting material. Samples freeze-thawed in high concentrations of trehalose (>10 w/v %) result in minimal aggregation and retain a PSD nearly identical to that of the stock formulation. For dried samples, the PSD measured after reconstitution shows that Alhydrogel™ is nearly entirely aggregated at trehalose concentrations below 10 w/v %. At higher trehalose concentrations, a bimodal PSD is observed composed of aggregates with a mean size of 10 μm and unaggregated particles with a mean size centered around 1 μm.

Figure 5:
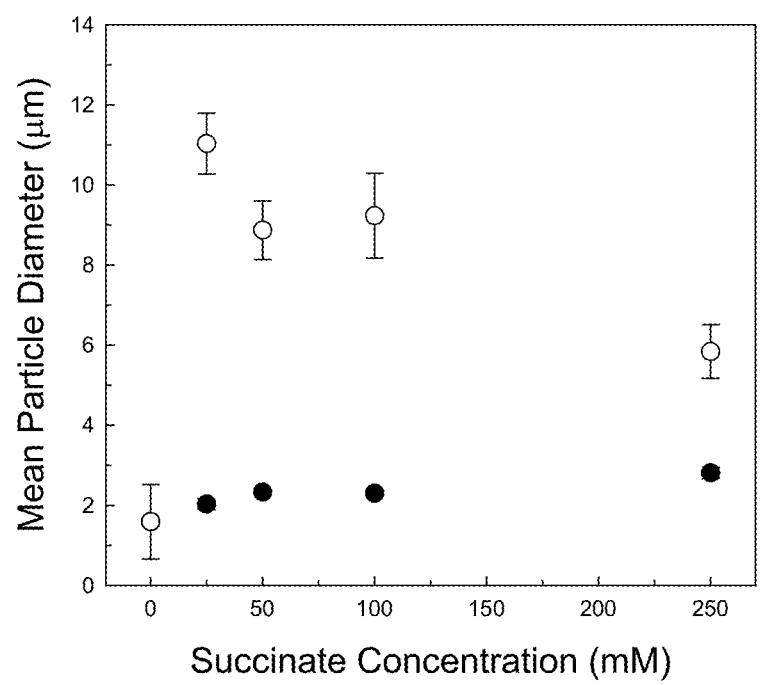
FIG. 5 shows mean particle diameter of 0.2% Alhydrogel™ after processing in 7.5 w/v trehalose at varying sodium succinate concentrations either frozen and thawed immediately (●) or lyophilized and reconstituted (○).

PSD of Processed Aluminum Hydroxide Adjuvant Suspensions—Effect of Buffer Salt Concentration The effect of sodium succinate concentration on the PSD is shown in FIG. 5.

FIG. 5 shows mean particle diameter of 0.2% Alhydrogel™ after processing in 7.5% w/v trehalose at varying sodium succinate concentrations, pH 4.0. Samples were cooled at 0.5° C./min on the lyophilizer shelf and were either thawed immediately (●) or dried and reconstituted (○).

Increasing succinate concentrations from 0 mM to 250 mM results is only a small increase in the PSD of the adjuvant particles. However, for the dried and reconstituted samples, there is a large increase in the PSD between samples formulated at 0 mM succinate and 25 mM succinate. Samples freeze-dried and reconstituted in the absence of succinate show only minimal aggregation. However, in samples freeze-dried and reconstituted containing sodium succinate, the particles are mostly aggregated.

PSD of Processed Aluminum Hydroxide Adjuvant Suspensions—Effect of Cooling Rate

The effect of cooling rate on the Alhydrogel™ mean particle diameter while varying trehalose is shown in FIG. 3.

FIG. 3 shows the surface area weighted mean particle diameter of 0.2% Alhydrogel™ after processing in 25 mM sodium succinate (pH 4.0) as a function of trehalose concentration and processing. Samples were cooled at various rates to a frozen solid: (○) tray frozen at 0.5° C./min, (□) frozen by immersion of bottom of vial in liquid nitrogen, and (Δ) spray-frozen. Solid markers indicate samples following freeze-drying and reconstitution, open markers frozen and thawed. Solid and dashed lines indicate unprocessed Alhydrogel™+/−standard deviation respectively.

As expected, the particle size distribution is highly dependant on the cooling rate at which the solution is frozen. PSD's for spray-frozen and thawed samples remained identical to stock Alhydrogel™ (mean particle diameter 2.25±0.37 μm), even in the absence of trehalose, while spray-freeze-dried samples required addition of 5 w/v % trehalose in order to retain the original stock PSD. However, the slower the cooling rate of the solution to the frozen state, the higher the trehalose concentration that is required to maintain the original PSD. In addition, the drying and/or reconstitution of the samples results in further aggregation of the adjuvant, even though it appears that a significant fraction of the aggregation is observed during the freezing stage of lyophilization.

Figure 4:
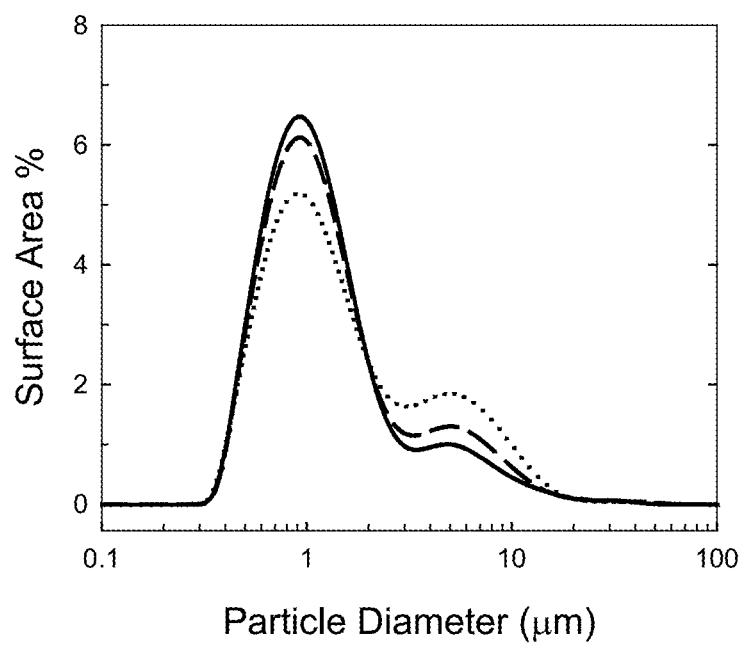
FIG. 4 shows particle size distribution of 0.2% Alhydrogel™ following freezing and thawing varying the temperature at which the samples are thawed.

Because the cooling rate of samples to a frozen state had an affect on the PSD of the adjuvant particles in solution, the temperature at which these samples were thawed was hypothesized to also have an affect by a similar mechanism. FIG. 4 shows the thawing temperature-dependency on samples containing 7.5 w/v % trehalose in 25 mM sodium succinate.

FIG. 4 shows particle size distribution of 0.2% Alhydrogel™ following freezing and thawing varying the temperature at which the samples are thawed. Samples formulated in 7.5 w/v % trehalose, 25 mM sodium succinate, pH 4.0 were tray frozen at a ramp rate of 0.5° C./min and were thawed in a 37° C. water bath (solid line), at room temperature (dashed line) and at 4° C. in a refrigerator.

There is a correlation between this temperature and the resulting PSD, as samples thawed at the highest temperature (and thus fastest warming rate) had a larger percentage of the aggregate population than samples thawed at lower temperatures.

Zeta Potential of Processed Aluminum Hydroxide Adjuvant

The zeta potential of Alhydrogel™ particles following freeze-drying and spray freeze-drying was examined. Samples were formulated in 7.5 w/v % trehalose, 25 mM sodium succinate, pH 4.0. The zeta potential measured after reconstitution for the two processes is presented in FIG. 6 along with that of the liquid control.

Figure 6:
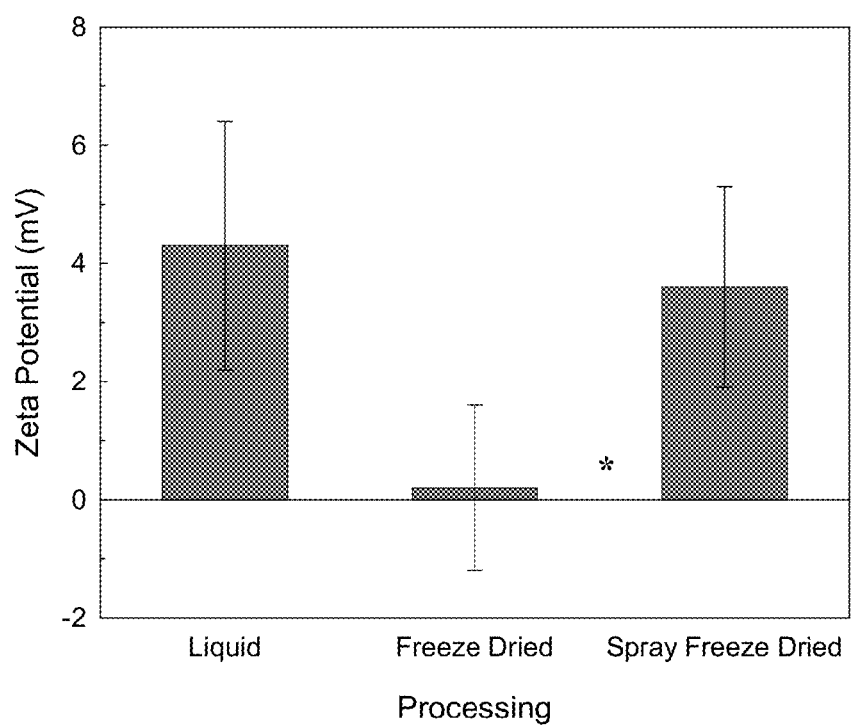
FIG. 6 shows zeta potential of Alhydrogel™ as a function of processing.

FIG. 6 shows zeta potential of Alhydrogel™ as a function of processing. All formulations were in 7.5% trehalose, 25 mM sodium succinate, pH 4.0. Freeze-dried formulations were cooled at −0.5° C./min to freezing while spray-freeze-dried formulations were dropped into liquid nitrogen. * Indicates sample statistical difference from the liquid control at p of 0.05.

The zeta potential for the liquid sample is a slightly positive value (4.3±2.1 mV). This value is lower than that measured previously in similarly prepared samples without succinate (around 18 mV). Samples that are lyophilized using the slowest cooling rate result in a significant drop in zeta potential to nearly zero. However, samples that were spray-freeze-dried retain the zeta potential of the pre-processed formulation.

Figure 7:
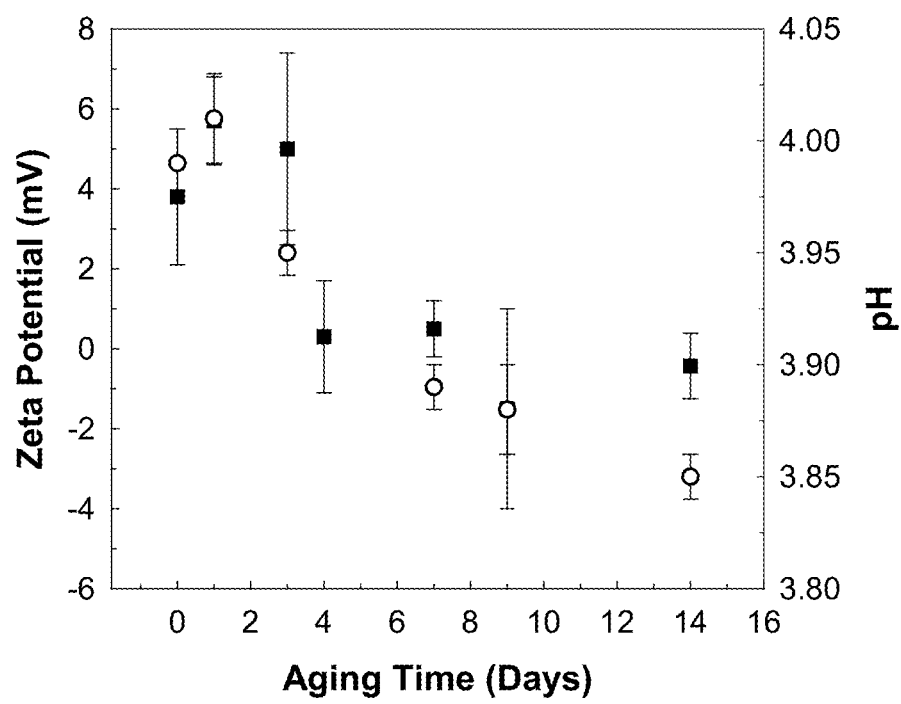
FIG. 7 shows zeta potential (■) and pH (○) of Alhydrogel™ particles as a function of time since formulation when stored at 4° C.

The drop in zeta potential for the lyophilized sample led to an aging study for the adjuvant while incubated at 4° C. in 7.5% trehalose, 25 mM sodium succinate, pH 4.0. FIG. 7 depicts the average zeta potential and pH of five individual samples during incubation.

FIG. 7 shows zeta potential (■) and pH (○) of Alhydrogel™ particles aged in 7.5 w/v % trehalose, 25 mM sodium succinate, pH 4.0 as a function of time since formulation. Samples were stored at 4° C.

The zeta potential drops significantly during the first three days of incubation and is mirrored by a slight drop in the pH of the solution. The drop in zeta potential is similar to the same drop in zeta potential for the lyophilized samples.

XRPD of Dried Samples

Figure 8:
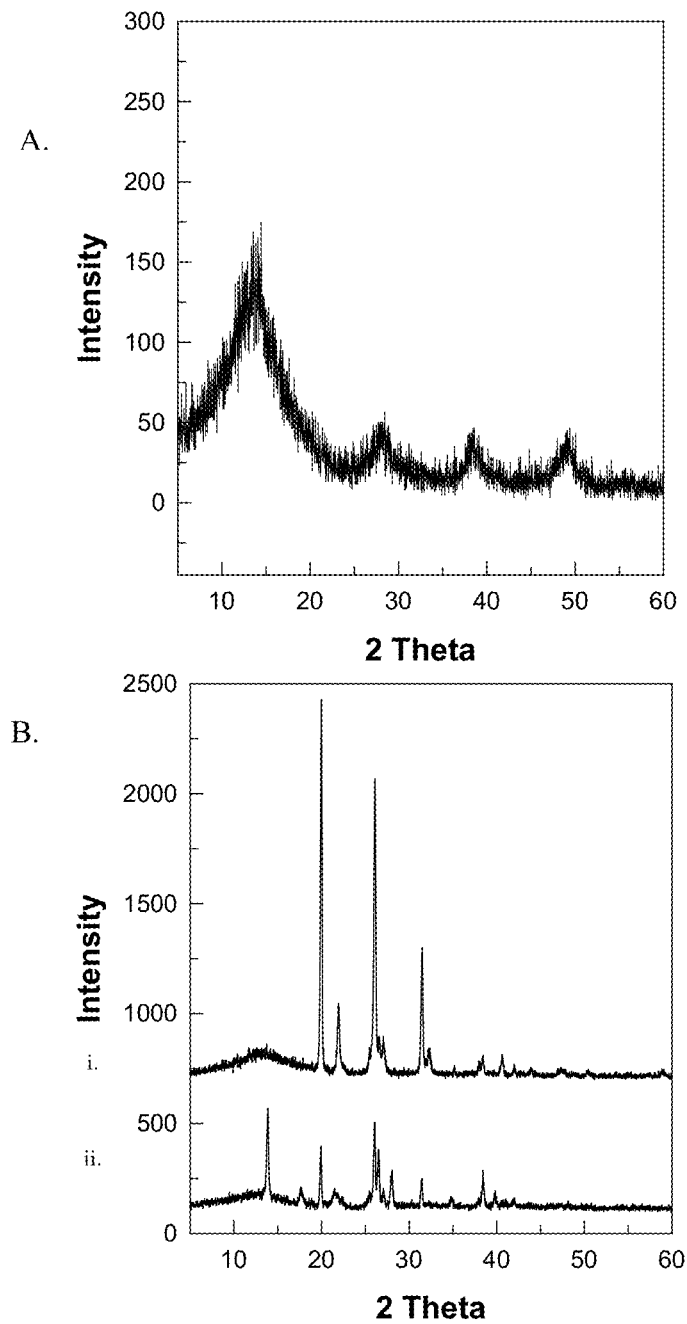
FIG. 8 shows x-ray powder diffractograms of A.) freeze-dried Alhydrogel™ and B.) (i.) freeze-dried succinic acid and (ii.) freeze-dried sodium succinate, pH 4.0.

X-ray powder diffraction was utilized to characterize the dried state of the lyophilized samples. FIG. 8A depicts the XRPD pattern for a lyophilized Alhydrogel™ sample, which is in close agreement with those reported in the literature (Johnston C T, Wang S L, Hem S L 2002. Measuring the surface area of aluminum hydroxide adjuvant. J Pharm Sci 91(7):1702-1706; Burrell L S, Lindblad E B, White J L, Hem S L 1999. Stability of aluminium-containing adjuvants to autoclaving. Vaccine 17(20-21):2599-2603.). FIG. 8B depicts the XRPD of lyophilized samples of succinic acid (i.) and sodium succinate, pH 4.0 (ii.).

Succinic acid has strong peaks at 2θ values of 20.0, 22.0, 26.1, and 31.5°, while the sodium succinate formulated at pH 4 and lyophilized retains these peaks, although much lower in intensity, and also has an additional strong peak at 2θ=13.9°. The peaks at 20.0, 26.1, and 31.5° for the buffer, therefore, are most likely due to the succinic acid and the peak appearing at 13.9° is most likely due to monobasic sodium succinate (or a hydrate), since the acid and monobasic salt should be the most prevalent species at pH 4.

Lyophilized samples containing trehalose and succinate at varying compositions were examined by XRPD with and without Alhydrogel™ particles.

Figure 9:
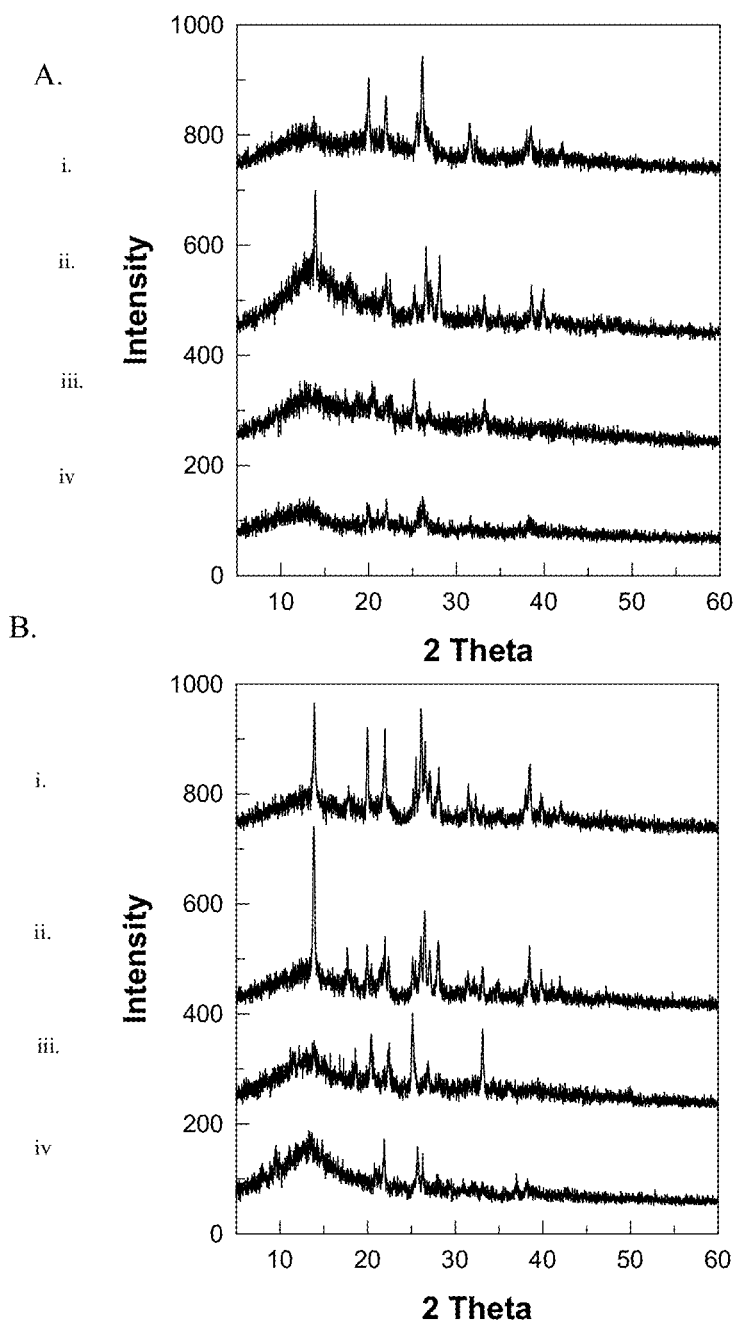
FIG. 9 shows x-ray powder diffractograms of dried mixtures of succinate, trehalose, and Alhydrogel™ varying freezing rates and the succinate to trehalose mass ratio.

FIG. 9 shows x-ray powder diffractograms of dried mixtures of succinate, trehalose, and Alhydrogel™ varying freezing rates and solution formulation for a succinate to trehalose mass ratio of A.) 0.79 and B.) 2.95. From top to bottom, the diffractograms are for i.) freeze-dried sodium succinate, ii.) freeze-dried sodium succinate with Alhydrogel™, iii.) spray-freeze-dried sodium succinate with Alhydrogel™, and iv.) freeze-dried potassium succinate with Alhydrogel™. All solutions were at pH 4.0. Samples containing Alhydrogel™ were at a concentration of 0.2 w/v %.

The samples with a succinate-trehalose mass ratio of 0.79 (FIG. 9A) were lyophilized in 500 mM succinate and 7.5 w/v % trehalose. The samples with a succinate-trehalose mass ratio of 2.95 (FIG. 9B) were lyophilized in 250 mM succinate, 1 w/v % trehalose. The high concentrations of succinate, compared to that at which previous samples were prepared, was necessary to be able to observe crystalline components of succinate. Samples were lyophilized with or without 0.2 w/v % Alhydrogel™ at pH 4.0 utilizing two cooling rates—either tray frozen at 0.5° C./min or spray-frozen. Samples tray-frozen were also made using potassium succinate instead of sodium succinate to examine the effect of changing the buffer cation.

In samples without adjuvant at low mass ratios of succinate to trehalose, the crystalline pattern matches that of succinic acid in the absence of Alhydrogel™. Once the adjuvant particles are added, the spectrum shifts to that of the sodium succinate species as evidenced by the appearance of a peak at 2θ=13.9°. When this same solution is spray freeze-dried, only low levels of crystallinity are observed. Switching from sodium to potassium also reduces the crystallinity of the freeze-dried samples. For higher succinate to trehalose ratios, the crystalline pattern observed in the presence and absence of Alhydrogel™ appears to be that of a mixture of succinic acid and the monobasic sodium succinate species. Similar to the previous samples, spray freeze-drying and switching to potassium salts reduces the overall crystallinity and limits the monobasic salt crystallization.

Figure 10:
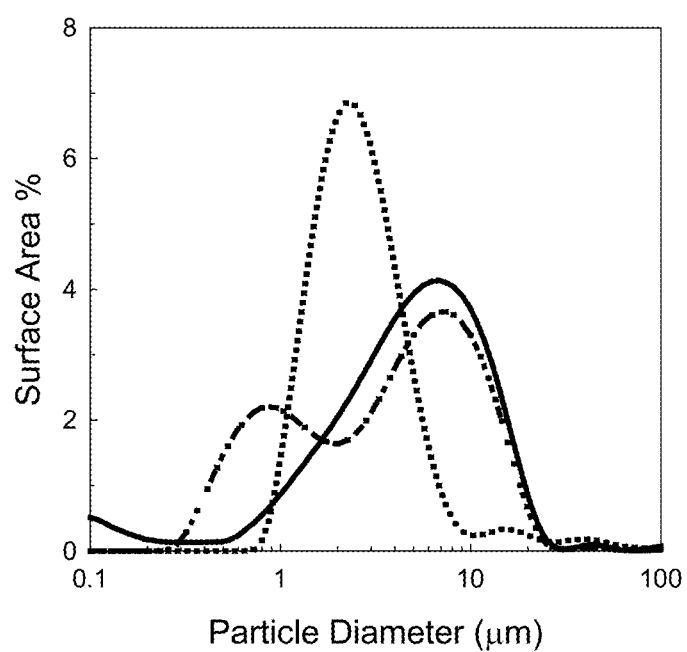
FIG. 10 shows particle size distribution of samples from FIG. 9B.

The PSD of samples at the higher succinate:trehalose mass fraction is shown in FIG. 10 after samples were reconstituted with water.

FIG. 10 shows particle size distribution of samples from FIG. 9B. Solid line: freeze-dried sodium succinate/trehalose with Alhydrogel™; dashed line: freeze-dried potassium succinate/trehalose with Alhydrogel™; dotted Line: spray freeze-dried sodium succinate:trehalose with Alhydrogel™. All samples were buffered to pH 4.0 prior to lyophilization and had a succinate:trehalose mass ratio of 0.79. Alhydrogel™ was at a concentration of 0.2 w/v % for all samples.

The PSD of the freeze-dried sodium succinate/trehalose mixture with Alhydrogel™ reflected mostly aggregated adjuvant. The samples lyophilized with potassium succinate had a reduction in the overall aggregation of the adjuvant particles. Samples spray freeze-dried with sodium succinate appeared mostly unaggregated.

Example 2

Immune Response to Lysozyme Vaccines containing Aluminum Salt Adjuvants Following Freeze-Thawing and Freeze-Drying Materials Trehalose dehydrate (high purity, low endotoxin) was obtained from Ferro Pfanstiehl (Cleveland, Ohio). Succinic acid was purchased from Sigma Chemical Company (St. Louis, Mo.). Alhydrogel™ 2.0% (aluminum hydroxide adjuvant) and Adju-phos™ 2.0% (aluminum phosphate adjuvant), made by Brenntag Biosector, were purchased through E. M. Sergeant Pulp & Chemical Co, Inc (Clifton, N.J.). Lysozyme was obtained from Seikagaku Corporation (Japan). 3-ml and 5-ml lyophilization vials and caps were obtained from West Pharmaceutical Services.

Sample Preparation

Lysozyme was prepared as a 1 mg/ml solution. Endotoxins were removed using Detoxi-Gel AffinityPak Prepacked Columns from Pierce (Rockfort, Ill.). The lysozyme was then dialyzed to 25 mM sodium succinate, pH 4 using Slyde-a-Lyzer Dialysis Cassettes (10k MWCO) from Pierce (Rockfort, Ill.). After filtration through a 0.2 µm filter for sterilization, concentration was determined by UV absorbance. For preparing samples for injection, all aqueous solutions are passed through a 0.2 µm filter prior to formulation with the exception of the adjuvants, which are purchased sterile.

Lyophilization

A FTS Systems Lyostar lyophilizer was used for the freeze-drying of samples. Samples were frozen at various cooling rates as follows from slowest to fastest: (i.) Frozen by placing the samples in lyophilizer, equilibrating 1 hr at a shelf temperature of 0° C., then cooling the shelves at 0.5° C./min to −40° C. ("tray-freezing"); and (ii.) Spray-freezing by dropping by ~20 µl droplets into liquid $N_2$. Tray-frozen samples were processed in 3-ml lyophilization vials, while the spray-frozen samples were processed in 5-ml lyophilization vials. Spray-frozen formulations were quickly transferred to the lyophilizer placed on lyophilizer shelves pre-cooled to −40° C. Samples were spaced in the lyophilizer so that they were each separated from one another and were encircled with a row of vials containing water.

Primary drying of the samples was achieved by setting the shelf temperature to −20° C. and applying a vacuum at 60 mTorr for 20 hours, and was followed by secondary drying, in which shelf temperatures were ramped from −20° C. to 0° C. at 0.2° C./min, to 30° C. at 0.5° C./min and finally held at 30° C. for 5 hours. Samples were sealed under vacuum and reconstituted with DI water prior to analysis. Freeze-thaw samples were thawed at laboratory temperature (21° C.+/−2° C.) after freezing.

Particle Size Distributions

Particle size distributions (PSDs) were measured using a Beckman-Coulter LS230 laser diffraction particle size analyzer. Three one-ml samples were required for each run, and three replicates of each run were completed per formulation. Reported PSDs are surface area weighted and are composites of three runs.

Mice Immunization and Serum Collection

Male and female (3 each) 5-7 week old BALB/c mice (Jackson Laboratories) were used to asses the immunogenicity of liquid, freeze-thaw and freeze-dried vaccines of aluminum hydroxide- and aluminum phosphate-formulated lysozyme vaccines. Prior to the day of injection, liquid formulations were prepared, freeze-thaw vaccines were thawed, and lyophilized preparations were reconstituted with water. Injections were administered subcutaneously along the back with 100 microliter of the formulation containing 1 microgram of lysozyme. Control mice were injected with unprocessed buffer or with unprocessed lysozyme in buffer without adjuvant. A booster immunization was administered on day 14. Blood was collected via retro-orbital bleeding under anesthesia prior to each injection and 14 days following the booster immunization. Serum was separated by centrifugation at 12,500 rpm for 5 minutes, transferred to a clean centrifuge tube, and frozen at −80° C. until analysis.

Enzyme-Linked Immunosorbent Assay (ELISA)

The antibody response to each lysozyme vaccine was determined by ELISA. 96-well plates (Nunc, Rochester, N.Y.) were coated with 0.5 microgram per well of lysozyme in 50 mM sodium bicarbonate pH 9.6 overnight at 4° C. Plates were washed five times with phosphate-buffered saline (PBS), pH 7.4. Blocking of nonspecific sites was done using 1% bovine serum albumin (Fisher) by filling each well with blocking buffer and immediately emptying three times. Plates were allowed to dry and were stored at 4° C. until use. For running ELISAs, serum samples were thawed at room temperature and were serially diluted in 1% BSA in PBS from 1:50 to 1:3200 dilution, and 50 µl of each samples was added to the 96 well plate. Samples were incubated overnight at 4° C. After washing 5 times with PBS, plates were incubated with 50 µl horseradish peroxidase-conjugated goat-anti-mouse antibodies for IgG1, IgG2a or IgE (Immunology Consultants Lab, Inc, Newberg, Oreg.) at 1:10,000 dilution for 2 hours at room temperature with rotation (400 rpm). Plates were then washed, and incubated with 100 µl of Ultra-TMB (Pierce, Rockfort, Ill.). After 20 minutes of development, plates were stopped with 100 µl of 1 N HCl. Plates were read at an absorbance of 450 nm using a ThermoMax microplate reader (Molecular Devices, Sunnyvale, Calif.).

Results

Figure 12:
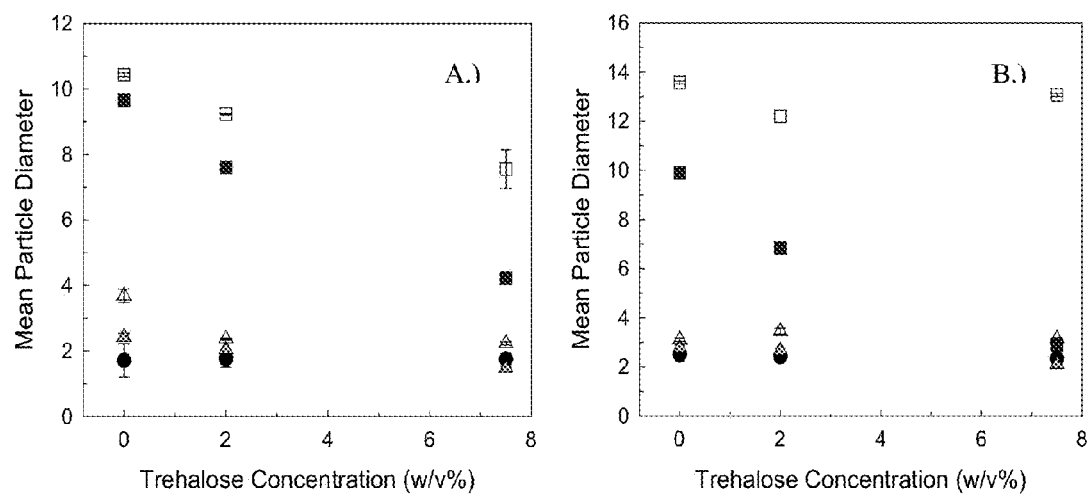
FIG. 12 shows mean particle diameter of A.) Alhydrogel™, and B.) Adju-phos™ formulations following processing.

It is generally theorized that the smaller the particle size of the vaccine adjuvant, the more immunogenic the vaccine preparation (Maa et al., 2003) Different processing parameters and formulation variables were utilized in order to obtain a wide range of PSD for sample vaccines to test this hypothesis. FIG. 12 shows mean particle diameter of A.) Alhydrogel™, and B.) Adju-phos™ following processing. Samples were either processed as a liquid (○) or were frozen by spraying into liquid nitrogen (∆) or tray freezing (□). Solid markers indicate freeze-thaw samples while open signals represent freeze-dried and reconstituted samples.

The mean adjuvant particle diameter for processed samples is presented in FIG. 12A for samples containing Alhydrogel™ and in FIG. 12B for samples containing Adju-phos™. The particle size distribution for the two adjuvants follows similar trends, in which aggregation can be avoided by faster cooling rates and high concentration of trehalose.

Mice were immunized with lysozyme vaccines following processing as shown above. ELISA was used to quantify the IgG1 antibodies in each serum sample following two injections of the vaccine. The absorbance at 1:100 dilution of serum gave a good distribution of antibody responses and was used to examine the responses of each individual mouse. The response for each mouse is shown in FIG. 13 for Alhydrogel™ vaccines and FIG. 14 for Adju-phos™ vaccines.

Figure 13:
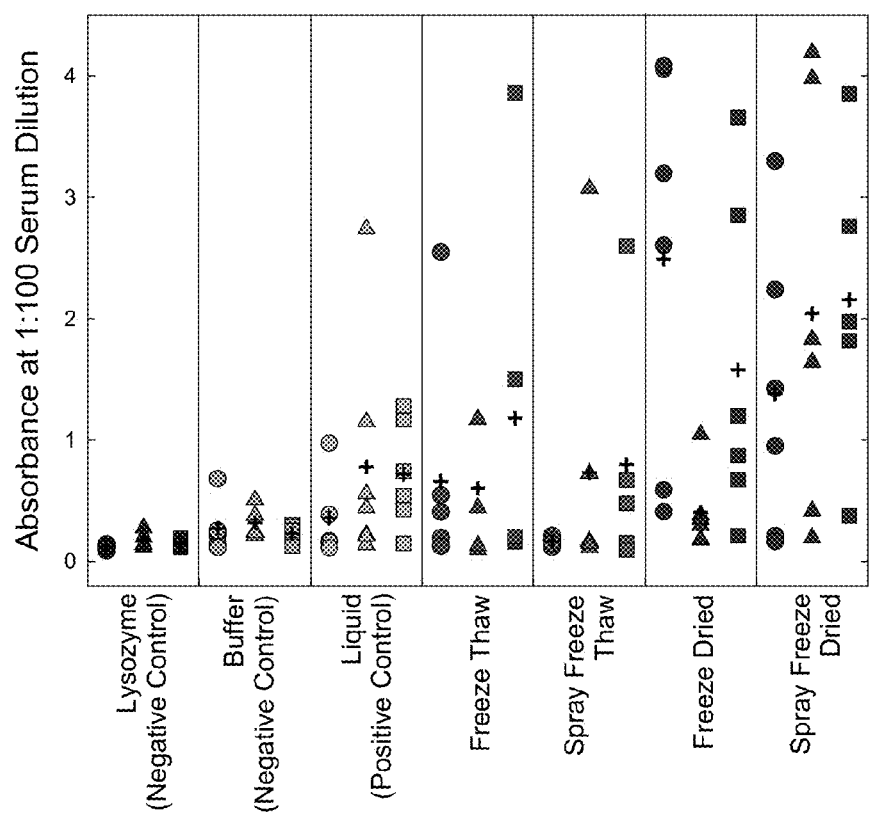
FIG. 13 shows ELISA readings at 1:100 dilution of serum after two injections of differently-processed lysozyme vaccines containing Alhydrogel™ adjuvant. Serum samples were analyzed for IgG1 antibodies specific for lysozyme. Samples were either processed in 0 w/v % (●), 2 w/v % (▲), or 7.5 w/v % (■) trehalose.

FIG. 13 shows ELISA readings at 1:100 dilution of serum after two injections of differently-processed lysozyme vaccines containing Alhydrogel™ adjuvant. Serum samples were analyzed for IgG1 antibodies specific for lysozyme. Samples were either processed in 0 w/v % (●), 2 w/v % (▲), or 7.5 w/v % (■) trehalose. Plus symbols indicate the geometric mean from six mice.

Figure 14:
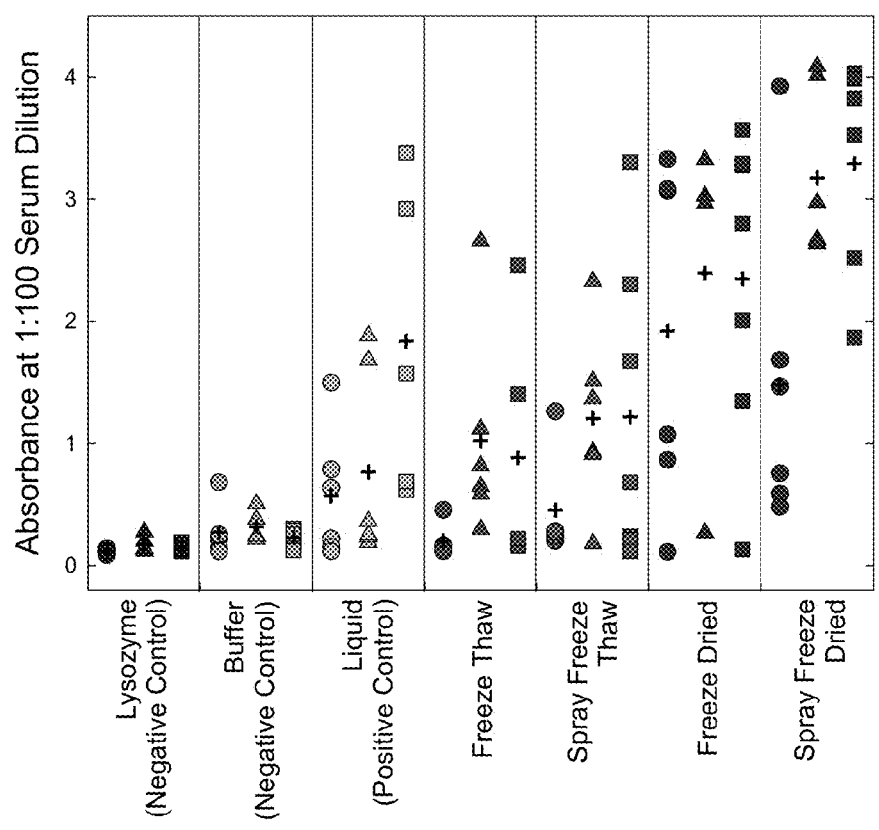
FIG. 14 shows ELISA absorbance readings at 1:100 dilution of serum after two injections of differently-processed lysozyme vaccines containing Adju-phos™ adjuvant. Serum samples were analyzed for IgG1 antibodies specific for lysozyme. Samples were either processed in 0 w/v % (●), 2 w/v % (▲), or 7.5 w/v % (■) trehalose.

FIG. 14 shows ELISA absorbance readings at 1:100 dilution of serum after two injections of differently-processed lysozyme vaccines containing Adju-phos™ adjuvant. Serum samples were analyzed for IgG1 antibodies specific for lysozyme. Samples were either processed in 0 w/v % (●), 2 w/v % (▲), or 7.5 w/v % (■) trehalose. Plus symbols indicate the geometric mean from six mice.

The two negative controls (buffer and lysozyme in buffer) show only background response. The liquid vaccine with both cases, used as a positive control as it was expected that this would have the highest response of all the vaccines, gave only a moderate response. Freeze-thaw samples utilizing both cooling rates gave responses similar to that of the liquid control. However, the dried formulations appear to give the highest response of all the vaccines in terms of having the most mice with the highest absorbance reading (~4 AU) and the least amount of non-responders with responses similar to that of the negative control. These trends are similar for both adjuvants. No significant amounts of IgG2 or IgE antibodies were detected. The immunological response of the processed vaccines was compared to the mean particle diameter following processing for all of the adjuvanted samples as shown in FIG. 15.

Figure 15:
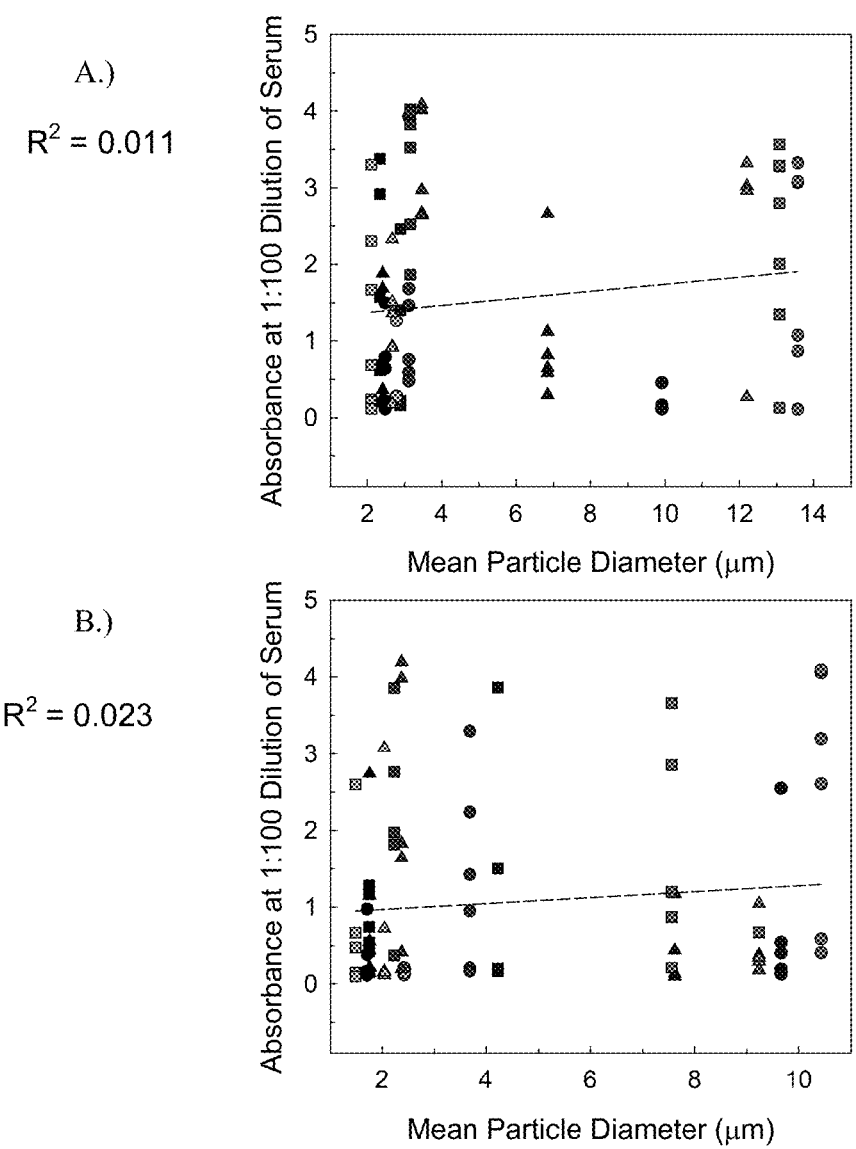
FIG. 15 shows ELISA absorbance readings versus mean particle diameter for lysozyme vaccines with A.) Alhydrogel™ and B.) Adju-phos™ adjuvant. Samples were either processed in 0 w/v % (●), 2 w/v % (▲), or 7.5 w/v % (■) trehalose.

FIG. 15 shows ELISA absorbance readings versus mean particle diameter for lysozyme vaccines with A.) Alhydrogel™ and B.) Adju-phos™ adjuvant. Samples were either processed in 0 w/v % (●), 2 w/v % (▲), or 7.5 w/v % (■) trehalose. Plus symbols indicate the geometric mean from six mice. Unlike what was previously predicted in the art (Maa et al., 2003 and Diminsky et al., 1999), there was no significant correlation between the PSD and the IgG1 response in this experiment.

Example 3

Immune Response to Botulinum Neurotoxin C Vaccines containing Aluminum Salt Adjuvants Following Freeze-Thawing and Freeze-Drying Materials were as described in Example 2.

Efficacy Study of BotC Vaccine

Vaccines were prepared using rBotNTC(Hc) the sequence of which is shown in FIG. 11 (SEQ ID NO: 2), a recombinant protein antigen to *C. botulinum* neurotoxin C. Samples were freeze dried or spray freeze dried in 15% w/v % trehalose, 25 mM sodium succinate, pH 4.0 at a protein concentration of 150 µg/ml bound to 0.2 w/v % Alhydrogel. A liquid formulation of the same composition was prepared as a control. Samples that were freeze-dried and spray freeze-dried exhibited mostly unaggregated adjuvant PSD for both dried formulations.

The efficacy study was conducted by the US ARMY. Dried samples were reconstituted with 0.9 ml water prior to dilution. After reconstitution, samples concentrations were adjusted to 81 µg/ml rBotNTC(Hc) in 25 mM sodium succinate, 15 mM sodium phosphate, 8% trehalose, pH 5. Samples were diluted to a range of antigen doses from 0.011 µg/mouse to 8.1 µg/mouse. Ten CD-1 (Female) mice were injected with 100 µl of antigen at each dose. Mice were then challenged with BoNT C three weeks after the second injection. ED50 levels were then calculated.

Figure 16:
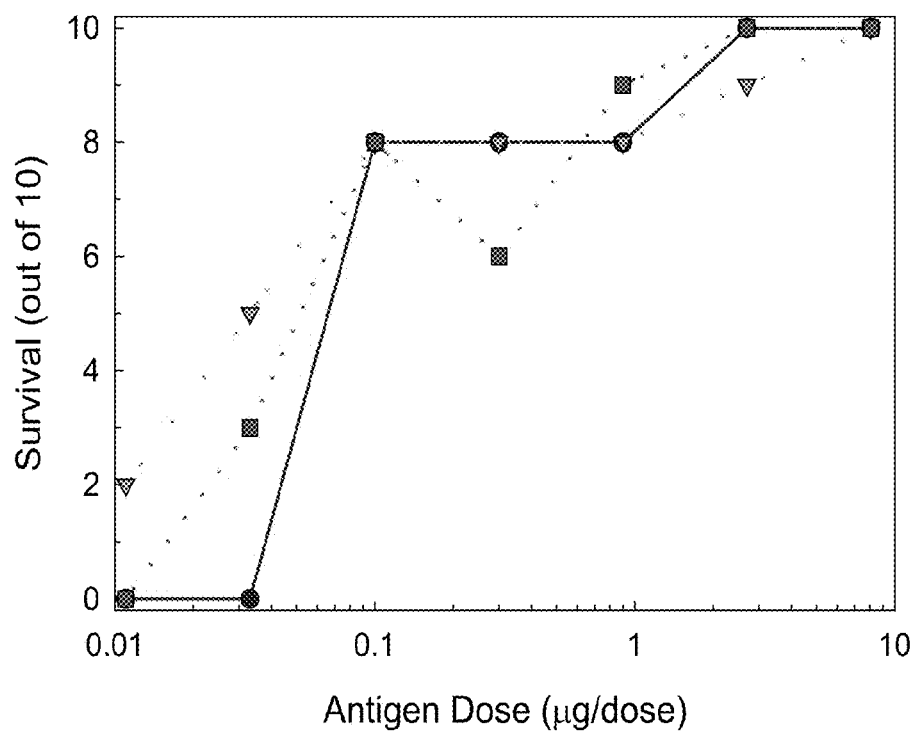
FIG. 16 shows an efficacy study in CD-1 mice of freeze-dried (●), spray freeze-dried (▼), and liquid (■) formulated rBoNTC(Hc) vaccine. Ten mice were immunized with each dose of vaccine.

The results from survival upon challenge efficacy study are shown in FIG. 16 with the calculated ED50 values shown in Table 1. FIG. 16 shows an efficacy study in CD-1 mice of freeze-dried (●), spray freeze-dried (▼), and liquid (■) formulated rBoNTC(Hc) vaccine. Ten mice were immunized with each dose of vaccine.

There was no significant difference in the efficacy of the three vaccines from liquid, freeze-dried or spray freeze-dried preparations with 15% w/v trehalose.

TABLE 1

Efficacy of *Botulinum* Neurotoxin C Vaccines containing Aluminum Salt Adjuvants Following Freeze-Thawing and Freeze-Drying.

| antigen dose | (1) Bot-C-73-1 (FD) | (2) Bot-C-73-2 (SFD) | (3) Bot-C-73-3 (LIQ) |
|---|---|---|---|
| 8.1 µg/mouse | 10/10 | 10/10 | 10/10 |
| 2.7 µg/mouse | 10/10 | 9/10 | 10/10 |
| 0.9 µg/mouse | 8/10 | 8/10 | 9/10 |

TABLE 1-continued

Efficacy of *Botulinum* Neurotoxin C Vaccines containing Aluminum
Salt Adjuvants Following Freeze-Thawing and Freeze-Drying.

| antigen dose | (1) Bot-C-73-1 (FD) | (2) Bot-C-73-2 (SFD) | (3) Bot-C-73-3 (LIQ) |
|---|---|---|---|
| 0.3 µg/mouse | 8/10 | 8/10 | 6/10 |
| 0.1 µg/mouse | 8/10 | 8/10 | 8/10 |
| 0.033 µg/mouse | 0/10 | 5/10 | 3/10 |
| 0.011 µg/mouse | 0/10 | 2/10 | 0/10 |
| $ED_{50}$: | 120 ng | 41 ng | 90 ng |
| 95% conf limits: | 13-534 ng | 74-105 ng | 42-171 ng |

Example 4

Immune Response to Botulinum Neurotoxin E
Vaccines Containing Aluminum Salt Adjuvants
Following Freeze-Thawing and Freeze-Drying
Preparation of Recombinant Botulinum Type E
Vaccines Liquid Botulinum vaccines were prepared with recombinant botulinum type E vaccine (rBoNTE), the sequence of which is shown in FIG. 11 (SEQ ID NO: 1), at a concentration of 81 micrograms/ml. Liquid formulations consisted of 25 mM sodium succinate, 15 mM sodium phosphate, 0.2% Alhydrogel™ in either 0 or 10 w/v % trehalose at pH 5.0. Lyophilized vaccines were lyophilized in 25 mM sodium succinate, 10 w/v % trehalose at pH 4.0 with and without 0.2% Alhydrogel™.

Two lyophilized preparations were prepared: tray frozen in which the samples were placed on a pre-cooled shelf at −40° C. after an equilibration at 4° C. and spray frozen in which the formulation was dropped into liquid nitrogen at a volume of approximately 20 microliters a drop. Primary drying of all samples was achieved by setting the shelf temperature to −20° C. and applying a vacuum at 60 mTorr for 20 hours, and was followed by secondary drying, in which shelf temperatures were ramped from −20° C. to 0° C. at 0.2° C./min, to 30° C. at 0.5° C./min and finally held at 30° C. for 5 hours.

Lyophilized samples were reconstituted to 25 mM sodium succinate, 15 mM sodium phosphate, 0.2% Alhydrogel™, 10 w/v % trehalose, pH 5.0 with the addition of a phosphate buffer, pH 10.8 prior to use.

Immunological Study:

Female, 6 week old CD-1 mice (Charles River Laboratories) were used to test the immunological response to the rBoNTE vaccines. Sera (200 microliter/mouse) was collected from each mouse from the retro-orbital venous sinus. Six mice per group were immunized subcutaneously along the back with 8.1 microgram each of the vaccine (100 microliter) or a negative control consisting of the components of the liquid vaccine without the protein antigen. Two weeks later, sera was collected again for testing of a primary response and each mouse was injected again with the same vaccine as the first injection. Final sera was collected two weeks after the booster injection.

Enzyme Linked Immunosorbant Assay (ELISA):

ELISA was used to test for rBoNTE-specific antibody response in each mouse sera. 0.25 microgram of rBoNTE in 50 mM sodium bicarbonate buffer, pH 9.6 was plated in each well of a 96 well plate (Nunc) and incubated at 4° C. overnight. Plates were washed with phosphate buffered solution (PBS) and blocked with blocking buffer consisting of 1% bovine serum albumin (BSA) (Sigma) in PBS. Sera was serially diluted in blocking buffer up to a dilution factor of 3.5× $10^6$ by ⅓ increments with the first dilution factor of 0.05. 50 microliter of each dilution was incubated in each well overnight at 4° C. Plates were then incubated with 50 ml of an HRP-conjugated IgG1 goat-anti-mouse antibody (Immunology Consultants Lab, Inc.) at a concentration of 0.1 microgram/ml for 2 hours with rotation. Plates were developed with 100 microliter per well of 1-Step Ultra TMB Substrate (Pierce) for 15 minutes, stopped with 100 microliter per well of 1N NaOH and then read immediately on a microplate reader at 450 nm. Titers were calculated as the dilution factor which gave an absorbance reading of 0.5 absorbance units by interpolation of the absorbance readings vs. dilution factor curves for each sera. The value of 0.5 is the approximate value of the averages of the negative controls plus two standard deviations.

Figure 17:
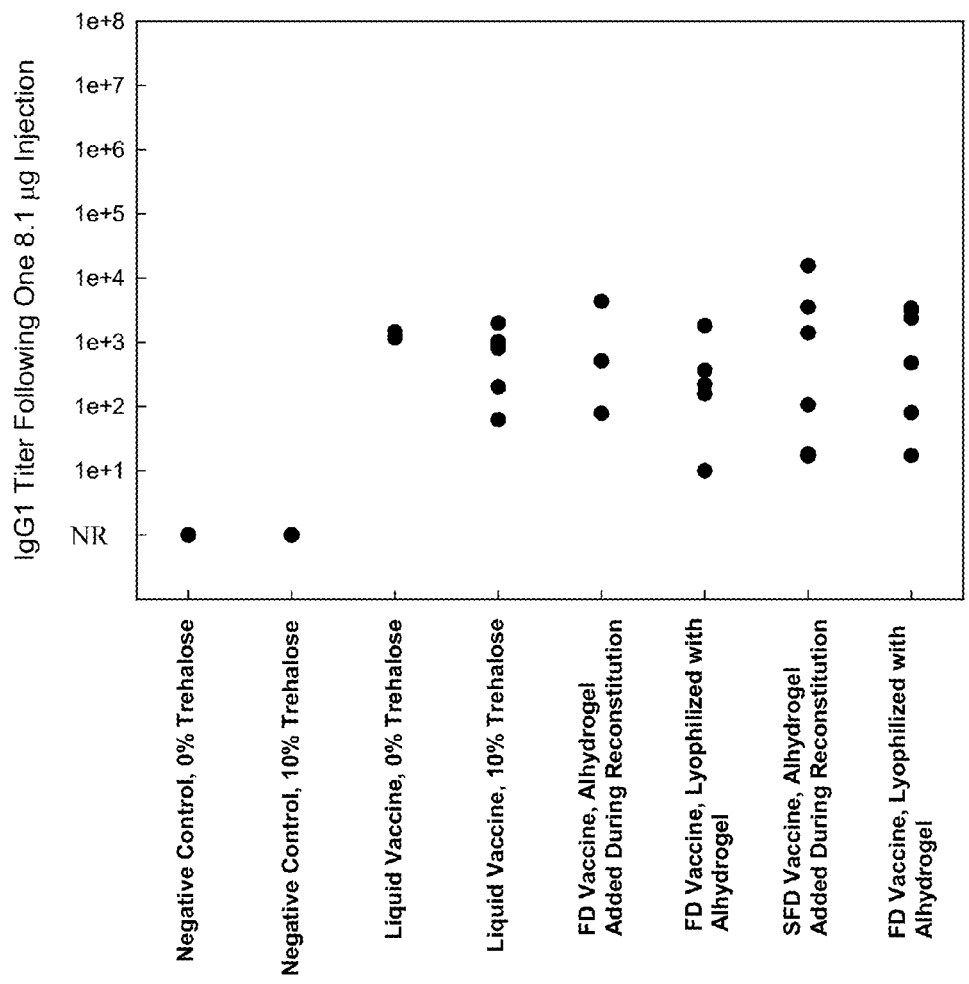
FIG. 17 shows primary IgG1 response specific for rBoNTE in mice after immunization with a single injection of vaccines comprising 8.1 μg rBoNTE after two weeks.
Figure 18:
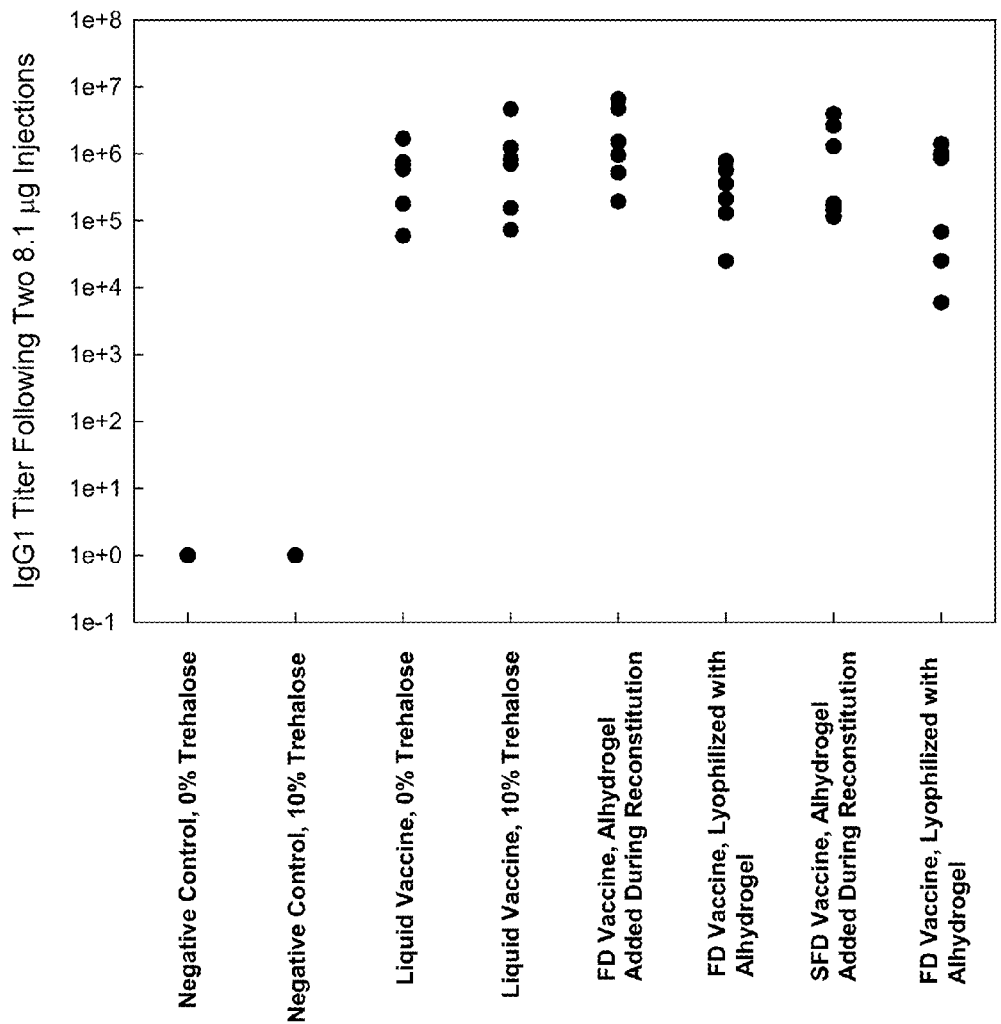
FIG. 18 shows the secondary IgG1 response specific for rBoNTE in mice immunized with vaccines comprising 8.1 μg rBoNTE per injection two weeks following the booster injection.

At the onset of the rBoNTE stability study, there was no significant difference between any of the different formulations in terms of rBoNTE-specific antibodies following one injection (FIG. 17) or after two injections (FIG. 18).

FIG. 17 shows primary IgG1 response specific for rBoNTE in mice after immunization with a single injection of vaccines comprising 8.1 µg rBoNTE after two weeks. "NR" indicates mice with an insignificant rBoNTE-specific response. "FD" indicates freeze-dried.

FIG. 18 shows the secondary IgG1 response specific for rBoNTE in mice immunized with vaccines comprising 8.1 µg rBoNTE per injection two weeks following the booster injection. "NR" indicates mice with an insignificant rBoNTE-specific response.

For all cases, there was a dramatic increase in the antibody production specific to the rBoNTE antigen following two injections resulting in an increase in titer over two orders of magnitude.

The present disclosure has generally been described in relation to a method of preparation of an immunologically-active adjuvant-bound freeze dried vaccine composition. Although a specific embodiment provides a vaccine composition comprising an aluminum-salt adjuvant, a recombinant *Clostridium botulinum* neurotoxin protein and a glass-forming agent, these methods are also useful for the preparation of other vaccine compositions comprising other vaccine antigens. Moreover, while various embodiments of the present disclosure have been described in detail, it is apparent that modifications and adaptations of those embodiments will occur to those skilled in the art. However, it is to be expressly understood that such modifications and adaptations are within the spirit and scope of the present disclosure.

Example 5

Stability of Lyophilized Recombinant Protein
Vaccines Against Botulinum Neurotoxin A stability study was performed with two objectives. The first objective was to minimize changes observed with storage of these vaccines through processing strategies, and the second objective was to observe the immunological effect of such changes in a murine model. Lyophilized vaccines containing mostly unaggregated adjuvant following lyophilization were tested for stability compared to a similarly-formulated liquid vaccine. rBoNTE, a recombinant protein known to be protective against botulinum neurotoxin type E, was used as the test antigen. The effects of storage at both refrigerated (2-8° C.) and elevated (40° C.) temperatures on the stability, immunogenicity and potency of liquid, freeze-dried, and spray freeze-dried preparations of vaccines containing rBoNTE(Hc) were examined Formulation conditions and lyophilization process parameters were chosen so as to avoid aggregation of the aluminum hydroxide adjuvant during lyophilization.

Materials

Trehalose (high purity, low endotoxin) was obtained from Ferro Pfanstiehl (Cleveland, Ohio). Succinic acid and sodium phosphate was purchased from Sigma Chemical Company (St. Louis, Mo.). Alhydrogel™ 2.0% aluminum hydroxide adjuvant (AH), made by Brenntag Biosector, was purchased from E.M. Sergeant Pulp & Chemical Co, Inc (Clifton, N.J.). 3-ml and 5-ml lyophilization vials and caps were obtained from West Pharmaceutical Services. All formulations were made using sterile water for injection from American Regent Inc. (Shirley, N.Y.). Purified rBoNTE(Hc), lot Exp-214-92, was provided by the Biological Process Development Facility at the University of Nebraska-Lincoln as a frozen stock solution (Sinha et al., 2007, J. Biotechnology 127:462-474).

Preparation of Liquid Samples for Long-Term Storage

The stock rBoNTE(Hc) solution was thawed and filtered through a 0.2 μm filter in a laminar flow hood. Protein concentration was determined by UV absorbance at 280 nm with an extinction coefficient of 1.675 (mg/mL)$^{-1}$ cm$^{-1}$. 500 mM sodium succinate, 300 mM sodium phosphate, and 40% (w/v) trehalose stock solution were prepared and were also filtered through 0.2 μm filter. 2% AH suspensions were obtained sterile, and handled in a laminar flow hood under sterile conditions. Excipient solutions were added to the protein solution to create four rBoNTE (H$_c$) formulations as follows. "Formulation 1" contained 81 μg/mL rBoNTE(H$_c$), 25 mM sodium succinate and 15 mM sodium phosphate buffer at pH 5.0. The other formulations were identical to formulation 1, with the addition of 0.2% (w/v) AH ("formulation 2"), 10% (w/v) trehalose ("formulation 3"), or both 10% trehalose and 0.2% AH ("formulation 4").

Preparation of Lyophilized Samples for Long-Term Storage

After filtration through a 0.2 nm filter for sterilization, antigen concentration was determined by UV absorbance. All aqueous solutions were passed through a 0.2 nm filter prior to formulation with the exception of the AH suspension, which was obtained sterile. Formulations contained 25 mM sodium succinate (pH 4.0), 81 μg/ml rBoNTE(Hc) and 10 w/v % trehalose. Half of the samples also contained 0.2 w/v % AH, whereas the remaining were processed without adjuvant.

Lyophilization

An FTS Systems Lyostar lyophilizer was used to prepare freeze-dried samples. Samples were frozen at two cooling rates as follows: (i) freezing by placing the samples in lyophilizer, equilibrating 1 hr at a shelf temperature of 0° C., then cooling the shelves at 0.5° C./min to −40° C. ("tray-freezing"); or (ii.) spray-freezing by dropping by ~20 nl droplets into liquid N$_2$. Dried samples produced by lyophilization following tray freezing are denoted FD; lyophilized, spray-frozen samples are denoted SFD. FD samples were processed in 3-ml lyophilization vials, whereas the SFD samples were processed in 5-ml lyophilization vials. Following freezing in liquid N$_2$, SFD samples were quickly transferred to the lyophilizer and placed on shelves pre-cooled to −40° C. Samples were spaced in the lyophilizer so that they were each separated from one another and were encircled with a row of vials containing water to minimize radiative heating from lyophilizer walls.

Primary drying of the samples was achieved by setting the shelf temperature to −20° C. and applying a vacuum at 60 mTorr for 20 hours, and was followed by secondary drying (also at 60 mTorr), in which shelf temperatures were ramped from −20° C. to 0° C. at 0.2° C./min, to 30° C. at 0.5° C./min and finally held at 30° C. for 5 hours. Samples were sealed under vacuum. Prior to use, samples were reconstituted with a solution of sodium phosphate to bring the final preparation to 25 mM sodium succinate, 15 mM sodium phosphate, pH 5.0. For samples that had been lyophilized without AH, AH (0.2%) was added after reconstitution prior to immunology and potency assays.

Particle Size Distributions

Particle size distributions (PSD's) were measured using a Beckman-Coulter LS230. Three one-ml samples were required for each run, and three replicates of each run were completed per formulation. Reported PSD's are surface-area weighted averages of three runs.

Coomassie Blue Total Protein Assay

Protein bound to adjuvant was measured using the Coomassie Plus Reagent (Pierce). A standard curve was prepared by preparing stock dilutions of a stock rBoNTE solution from which the protein concentration was determined by absorbance at 280 nm as above. Sample aliquots were mixed with the Coomassie reagent, incubated for 10 minutes at room temperature, and absorbance values were read on a FLUOstar OPTIMA microplate reader (BMG Labtech) at 595 nm. Protein bound to adjuvant was derived from a mass balance from the measured protein in solution and the total protein in the formulation.

rBoNTE(Hc) Desorption Assay

Proteins were desorbed from AH by incubating sample vaccine formulations with an equal volume of 250 mM succinate, pH 3.5 for 30 minutes at room temperature. Following incubation, samples were centrifuged at 15,000 G for 5 minutes, after which the supernatant was analyzed using the Coomassie assay described above.

Lys-C Digestion of rBoNTE(Hc) Samples

To facilitate desorption of protein from adjuvant prior to enzymatic digestion, 0.6 ml of 10 M urea were added to 1 ml samples containing rBoNTE(Hc) adsorbed on AH, and the pH was adjusted to 4.0. Samples were gently agitated overnight at room temperature, and then were centrifuged for 10 minutes at 3000 rpm. The supernatant (~1.5 ml) was concentrated using a YM-10 Centricon device (3000 rpm, ~20 minutes at room temperature) to a volume of approximately 120 μl, and the apparent rBoNTE(Hc) concentration was determined by UV spectroscopy. 60 μl of the concentrated supernatant was diluted with 30 μl of reaction buffer (0.5 M Tris, pH 7.9), after which Lys-C (Wako Chemicals USA Inc., Richmond, Va.) was added at a 1:25 mass ratio of Lys-C to rBoNTE(Hc). Samples were incubated at 37° C. for 4 hours, following which the digestion was quenched by the addition of 64 mg of Guanidine HCl (concentration 4 M). Samples were stored at −20° C. if not analyzed immediately.

Liquid Chromatography Mass Spectroscopy (LCMS)

Peptides resulting from Lys-C digestion of rBoNTE(Hc) samples were separated on a Jupiter C18 column at 35° C. with mobile phases of A) 0.1% (v/v) formic acid in water and B) 0.1% (v/v) formic acid in acetonitrile on an Agilent HP1100 system. Total flow rate was 0.25 mL/min, and the % A was ramped from 5% to 90% over 41 minutes. After elution from the column, half of the sample was directed to the UV detector whereas the other half was directed to the MS system. For samples aged from 0 weeks to 15 weeks, a loading of 10 μg/sample was used. However, for samples stored for 26 weeks, desorption of the protein from the adjuvant was not as complete, and samples were loaded at the maximum injection volume of 100 μl.

Mass spectrometric measurements were performed on a Bruker Esquire 2000 ion trap mass spectrometer (Bruker Daltonics, Bremen, Germany) equipped with an electrospray source working in positive ion mode. The instrument was connected with the HPLC system outlet via PEEK tubing and the divert valve was programmed to waste the first 15.0 min of the chromatographic run. MS parameters were the following: scan range m/z=100-2000, scan speed 13.000 m/z s$^{-1}$ with unit resolution, nebulizer pressure 45 psi, dry gas flow 12.0 L/min, dry temperature 365° C., capillary −3800 V, skimmer 33 V, ion charge control (ICC) target 30,000, maximum accumulation time 200 ms, spectra averages 5 and rolling averages 2.

SDS-PAGE Method for Analysis of Liquid Formulations

Samples of liquid formulations 1-4 were analyzed by SDS-PAGE using precast gradient gels (4%-20% Tris-HCl/glycine, Bio-Rad Laboratories, Inc., Hercules, Calif.). Samples were diluted 1:1 in Laemmli sample buffer (62.5 mMTris-HCl, pH 6.8, 25% glycerol, 2% SDS, 0.01% Bromophenol blue), with or without 750 mM β-mercaptoethanol, and incubated 30 min at room temperature prior to loading. The loading mass was 2 μg for each electrophoresis well. Gels were electrophoresed for 75 min at 200 volts, and then stained with Coomassie blue to visualize the protein bands. After destaining, the gel was placed between two sheets of cellophane and dried in a Biorad model 583 Gel Dryer. The dried gel was scanned with a Epson 4490 scanner, and the scanned images were quantitatively analyzed by Adobe Photoshop 7.0 software. The band's area was measured by circling the band along with its edge manually. Both the band's intensity as well as its area were given by the software, whereby the relative amount of protein in band was achieved using equation:

Relative amount of protein in band=(band intensity−background intensity)×band area Mouse Care All work involving animals was approved by the University of Colorado Health Sciences Center Institutional Animal Care and Use Committee under Protocol #77403806(07)1E. All procedures were done at the University of Colorado Health Sciences Center for Laboratory Animal Care. Mice were housed 5 to a cage with food and water (acidified) available ad libitum.

Mouse Immunization and Serum Collection

Female, 6 week old CD-1 mice (Charles River Laboratories) were used to assess the immunogenicity of each of the liquid, reconstituted FD, and reconstituted SFD formulations of AH-adjuvanted vaccines. Injections of 100 μl of the formulation containing 8.1 μg of rBoNTE(Hc) were administered subcutaneously along the back. Control mice were injected with a rBoNTE(Hc)-free suspension of AH in an equivalent buffer solution. A booster immunization was administered on day 14. Blood was collected via retro-orbital bleeding under anesthesia prior to each injection and 14 days following the booster immunization. Serum was separated by centrifugation at 12,500 rpm for 5 minutes, transferred to a clean centrifuge tube, and frozen at −80° C. until analysis.

Enzyme-Linked Immuno-Sorbent Assay (ELISA)

The antibody response to each vaccine was determined by ELISA. 96-well plates (Nunc, Rochester, N.Y.) were coated with 0.25 μg of rBoNTE(Hc) per well (50 μl) in 50 mM sodium bicarbonate pH 9.6 overnight at 4° C. Plates were washed with phosphate-buffered saline (PBS), pH 7.4.1% bovine serum albumin (BSA, Fisher) in PBS was used to block nonspecific sites. Plates were allowed to dry and were stored at 4° C. until use. Serum samples were thawed at room temperature and serially diluted in 1% BSA in PBS from 1:20 to 1:3.5$^6$ dilutions, and 50 μl of each samples was added to the 96 well-plate. Samples were incubated overnight at 4° C. After washing with PBS, plates were incubated with 50 μl horseradish peroxidase-conjugated goat-anti-mouse antibodies for IgG1 and IgE (Immunology Consultants Lab, Inc, Newberg, Oreg.) at 1:10,000 dilution for 2 hours at room temperature with rotation (400 rpm). Plates were then washed and incubated with 100 μl of Ultra-TMB (Pierce, Rockfort, Ill.). After 15 minutes of development, the reaction was quenched with 100 μl of 1 N HCl. Plates were read at an absorbance of 450 nm using a ThermoMax microplate reader (Molecular Devices, Sunnyvale, Calif.). Anti-rBoNTE(Hc) titers were calculated as the dilution factor that gave an absorbance reading equal to one standard deviation greater than the average of the negative control and were determined using a four-parameter fit analyzed using Softmax Pro software.

Potency Assay

Liquid, FD, and SFD vaccines were tested after 0, 3, and 15 weeks storage at 4° C. Groups of 10 CD-1 mice (Charles River Labs) were each given 0.1 ml of one of seven three-fold dilutions of vaccine, covering a rBoNTE(Hc) protein range of 8.1 ug/mouse to 11 ng/mouse. Vaccinations were administered on Day 0 and Day 14. Mice were challenged with 1000 mouse intraperitoneal lethal doses (MIPLD$_{50}$) of BoNTE lot #E062205-01 on Day 35. Survival of each mouse was noted, and ED-50 values were calculated from the data.

Results

SDS-PAGE

Figure 19:
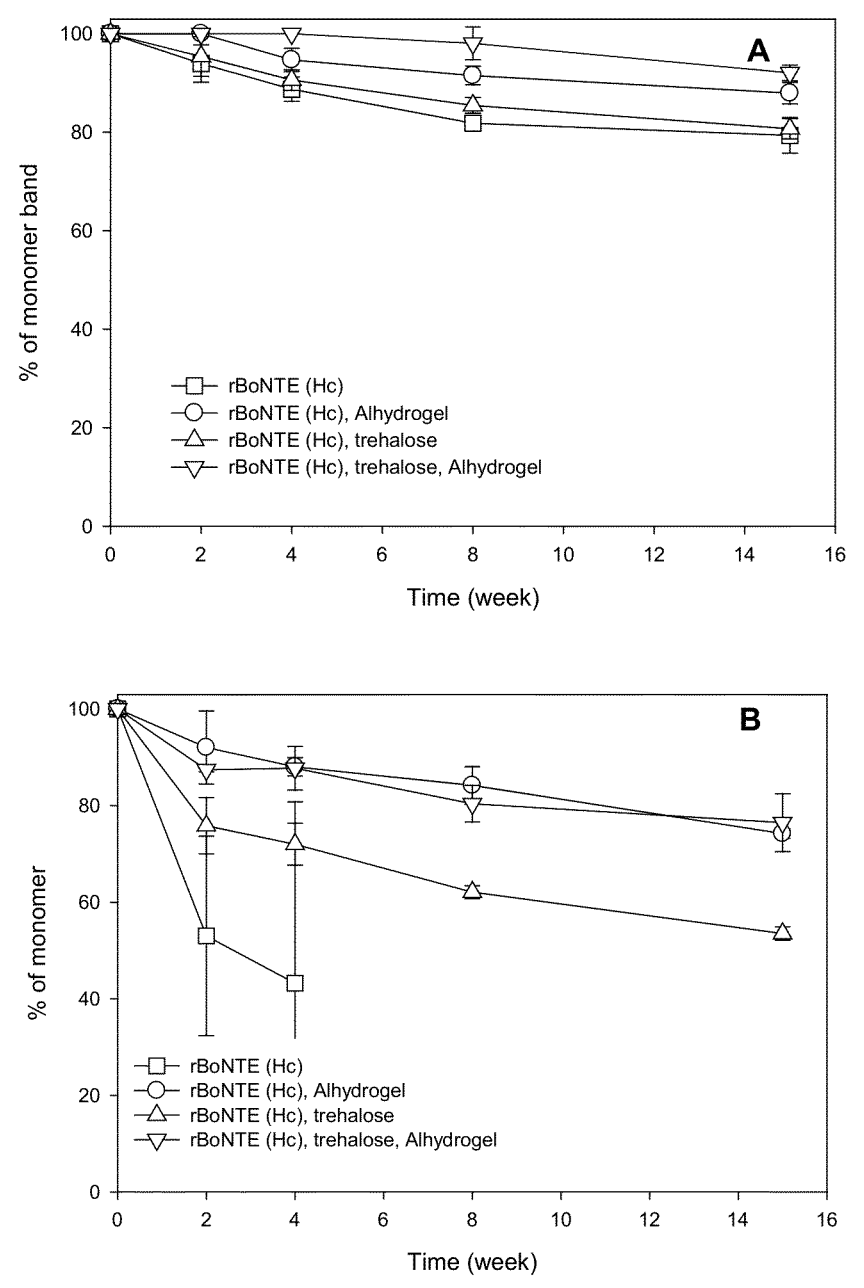

Liquid formulations 1-4 of rBoNTE(H$_c$) were analyzed as a function of storage time by SDS-PAGE. Initially, the rBoNTE(Hc) protein appeared as a single band with molecular weight slightly higher than 50 kDa. Neither high molecular weight (HMW) aggregate nor low molecular weight (LMW) fragments were observed. After 15 weeks incubation, there were still no HMW aggregates observed under either reducing or non-reducing gel conditions. However, fragments with molecular weights ranging from approximately 37-50 kDa were clearly observed. These LMW bands, suggestive of rBoNTE(Hc) hydrolysis, were more intense in samples incubated at 30° C. FIG. 19 shows the percent of the original rBoNTE(Hc) band remaining as a function of incubation temperature and time.

FIG. 19 shows the percentage of monomer remaining during incubation determined by SDS-PAGE Gel (reducing condition) at (A) 4° C. incubation, and (B) 30° C. incubation. Triplicate samples were tested at each sampling point, error bars represents standard error.

Less fragmentation was observed in formulations containing adjuvant, suggesting that the absorption to adjuvant protected protein from hydrolysis degradation, or, alternatively, that fragments of rBoNTE(Hc) remain preferentially adsorbed to adjuvant under the desorption conditions tested.

Particle Size Distributions of Lyophilized Vaccines Containing AH

The PSD's of AH in FD and SFD vaccines were measured immediately following lyophilization and reconstitution and after 26 weeks of storage at 4° C. and 40° C. (FIG. 20).

Figure 20:
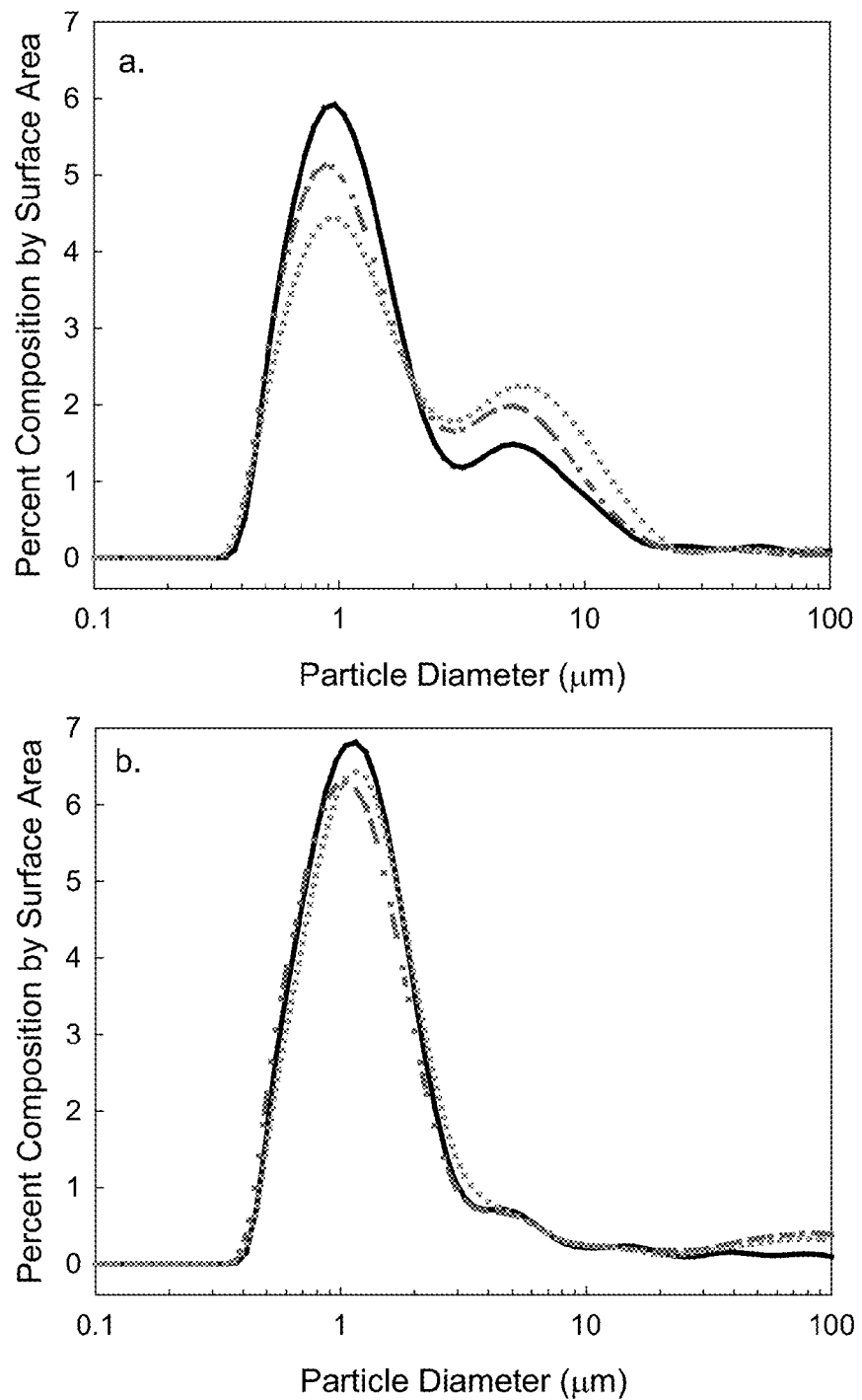
FIG. 20 shows particle size distribution of Alhydrogel™ 2.0% aluminum hydroxide (AH) in a.) Freeze-dried (FD) vaccines and b.) Spray freeze-dried (SFD) vaccines immediately following lyophilization and reconstitution (solid line), following storage at 4° C. for 26 weeks (dashed line), and following storage at 40° C. for 26 weeks (dotted line).

FIG. 20 shows particle size distribution of AH in A.) FD vaccines and B.) SFD vaccines immediately following lyophilization and reconstitution (solid line), following storage at 4° C. for 26 weeks (dashed line), and following storage at 40° C. for 26 weeks (dotted line).

At the start of the study, the PSD's for both FD and SFD vaccines showed particle size distributions centered near 1 μm, with a small percentage of larger particles (>10 μm) in the FD preparations. After 26 weeks storage there was a small shift towards higher particle diameters that was most evident in the FD samples. This increase in particle size was also more pronounced in samples stored at 40° C. than in those stored at 4° C.

Binding of Protein to Adjuvant

In liquid suspensions containing 25 mM sodium succinate, pH 4.0, approximately 65% of rBoNTE(Hc) adsorbs to AH. This is similar to the amount bound when the FD or SFD lyophilized preparations are reconstituted with water (FD=60±0.2%; SFD=56±2%). However, when formulated in or reconstituted to 25 mM sodium succinate, 15 mM sodium phosphate, pH 5.0, greater than 95% of the protein remains adsorbed. For these samples, no changes in the amount bound were observed in either SFD samples or in FD samples between 0 and 26 weeks (data not shown).

At the onset of the study, approximately 80% of the rBoNTE(Hc) could be desorbed from the adjuvant when the formulations were mixed with an equal volume of a desorption solution containing 250 mM sodium succinate, pH 3.5. During the first 15 weeks of storage, the amount of protein desorbed from the surface of the adjuvant remained relatively constant (FIG. 21).

Figure 21:
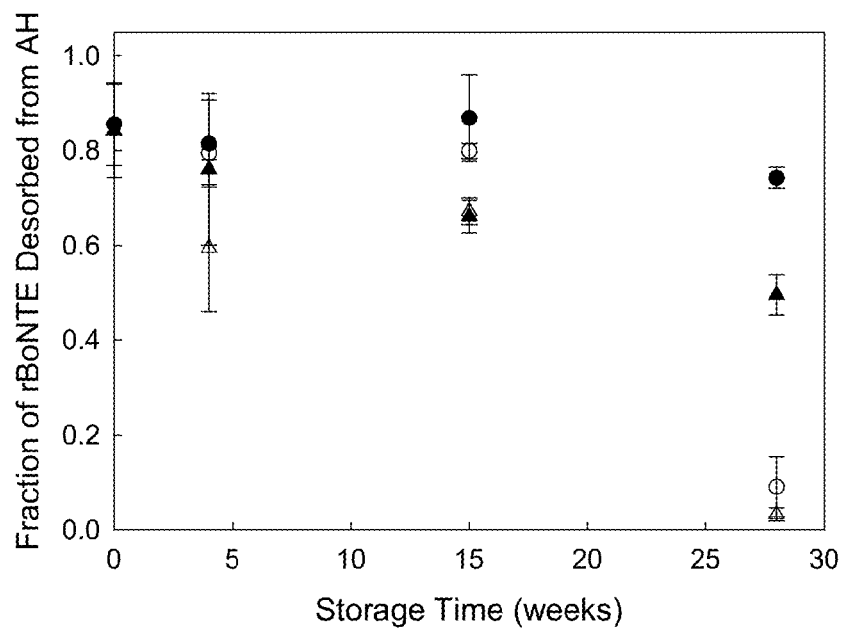
FIG. 21 shows the fraction of rBoNTE desorbed from AH in FD (circles) and SFD (triangles) vaccines stored at 4° C. (closed symbols) and 40° C. (open symbols) following the addition of the desorption solution (250 mM sodium succinate, pH 3.5).

FIG. 21 shows the fraction of rBoNTE desorbed from AH in FD (circles) and SFD (triangles) vaccines stored at 4° C. (closed symbols) and 40° C. (open symbols) following the addition of the desorption solution (250 mM sodium succinate, pH 3.5).

However, after 26 weeks of storage, there was a decrease in the amount of protein that could be recovered. In FD and SFD samples stored at 40° C., less than 15% of the protein was desorbed. In the SFD samples stored at 4° C., approximately 50% was desorbable, whereas there were no significant changes in desorption for the FD samples stored at 4° C.

Effect of Lyophilization on Adjuvant-Free rBoNTE(Hc) Formulations

Figure 22:
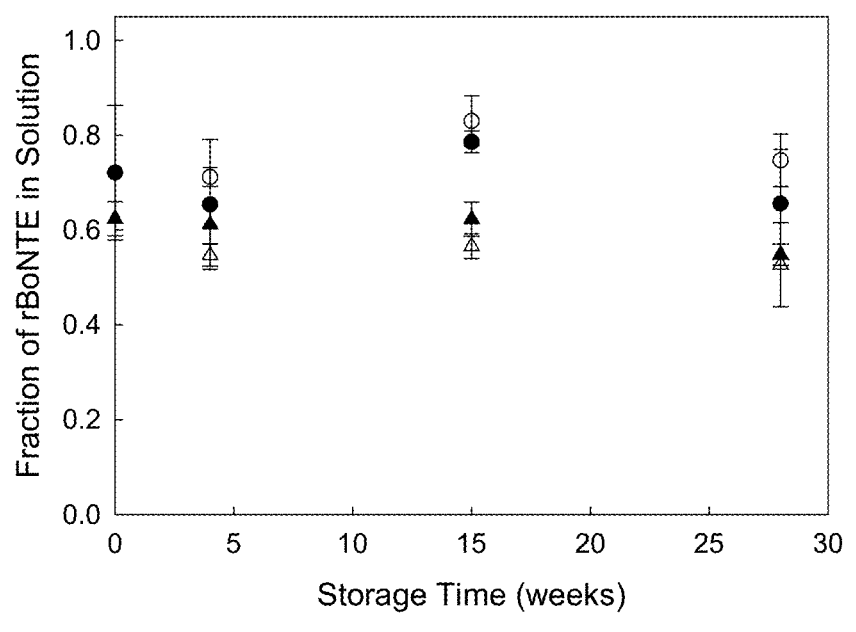

The percentage of protein recovered from SFD and FD formulations processed without AH was examined (FIG. 22).

FIG. 22 shows the fraction of soluble rBoNTE recovered in AH-free FD (circles) and SFD (triangles) formulations stored at 4° C. (closed symbols) and 40° C. (open symbols).

In all of these formulations a loss in soluble protein is observed following lyophilization and reconstitution. The FD preparation appears to be slightly more stable throughout processing with ~75% recovery whereas the SFD preparations have ~65% recovery. However, there was not a significant decrease in the percentage of soluble protein recovered with aging at either temperature.

LCMS analysis of Desorbed and Digested Samples

Prior to digestion with Lys-C, rBoNTE was desorbed from AH in a 6 M urea solution, pH 4.0. The resulting protein solution was then concentrated approximately 12-fold, and the concentration was determined by UV spectroscopy. It was observed that after 26 weeks of storage, less protein was recovered than from samples aged for 0, 4, or 15 weeks, similar to observations made previously when desorbed in a sodium succinate buffer. The loading on the LCMS was kept constant for all samples by adjusting the injection volumes, except for samples aged for 26 weeks, due to limitations with sample quantities.

Figure 23:
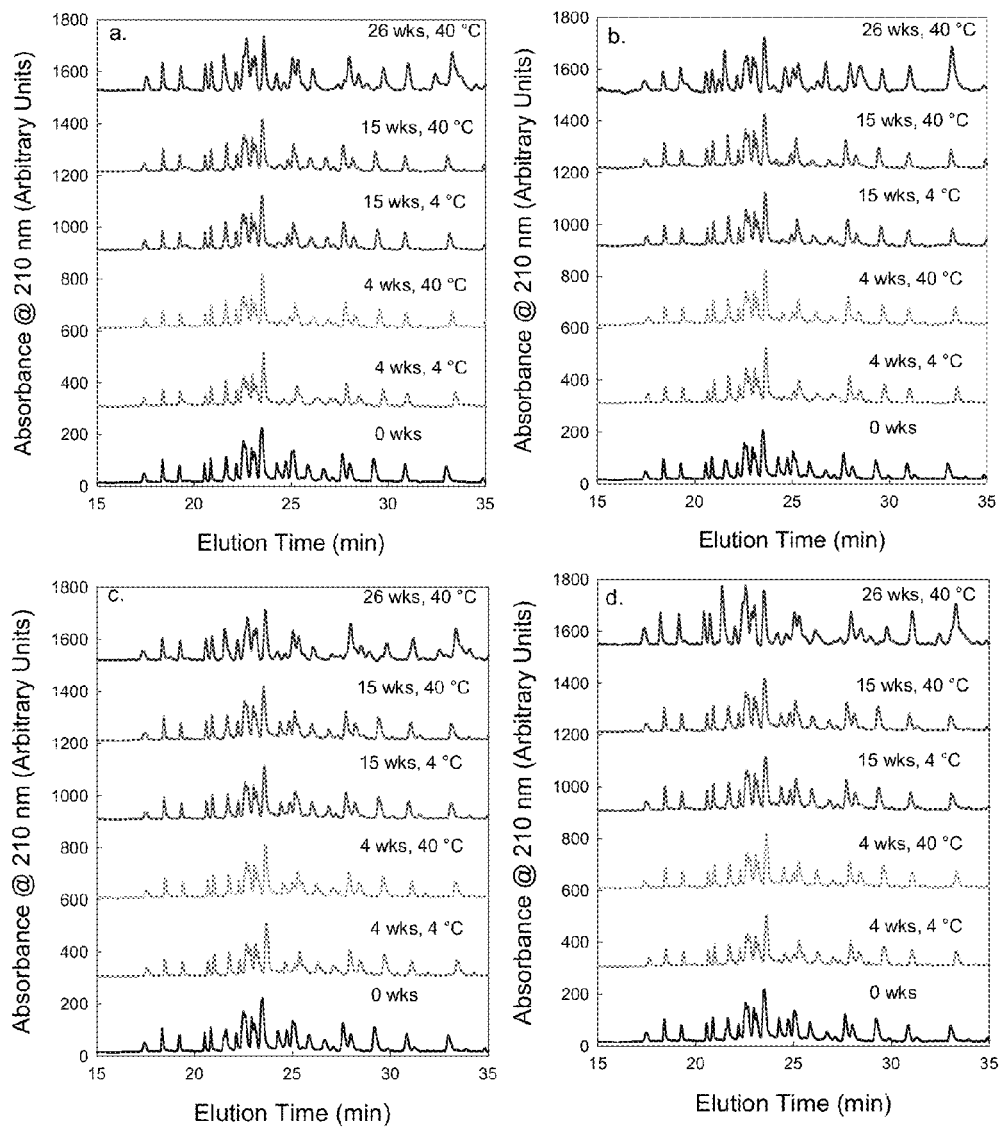
FIG. 23 shows liquid chromatograms of Lys-C digested rBoNTE(Hc) from samples reconstituted after various periods of incubation at 4° C. or 40° C. Formulations in the various panels are a.) FD vaccines with AH, b.) SFD vaccines with AH, c.) FD vaccines without AH, and d.) SFD vaccines without AH.

The chromatograms for the Lys-C digested proteins are presented in FIG. 23 with one representative sample from each vaccine (triplicate samples were run and were reproducible). Peaks were identified from the mass spectroscopy data. The chromatograms in FIG. 23 for the four lyophilized formulations a.) FD with AH, b.) SFD with AH, c.) FD without AH, and d.) SFD without AH were identical at the onset of the study. For samples up to 15 weeks of storage, the only region of observable changes is in the 24-25 minute region, where two peaks show up at some time points, but not all. The desorption of the antigen from the adjuvant was not as effective following 26 weeks of storage, resulting in less protein being loaded onto the column. Attempts to normalize the overall chromatogram height was attempted in order to observe the eluting peptides. At this last time point, there are some significant changes in the chromatograms, especially a larger peak at 33 minutes and possibly an additional peak appearing around 25 minutes. However, the rest of the chromatogram appears to be unchanged.

Table 2 shows the peptides expected to be observed for mass spectroscopic analysis of rBoNTE(Hc).

TABLE 2

Theoretical Lys-C digestion peptides of rBoNTE(H$_c$) protein (SEQ ID NO. 1).

| Peptide | Theoretical [M + H]$^+$ | Position | Amino Acid Sequence |
|---|---|---|---|
| E1 | 4446.9 | 413-449 | ADTVVASTWYYTHMRDHTNSNGCFWNFISEEHGWQEK |
| E2 | 2847.3 | 374-399 | ISSSGNRFNQVVVMNSVGNNCTMNFK |
| E3 | 2662.5 | 300-323 | DSTLSINNIRSTILLANRLYSGIK |
| E4 | 2597.2 | 127-148 | IVNVNNEYTIINCMRDNNSGWK |
| E5 | 2583.2 | 1-23 | MGESQQELNSMVTDTLNNSIPFK |
| E6 | 2485.3 | 230-249 | IVNCSYTRYIGIRYFNIFDK |
| E7 | 2464.2 | 250-270 | ELDETEIQTLYSNEPNTNILK |
| E8 | 2407.2 | 149-169 | VSLNHNEIIWTLQDNAGINQK |
| E9 | 2137 | 59-77 | YVDTSGYDSNININGDVYK |
| E10 | 2028 | 92-108 | LSEVNISQNDYIIYDNK |
| E11 | 2000 | 111-126 | NFSISFWVRIPNYDNK |
| E12 | 1897.1 | 213-229 | SILNLGNIHVSDNILFK |
| E13 | 1873.9 | 170-186 | LAFNYGNANGISDYINK |

TABLE 2-continued

Theoretical Lys-C digestion peptides of rBoNTE(H_c) protein (SEQ ID NO. 1).

| Peptide | Theoretical [M + H]+ | Position | Amino Acid Sequence |
|---|---|---|---|
| E14 | 1858 | 326-341 | IQRVNNSSTNDNLVRK |
| E15 | 1764.9 | 187-201 | WIFVTITNDRLGDSK |
| E16 | 1692.9 | 354-368 | THLFPLYADTATTNK |
| E17 | 1433.7 | 271-281 | DFWGNYLLYDK |
| E18 | 1397.7 | 342-353 | NDQVYINFVASK |
| E19 | 1374.7 | 400-412 | NNNGNNIGLLGFK |
| E20 | 1290.7 | 202-212 | LYINGNLIDQK |
| E21 | 1184.6 | 46-55 | SSSVLNMRYK |
| E22 | 1159.6 | 291-299 | PNNFIDRRK |
| E23 | 1154.6 | 282-290 | EYYLLNVLK |
| E24 | 1098.5 | 83-91 | NQFGIYNDK |
| E25 | 997.6 | 32-39 | ILISYFNK |
| E26 | 928.4 | 24-31 | LSSYTDDK |
| E27 | 622.3 | 78-82 | YPTNK |
| E28 | 441.2 | 40-42 | FFK |
| E29 | 416.3 | 43-45 | RIK |
| E30 | 376.2 | 56-58 | NDK |
| E31 | 361.2 | 371-373 | TIK |
| E32 | 310.2 | 109-110 | YK |
| E33 | 276.2 | 369-370 | EK |
| E34 | 246.2 | 324-325 | VK |

Peptides with a mass lower than 500 Da are typically not detectable, but may be observed if there is an incomplete digestion of two other fragments.

Tables 3-4 show the peptides observed for the FD and SFD formulations respectively, for samples lyophilized with AH. Tables 5-6 show the peptides observed in FD and SFD formulations respectively for samples lyophilized in the absence of AH. The tables show the masses observed and the elution times observed for each peptide. At the onset of the study, the sequence coverage is around 75%. Peptides E1, E5, E27, and E29-E34 are not observed in any samples. Peptides E4, and E6 appear only in the stock protein and in most samples following 26 weeks of storage. Masses corresponding to peptides E2 and E25 only appear after 26 weeks of storage. For peptides E9 and E28, there is a significant drop in most of the preparations after 26 weeks of storage. The drop in peptide E9 is only seen in samples lyophilized in the presence of AH, while the drop in peptide E28 is seen in all preparations except for the FD samples without AH. Masses of 2740.3, 2494.1, and 2295.3 are identified as peptides with in incomplete digestion with one missed cleavage.

Figure 24:
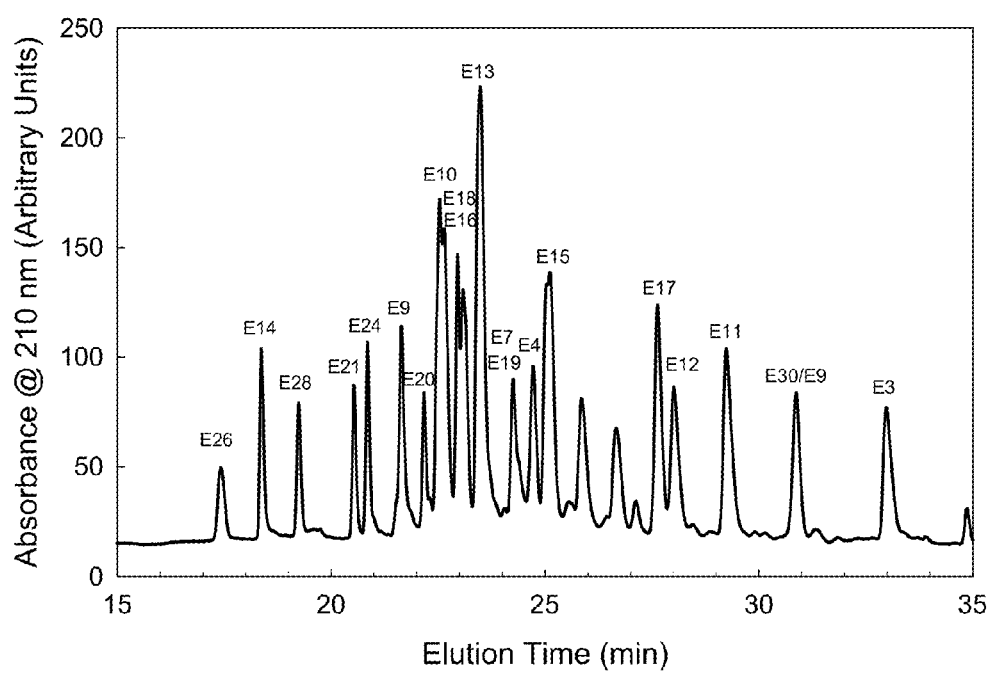
FIG. 24 shows a sample RP-HPLC chromatogram of Lys-C digested rBoNTE antigen with peaks identified from mass spectroscopy data.

FIG. 24 shows a sample RP-HPLC chromatogram of Lys-C digested rBoNTE antigen with peaks identified from mass spectroscopy data. Peaks between 25 and 27.5 minutes could not be identified due to inconsistent mass spectroscopy data in this region, although the peaks appear in all LC chromatograms.

TABLE 3

Identified masses in FD formulation lyophilized with AH.

| Peptide ID | Theoretical [M + H]+ | Observed Mass | Elution Time | Stock | FD-AH 0 wk | FD-AH 4 wk 4° C. | FD-AH 4 wk 40° C. | FD-AH 15 wk 4° C. | FD-AH 15 wk 40° C. | FD-AH 26 wk 40° C. |
|---|---|---|---|---|---|---|---|---|---|---|
| E1 | 4446.9 | | | | | | | | | |
| E2 | 2847.3 | 2847.1-2847.4 | 23.0-23.1 | | | | | | | ++ |
| E9/E27 | 2740.3 | 2739.9-2740.3 | 21.7-22.1 | +++ | ++ | | + | ++ | + | +++ |
| E3 | 2662.5 | 2662.2-2662.5 | 33.2-34 | + | +++ | +++ | ++ | + | + | +++ |
| E4 | 2597.2 | 1591.1-2597.2 | 24.6 | +++ | | | | | | +++ |
| E5 | 2583.2 | | | | | | | | | |

TABLE 3-continued

Identified masses in FD formulation lyophilized with AH.

| Peptide ID | Theoretical [M + H]+ | Observed Mass | Elution Time | Stock | FD-AH 0 wk | FD-AH 4 wk 4° C. | FD-AH 4 wk 40° C. | FD-AH 15 wk 4° C. | FD-AH 15 wk 40° C. | FD-AH 26 wk 40° C. |
|---|---|---|---|---|---|---|---|---|---|---|
| E30/E9 | 2494.1 | 2493.9-2494.1 | 31.0-31.5 | +++ | ++ | +++ | ++ | ++ | +++ | +++ |
| E6 | 2485.3 | 2485.1-2485.2 | 27.2-28.2 | +++ | | | | | | ++ |
| E7 | 2464.2 | 2463.9-2464.1 | 23.8-24.4 | +++ | +++ | +++ | +++ | ++ | ++ | ++ |
| E8 | 2407.2 | 2406.9-2407.2 | 23.7-24.2 | ++ | +++ | +++ | ++ | ++ | ++ | ++ |
| E23/E22 | 2295.3 | 2295.1-2295.2 | 25.0-25.4 | +++ | +++ | | | + | + | +++ |
| E9 | 2137 | 2136.8-2136.9 | 21.8-22.4 | +++ | +++ | +++ | +++ | +++ | +++ | + |
| E10 | 2028 | 2027.8-2028 | 22.6-23.1 | + | ++ | ++ | ++ | +++ | +++ | + |
| E11 | 2000 | 1999.8-2000.0 | 29.4-30.2 | +++ | +++ | +++ | +++ | +++ | +++ | +++ |
| E12 | 1897.1 | 1896.9-1897.1 | 28.2-29.4 | +++ | +++ | +++ | +++ | ++ | +++ | ++ |
| E13 | 1873.9 | 1873.7-1873.9 | 23.2-24.4 | +++ | +++ | ++ | +++ | ++ | ++ | ++ |
| E14 | 1858 | 1857.8-1858.1 | 18.5-19.4 | +++ | +++ | +++ | +++ | +++ | +++ | +++ |
| E15 | 1764.9 | 1764.7-1764.9 | 25.2-26.0 | +++ | +++ | +++ | +++ | +++ | ++ | ++ |
| E16 | 1692.9 | 1692.7-1692.9 | 22.9-23.2 | ++ | +++ | +++ | +++ | ++ | +++ | ++ |
| E17 | 1433.7 | 1433.6-1433.7 | 27.7-28.5 | ++ | +++ | +++ | +++ | ++ | +++ | +++ |
| E18 | 1397.7 | 1397.6-1397.7 | 22.7-23.1 | + | +++ | +++ | ++ | +++ | ++ | +++ |
| E19 | 1374.7 | 1374.5-1374.8 | 23.9-24.0 | + | ++ | ++ | + | | ++ | + |
| E20 | 1290.7 | 1290.6-1290.7 | 22.4-22.7 | +++ | ++ | +++ | +++ | ++ | +++ | +++ |
| E21 | 1184.6 | 1184.5-1184.6 | 20.7-21.2 | +++ | ++ | +++ | ++ | +++ | ++ | +++ |
| E22 | 1159.6 | 1159.6-1159.7 | 18.8-19.0 | | | | + | | ++ | |
| E23 | 1154.6 | 1154.5-1154.7 | 27.3-27.6 | + | | ++ | | | | |
| E24 | 1098.5 | 1098.4-1098.7 | 21.1-21.5 | ++ | ++ | +++ | ++ | ++ | ++ | ++ |
| E25 | 997.6 | 997.5-997.6 | 23.4-23.5 | | | | | | | +++ |
| E26 | 928.4 | 928.3-928.5 | 17.6-17.9 | +++ | +++ | +++ | +++ | +++ | +++ | +++ |
| E27 | 622.3 | | | | | | | | | |
| E28 | 441.2 | 441.2-441.3 | 19.6-19.7 | +++ | +++ | +++ | +++ | +++ | ++ | + |

Observed mass and elution time ranges are shown.
Number of + symbols indicate #/3 samples mass appeared in.
Peptides left blank were not observed.

TABLE 4

Identified masses in SFD formulation lyophilized with AH.

| Peptide ID | Theoretical [M + H]+ | Observed Mass | Elution Time | Stock | SFD-AH 0 wk | SFD-AH 4 wk 4° C. | SFD-AH 4 wk 40° C. | SFD-AH 15 wk 4° C. | SFD-AH 15 wk 40° C. | SFD-AH 26 wk 40° C. |
|---|---|---|---|---|---|---|---|---|---|---|
| E1 | 4446.9 | | | | | | | | | |
| E2 | 2847.3 | | | | | | | | | |
| E9/E27 | 2740.3 | 2739.9-2740.3 | 21.7-22.1 | +++ | +++ | ++ | ++ | + | + | +++ |
| E3 | 2662.5 | 2662.2-2662.5 | 33.2-34.2 | + | + | + | +++ | + | ++ | |
| E4 | 2597.2 | 2597.1-2597.9 | 24.2-24.6 | +++ | | | | | | + |
| E5 | 2583.2 | | | | | | | | | |
| E30/E9 | 2494.1 | 2493.9-2494.1 | 31.0-31.6 | +++ | +++ | +++ | ++ | ++ | ++ | +++ |
| E6 | 2485.3 | 2485.1-2485.2 | 27.2-27.9 | +++ | | | | | | ++ |
| E7 | 2464.2 | 2463.9-2464.2 | 23.9-24.2 | +++ | +++ | ++ | ++ | ++ | +++ | +++ |
| E8 | 2407.2 | 2406.9-2407.2 | 23.7-24.1 | ++ | ++ | + | | ++ | +++ | + |
| E23/E22 | 2295.3 | 2295.0-2295.2 | 25.0-25.5 | +++ | +++ | + | +++ | + | + | +++ |
| E9 | 2137 | 2136.7-2138.0 | 21.8-22.4 | +++ | +++ | +++ | +++ | +++ | ++ | + |
| E10 | 2028 | 2027.8-2028.0 | 22.7-23.3 | + | ++ | + | +++ | ++ | + | + |
| E11 | 2000 | 1999.8-2000.0 | 29.4-30.2 | +++ | +++ | ++ | +++ | +++ | ++ | +++ |
| E12 | 1897.1 | 1896.8-1897.1 | 28.2028.9 | +++ | ++ | ++ | ++ | ++ | ++ | +++ |
| E13 | 1873.9 | 1873.7-1873.9 | 23.2-23.7 | +++ | +++ | +++ | ++ | + | +++ | ++ |
| E14 | 1858 | 1857.8-1858.0 | 18.5-19.2 | +++ | +++ | +++ | +++ | +++ | ++ | +++ |
| E15 | 1764.9 | 1764.7-1765.0 | 25.2-25.9 | +++ | ++ | ++ | ++ | +++ | +++ | + |
| E16 | 1692.9 | 1692.7-1692.9 | 23.0-23.4 | ++ | ++ | ++ | +++ | +++ | +++ | +++ |
| E17 | 1433.7 | 1433.5-1433.7 | 27.7-28.3 | ++ | +++ | +++ | +++ | +++ | +++ | ++ |
| E18 | 1397.7 | 1397.6-1397.8 | 22.8-23.1 | + | + | +++ | + | +++ | +++ | ++ |
| E19 | 1374.7 | 1374.5-1374.7 | 23.9-24.2 | + | ++ | ++ | ++ | +++ | + | + |
| E20 | 1290.7 | 1290.6-1290.8 | 22.4-22.6 | +++ | +++ | + | +++ | ++ | + | ++ |
| E21 | 1184.6 | 1184.5-1184.6 | 20.7-21.2 | +++ | + | +++ | ++ | +++ | +++ | ++ |
| E22 | 1159.6 | 1159.4-1159.7 | 18.8-18.9 | | | + | ++ | | + | |
| E23 | 1154.6 | 1154.7 | 27.3 | + | | | | | | |
| E24 | 1098.5 | 1098.5-1098.6 | 21.2-21.6 | ++ | ++ | + | ++ | +++ | ++ | ++ |
| E25 | 997.6 | | | | | | | | | ++ |
| E26 | 928.4 | 928.3-928.4 | 17.6-18.0 | +++ | +++ | ++ | +++ | +++ | +++ | ++ |
| E27 | 622.3 | | | | | | | | | |
| E28 | 441.2 | 441.2-441.3 | 19.6-19.7 | +++ | +++ | ++ | +++ | +++ | +++ | |

TABLE 4-continued

Identified masses in SFD formulation lyophilized with AH.

| Peptide ID | Theoretical [M + H]⁺ | Observed Mass | Elution Time | Stock | SFD-AH 0 wk | SFD-AH 4 wk 4° C. | SFD-AH 4 wk 40° C. | SFD-AH 15 wk 4° C. | SFD-AH 15 wk 40° C. | SFD-AH 26 wk 40° C. |
|---|---|---|---|---|---|---|---|---|---|---|

Observed mass and elution time ranges are shown.
Number of + symbols indicate #/3 samples mass appeared in.
Peptides left blank were not observed.

TABLE 5

Identified masses in FD formulation lyophilized without AH.

| Peptide ID | Theoretical [M + H]⁺ | Observed Mass | Elution Time | Stock | FD 0 wk | FD 4 wk 4° C. | FD 4 wk 40° C. | FD 15 wk 4° C. | FD 15 wk 40° C. | FD 26 wk 40° C. |
|---|---|---|---|---|---|---|---|---|---|---|
| E1 | 4446.9 | | | | | | | | | |
| E2 | 2847.3 | 2847.1-2847.2 | 23.0-25.0 | + | | | | | | +++ |
| E9/E27 | 2740.3 | 2739.9-2740.3 | 21.7-22.0 | +++ | + | + | + | + | + | +++ |
| E3 | 2662.5 | 2662.2-2662.4 | 33.3-34.0 | + | + | + | + | + | ++ | ++ |
| E4 | 2597.2 | 2597.1-2597.2 | 24.4-24.8 | ++ | + | | | | | + |
| E5 | 2583.2 | | | | | | | | | |
| E30/E9 | 2494.1 | 2493.9-2494.1 | 31.0-31.7 | +++ | +++ | ++ | +++ | ++ | +++ | +++ |
| E6 | 2485.3 | 2485.1-2485.2 | 27.2-28.0 | +++ | | | | | | +++ |
| E7 | 2464.2 | 2463.9-2463.4 | 23.7-24.3 | +++ | +++ | +++ | +++ | +++ | ++ | +++ |
| E8 | 2407.2 | 2407.0-2407.2 | 23.6-24.4 | ++ | ++ | +++ | +++ | ++ | +++ | + |
| E23/E22 | 2295.3 | 2295.0-2295.3 | 25.0-25.4 | +++ | ++ | | | ++ | +++ | +++ |
| E9 | 2137 | 2136.8-2137.0 | 21.9-22.5 | +++ | ++ | +++ | +++ | +++ | +++ | ++ |
| E10 | 2028 | 2027.8-2028.0 | 22.6-23.2 | + | + | | ++ | +++ | + | + |
| E11 | 2000 | 1999.8-2000.0 | 29.4-30.4 | +++ | +++ | ++ | +++ | ++ | +++ | +++ |
| E12 | 1897.1 | 1896.8-1897.1 | 28.2-29.4 | +++ | +++ | +++ | ++ | +++ | ++ | +++ |
| E13 | 1873.9 | 1873.7-1873.9 | 23.2-23.6 | +++ | ++ | +++ | ++ | +++ | ++ | +++ |
| E14 | 1858 | 1857.8-1858.0 | 18.1-19.5 | +++ | +++ | +++ | +++ | +++ | +++ | +++ |
| E15 | 1764.9 | 1764.7-17765.0 | 25.2-25.9 | +++ | +++ | +++ | +++ | +++ | +++ | +++ |
| E16 | 1692.9 | 1692.7-1692.9 | 22.8-23.3 | ++ | +++ | +++ | +++ | +++ | ++ | ++ |
| E17 | 1433.7 | 1433.6-1433.9 | 27.7-28.4 | ++ | ++ | ++ | +++ | +++ | ++ | +++ |
| E18 | 1397.7 | 1397.6-1397.7 | 22.8-23.1 | + | +++ | | + | +++ | ++ | ++ |
| E19 | 1374.7 | 1374.6-1374.7 | 23.8-24.6 | + | +++ | + | ++ | + | ++ | ++ |
| E20 | 1290.7 | 1290.6-1290.7 | 22.4-22.8 | +++ | ++ | +++ | +++ | +++ | +++ | +++ |
| E21 | 1184.6 | 1184.5-1184.7 | 20.7-21.2 | +++ | +++ | +++ | ++ | + | +++ | +++ |
| E22 | 1159.6 | | | | | | | | | |
| E23 | 1154.6 | | | | | | | | | |
| E24 | 1098.5 | 1098.4-1098.6 | 21.0-21.7 | ++ | +++ | +++ | + | ++ | +++ | ++ |
| E25 | 997.6 | 997.5-997.6 | 23.3-23.5 | | | | | | | +++ |
| E26 | 928.4 | 928.4-928.4 | 17.5-18.0 | +++ | +++ | +++ | +++ | +++ | ++ | +++ |
| E27 | 622.3 | | | | | | | | | |
| E28 | 441.2 | 441.2-441.3 | 19.5-19.8 | +++ | +++ | +++ | +++ | +++ | +++ | +++ |

Observed mass and elution time ranges are shown.
Number of + symbols indicate #/3 samples mass appeared in.
Peptides left blank were not observed.

TABLE 6

Identified masses in SFD formulation lyophilized without AH.

| Peptide ID | Theoretical [M + H]⁺ | Observed Mass | Elution Time | Stock | SFD 0 wk | SFD 4 wk 4° C. | SFD 4 wk 40° C. | SFD 15 wk 4° C. | SFD 15 wk 40° C. | SFD 26 wk 40° C. |
|---|---|---|---|---|---|---|---|---|---|---|
| E1 | 4446.9 | | | | | | | | | |
| E2 | 2847.3 | | | | | | | | | |
| E9/E27 | 2740.3 | 2740.1-2740.3 | 21.7-22.1 | ++ | ++ | | | +++ | ++ | +++ | ++ |
| E3 | 2662.5 | 2662.1-2662.4 | 33.5-34.0 | + | ++ | ++ | + | | | ++ |
| E4 | 2597.2 | 2597.1-2597.2 | 24.6-24.6 | ++ | | | | | | |
| E5 | 2583.2 | | | | | | | | | |
| E30/E9 | 2494.1 | 2493.9-2493.1 | 31.0-31.9 | +++ | ++ | +++ | ++ | +++ | +++ | ++ |
| E6 | 2485.3 | 2485.1-2485.2 | 27.2-27.9 | +++ | | | | | | |
| E7 | 2464.2 | 2463.8-2464.2 | 23.9-24.3 | +++ | +++ | +++ | +++ | +++ | +++ | |

TABLE 6-continued

Identified masses in SFD formulation lyophilized without AH.

| Peptide ID | Theoretical [M + H]+ | Observed Mass | Elution Time | Stock | SFD 0 wk | SFD 4 wk 4° C. | SFD 4 wk 40° C. | SFD 15 wk 4° C. | SFD 15 wk 40° C. | SFD 26 wk 40° C. |
|---|---|---|---|---|---|---|---|---|---|---|
| E8 | 2407.2 | 2406.9-2407.2 | 23.8-24.4 | ++ | ++ | +++ | +++ | ++ | ++ | + |
| E23/E22 | 2295.3 | 2295.0-2295.3 | 25.0-25.6 | +++ | +++ | ++ | ++ | ++ | | +++ |
| E9 | 2137 | 2136.7-2137.0 | 21.9-22.7 | +++ | +++ | +++ | +++ | +++ | +++ | + |
| E10 | 2028 | 2027.8-2028.0 | 22.7-22.9 | + | +++ | | +++ | + | +++ | ++ |
| E11 | 2000 | 1999.8-2000.0 | 29.4-30.4 | +++ | +++ | +++ | ++ | +++ | +++ | +++ |
| E12 | 1897.1 | 1896.7-1897.1 | 28.2-29.4 | +++ | +++ | +++ | ++ | +++ | +++ | +++ |
| E13 | 1873.9 | 1873.7-1873.9 | 23.2-25.2 | +++ | ++ | +++ | +++ | +++ | +++ | +++ |
| E14 | 1858 | 1857.8-1858.0 | 18.3-19.5 | +++ | +++ | +++ | +++ | +++ | +++ | +++ |
| E15 | 1764.9 | 1764.7-1765.0 | 25.2-25.9 | +++ | ++ | +++ | +++ | ++ | +++ | +++ |
| E16 | 1692.9 | 1692.7-1692.9 | 22.9-23.3 | ++ | +++ | + | +++ | ++ | +++ | ++ |
| E17 | 1433.7 | 1433.4-1433.7 | 27.7-28.5 | ++ | +++ | ++ | ++ | +++ | +++ | ++ |
| E18 | 1397.7 | 1397.6-1397.7 | 22.8-23.2 | + | +++ | ++ | ++ | ++ | +++ | +++ |
| E19 | 1374.7 | 1373.6-1374.8 | 23.6-24.3 | + | +++ | + | +++ | ++ | ++ | + |
| E20 | 1290.7 | 1290.5-1290.7 | 22.4-22.8 | +++ | + | ++ | +++ | +++ | ++ | +++ |
| E21 | 1184.6 | 1184.5-1184.7 | 20.7-21.1 | +++ | +++ | +++ | +++ | ++ | +++ | +++ |
| E22 | 1159.6 | 1159.5-1159.6 | 18.8-18.9 | | | | + | + | | |
| E23 | 1154.6 | 1154.7 | 27.3 | + | | | | | | |
| E24 | 1098.5 | 1098.4-1098.6 | 21.1-21.5 | ++ | +++ | +++ | ++ | + | +++ | +++ |
| E25 | 997.6 | 997.5-997.6 | 23.4-23.6 | | | | | + | | +++ |
| E26 | 928.4 | 928.3-928.5 | 17.6-18.1 | +++ | ++ | +++ | +++ | +++ | +++ | +++ |
| E27 | 622.3 | | | | | | | | | |
| E28 | 441.2 | 441.2-441.3 | 19.5-19.9 | +++ | +++ | +++ | +++ | ++ | +++ | +++ |

Observed mass and elution time ranges are shown.
Number of + symbols indicate #/3 samples mass appeared in.
Peptides left blank were not observed.

TABLE 7

Unidentified masses in FD formulation lyophilized with AH.

| Observed Mass | Elution Time | Stock | FD-AH 0 wk | FD-AH 4 wk 4° C. | FD-AH 4 wk 40° C. | FD-AH 15 wk 4° C. | FD-AH 15 wk 40° C. | FD-AH 26 wk 40° C. |
|---|---|---|---|---|---|---|---|---|
| 2778.0-2779.1 | 30.4-31.5 | | ++ | ++ | | + | ++ | |
| 2451.9-2452.2 | 27.5-27.9 | | + | + | | + | +++ | +++ |
| 2359.3-2359.4 | 33.3-33.8 | + | + | + | | + | | |
| 2273.0-2273.1 | 27.2-27.8 | ++ | | | | | | |
| 2246.1-2246.4 | 33.3-33.8 | +++ | ++ | | + | + | ++ | ++ |
| 2200.8-2201.5 | 25.2-25.4 | | | | ++ | + | + | |
| 2158.7-2158.9 | 22.1-22.3 | ++ | + | + | | + | | |
| 2103.6-2104.0 | 31.1-31.5 | +++ | +++ | ++ | +++ | ++ | + | |
| 2085.7-2085.9 | 31.2-31.6 | ++ | + | + | | + | + | |
| 1900.7-1901 | 20.0-20.2 | + | +++ | | | + | + | ++ |
| 1879.7-1880.8 | 18.7-18.9 | + | + | + | | + | + | ++ |
| 1874.7-1875.0 | 22.1-23.7 | | + | | ++ | | ++ | |
| 1858.8-1858.9 | 18.7-19.3 | ++ | | | | | | |
| 1807.8-1807.8 | 36.5-36.8 | +++ | +++ | | | | | |
| 1738.7-1738.9 | 29.4-30.6 | +++ | +++ | +++ | +++ | ++ | +++ | ++ |
| 1696.7-1696.9 | 28.3-29.9 | + | +++ | ++ | ++ | +++ | +++ | ++ |
| 1530.2-1530.6 | 25-25.4 | ++ | | | | | | |
| 1515.9-1516.0 | 31.3-31.4 | | | | | | | ++ |
| 1497.6-1498.3 | 33.1-33.8 | + | ++ | ++ | + | | | |
| 1465.6-1465.8 | 25.2-25.7 | +++ | ++ | +++ | ++ | +++ | +++ | ++ |
| 1171.5-1171.6 | 27.9-28.3 | +++ | ++ | | | + | | |
| 1098.5-1097.6 | 21.0-21.3 | + | ++ | | + | + | + | ++ |
| 1014.5-1014.6 | 22.5-22.7 | ++ | | + | + | | | |
| 985.3-985.5 | 28.0-28.4 | + | ++ | ++ | ++ | ++ | ++ | + |
| 972.3-972.3 | 17.8-17.9 | | | | | | | ++ |
| 950.3-950.4 | 17.7-17.9 | | | | | | | +++ |
| 906.2-906.3 | 36.8-36.9 | | | | | | | ++ |
| 901.4-901.5 | 22.5-23.2 | | +++ | + | + | ++ | ++ | |
| 890.3-890.5 | 26.4-27.0 | | | | | | | ++ |
| 884.4-884.5 | 23.5-23.7 | ++ | | + | | | | |
| 881.6-881.9 | 25.5-26.0 | ++ | | | | | | |
| 862.5-862.6 | 27.0-27.4 | ++ | | | | | | |
| 856.3-856.4 | 21.1-21.5 | +++ | +++ | +++ | +++ | +++ | +++ | + |
| 824.3-824.5 | 20.8-21.0 | +++ | +++ | +++ | +++ | +++ | +++ | |
| 821.0-821.9 | 23.1-24.1 | | | + | | ++ | +++ | |

TABLE 7-continued

Unidentified masses in FD formulation lyophilized with AH.

| Observed Mass | Elution Time | Stock | FD-AH 0 wk | FD-AH 4 wk 4° C. | FD-AH 4 wk 40° C. | FD-AH 15 wk 4° C. | FD-AH 15 wk 40° C. | FD-AH 26 wk 40° C. |
|---|---|---|---|---|---|---|---|---|
| 815.3-815.3 | 17.8-18.0 | +++ | +++ | +++ | ++ | +++ | +++ | +++ |
| 771.3-771.4 | 23.4-23.6 | ++ | +++ | +++ | + | ++ | ++ | +++ |
| 738.4-738.4 | 21.5-22.4 | | | | | | | ++ |
| 728.2-728.3 | 17.7-17.9 | +++ | ++ | +++ | +++ | +++ | +++ | + |
| 711.3-711.4 | 20.8-21.1 | +++ | +++ | +++ | ++ | +++ | ++ | |
| 709.2-709.4 | 21.2-21.5 | +++ | +++ | ++ | ++ | +++ | ++ | |
| 641.2-641.3 | 17.7-17.9 | ++ | | | | | | |
| 606.3-606.4 | 21.5-21.6 | | | | | | | +++ |
| 582.3-582.6 | 18.8-18.8 | ++ | | | | | | |
| 562.4-562.4 | 21.3-21.3 | | | | | | | ++ |

Observed mass and elution time ranges are shown.
Number of + symbols indicate #/3 samples mass appeared in.
Only masses that observed in >1 repetition/sample are shown.

TABLE 8

Unidentified masses in SFD formulation lyophilized with AH.

| Observed Mass | Elution Time | Stock | SFD-AH 0 wk | SFD-AH 4 wk 4° C. | SFD-AH 4 wk 40° C. | SFD-AH 15 wk 4° C. | SFD-AH 15 wk 40° C. | SFD-AH 26 wk 40° C. |
|---|---|---|---|---|---|---|---|---|
| 2779.0-2779.1 | 30.3-31.1 | | + | + | | | + | |
| 2778.0-2778.2 | 30.1-31.0 | | + | +++ | ++ | + | + | |
| 2751.1-2751.7 | 35.3-35.4 | | ++ | | | + | + | |
| 2540.0-2540.1 | 26.6-26.8 | | | | + | ++ | | |
| 2460.2-2460.2 | 33.5-33.9 | | | | ++ | | + | |
| 2451.9-2452.2 | 27.6-27.9 | | + | ++ | ++ | + | + | + |
| 2273.0-2273.1 | 27.2-27.8 | ++ | | | | | | |
| 2246.1-2246.4 | 33.3-34.1 | +++ | + | ++ | ++ | ++ | + | |
| 2201.0-2202.1 | 35.2-35.3 | | ++ | | | + | | |
| 2158.7-2158.9 | 22.1-22.3 | ++ | | + | | + | + | |
| 2103.7-2103.9 | 31.1-31.6 | +++ | + | ++ | ++ | ++ | ++ | |
| 2085.7-2085.9 | 31.2-31.6 | ++ | + | | ++ | | + | |
| 1907.8-1807.9 | 36.5-36.6 | +++ | ++ | | | | | |
| 1900.8-1900.9 | 20.1-20.3 | + | ++ | | | | | |
| 1879.7-1880.8 | 18.6-18.9 | + | | | | | | +++ |
| 1858.8-1858.9 | 18.7-19.3 | ++ | + | | | | + | |
| 1775.0-1775.2 | 33.6-33.8 | | | + | ++ | + | | |
| 1744.7-1744.9 | 18.7-19.1 | | + | ++ | + | + | + | |
| 1738.8-1738.9 | 29.4-30.3 | +++ | +++ | +++ | +++ | ++ | + | |
| 1696.7-1696.9 | 28.3-29.0 | + | +++ | +++ | +++ | +++ | ++ | |
| 1604.7-1604.6 | 23.8-24.0 | | | + | | ++ | + | |
| 1583.6-1583.8 | 28.6-29.1 | | + | + | ++ | + | + | |
| 1530.2-1530.6 | 25-25.4 | ++ | + | | + | | | |
| 1465.6-1465.8 | 25.2-25.9 | +++ | +++ | ++ | ++ | ++ | ++ | |
| 1171.4-1171.6 | 27.9-28.4 | +++ | + | ++ | | ++ | +++ | |
| 1098.5-1097.6 | 21.0-21.3 | + | | | | | | ++ |
| 1014.5-1014.6 | 22.5-22.7 | ++ | | ++ | + | + | ++ | |
| 985.4-985.5 | 28.0-28.2 | + | + | ++ | + | ++ | ++ | |
| 907.9-908.4 | 23.4-23.8 | + | ++ | + | | ++ | + | |
| 901.4-901.5 | 22.5-22.7 | | + | | + | +++ | + | |
| 884.4-884.4 | 23.5-23.6 | ++ | | | + | | + | |
| 881.6-881.9 | 25.5-26.0 | ++ | | + | | | | |
| 862.5-862.6 | 27.0-27.4 | ++ | | + | | + | | |
| 856.3-856.4 | 21.1-21.5 | +++ | +++ | ++ | +++ | +++ | +++ | + |
| 832.1-832.4 | 30.9-31.4 | | + | + | | + | + | |
| 826.4-826.5 | 22.7-22.7 | | | | | | | ++ |
| 824.4-824.5 | 20.8-21.1 | +++ | +++ | ++ | ++ | +++ | +++ | |
| 821.4-821.4 | 23.1-23.3 | | | | + | | + | |
| 815.3-815.3 | 17.7-18.0 | +++ | +++ | +++ | +++ | +++ | +++ | |
| 782.3-782.5 | 22.5-22.6 | | | | | | | +++ |
| 771.3-771.4 | 23.4-23.8 | ++ | +++ | +++ | +++ | +++ | +++ | |
| 728.2-728.4 | 17.6-17.9 | +++ | +++ | ++ | +++ | +++ | +++ | +++ |
| 711.3-711.4 | 20.8-21.1 | +++ | +++ | ++ | +++ | +++ | +++ | |
| 709.3-709.4 | 21.2-21.5 | +++ | +++ | ++ | +++ | ++ | ++ | |
| 694.4-694.4 | 22.2-22.2 | | | | | | | ++ |
| 641.2-641.3 | 17.7-17.9 | ++ | | | | | | |
| 606.3-606.4 | 21.6-21.8 | | | + | +++ | + | + | ++ |
| 582.3-582.6 | 18.8-18.8 | ++ | | | | | | |
| 569.3-569.4 | 21.6-21.7 | | | | | | | +++ |
| 565.1-565.1 | 19.2-19.2 | | | | | | | ++ |
| 562.3-562.4 | 21.3-21.4 | | | | | | | +++ |
| 525.3-525.3 | 21.4-21.4 | | | | | | | ++ |
| 518.3-518.4 | 21.0-21.1 | | | | | | | ++ |

Observed mass and elution time ranges are shown.
Number of + symbols indicate #/3 samples mass appeared in.
Only masses that observed in >1 repetition/sample are shown.

TABLE 9

Unidentified masses in FD formulation lyophilized without AH.

| Observed Mass | Elution Time | Stock | FD 0 wk | FD 4 wk 4° C. | FD 4 wk 40° C. | FD 15 wk 4° C. | FD 15 wk 40° C. | FD 26 wk 40° C. |
|---|---|---|---|---|---|---|---|---|
| 2662.1-2662.3 | 24.4-24.5 | | | | + | | ++ | |
| 2597.9-2598.1 | 24.2-24.5 | + | | | | | | ++ |
| 2460.2-2460.4 | 33.7-33.9 | | + | ++ | + | + | + | + |
| 2431.7-2431.9 | 24.7-24.8 | | | | | + | ++ | |
| 2359.2-2359.5 | 33.3-33.8 | + | + | | | | ++ | |
| 2246.1-2246.3 | 33.3-33.8 | +++ | | | ++ | + | | |
| 2224.2-2224.5 | 26.2-26.5 | ++ | | | | | | |
| 2158.7-2158.9 | 22.0-22.3 | ++ | | ++ | ++ | | | |

TABLE 9-continued

Unidentified masses in FD formulation lyophilized without AH.

| Observed Mass | Elution Time | Stock | FD 0 wk | FD 4 wk 4° C. | FD 4 wk 40° C. | FD 15 wk 4° C. | FD 15 wk 40° C. | FD 26 wk 40° C. |
|---|---|---|---|---|---|---|---|---|
| 2103.7-2103.9 | 31.1-31.6 | +++ | +++ | +++ | +++ | + | + | + |
| 2085.6-2085.9 | 31.1-31.6 | + | +++ |  | + | + | + |  |
| 2032.2-2033.0 | 26.2-26.6 |  |  |  | ++ |  | + |  |
| 1997.2-1997.9 | 33.6-34.4 |  | + |  |  |  | ++ |  |
| 1957.9-1958.0 | 20.3-20.5 |  |  |  |  |  |  | +++ |
| 1900.8-1901 | 20.0-20.3 | + | +++ | + | ++ | +++ | + | + |
| 1905.7-1895.9 | 23.2-23.2 |  |  |  |  |  |  | ++ |
| 1879.8-1880.0 | 18.5-19.2 |  |  | ++ |  | ++ | + | + |
| 1874.8-1874.9 | 22.7-23.6 |  |  |  |  |  | ++ |  |
| 1858.9-1858.9 | 18.9-19.3 | ++ |  | + |  |  |  |  |
| 1852.1-1852.7 | 30.3-32.4 |  |  | + | + | + | ++ |  |
| 1826.7-1827.0 | 21.7-21.8 |  | ++ |  |  |  | + |  |
| 1807.8-1807.9 | 36.5-36.7 | +++ | ++ |  |  | ++ |  |  |
| 1765.9-1765.9 | 25.7-25.7 |  |  | ++ |  |  |  |  |
| 1738.7-1738.9 | 29.4-30.3 | +++ | +++ | +++ | +++ | +++ | +++ |  |
| 1696.8-1697.0 | 28.3-28.8 | + | +++ | +++ | +++ | +++ | ++ | ++ |
| 1663.2-1663.5 | 31.0-31.3 | ++ | + |  |  |  |  |  |
| 1583.7-1584.0 | 25.8-28.9 |  | + | + | + | ++ | + |  |
| 1573.1-1573.3 | 33.5-33.7 | + |  | + |  | ++ |  |  |
| 1541.7-1541.8 | 19.8-20.1 |  |  |  |  | ++ | ++ | + |
| 1530.3-1530.6 | 25.0-25.5 | ++ |  |  | + |  |  | + |
| 1497.5-1498.0 | 33.1-33.7 | + |  |  |  | + |  | +++ |
| 1465.6-1465.8 | 25.2-25.8 | +++ | ++ | +++ | ++ | +++ | ++ | + |
| 1375.7-1375.8 | 23.8-24.4 | ++ |  |  |  |  |  |  |
| 1331.7-1332.2 | 33.4-33.7 |  |  | + | + | ++ |  |  |
| 1171.5-1171.6 | 27.9-28.4 | +++ | ++ |  | ++ |  | +++ |  |
| 1120.4-1120.5 | 21.1-21.2 |  |  |  |  |  |  | ++ |
| 1097.5-1097.7 | 20.9-21.2 |  | ++ | ++ | + | + | +++ | + |
| 1014.3-1014.5 | 22.5-22.7 | ++ | + |  |  | ++ |  | + |
| 985.4-985.5 | 27.9-28.4 | + | +++ | ++ | ++ |  | +++ |  |
| 968.2-968.3 | 32.3-33.1 | ++ |  |  |  |  |  | + |
| 950.3-950.5 | 17.6-18.0 | + | ++ | ++ | + |  |  | ++ |
| 935.3-935.3 | 33.0-33.3 |  |  |  |  |  | ++ |  |
| 922.3-922.5 | 22.2-22.4 | +++ | + |  |  |  |  |  |
| 901.4-901.5 | 22.6-22.7 |  | ++ | ++ | ++ | + | ++ |  |
| 889.7-889.9 | 24.6-26.7 |  |  |  |  |  | ++ |  |
| 884.4-884.5 | 23.3-23.7 |  | + | + | +++ | + | + | +++ |
| 881.8-882.0 | 25.5-26.1 | ++ |  | ++ | ++ |  |  |  |
| 862.5-862.5 | 27.0-27.1 | ++ |  |  |  |  |  |  |
| 856.3-856.4 | 21.1-21.5 | ++ | ++ | ++ | +++ | +++ | +++ | ++ |
| 824.4-824.5 | 20.8-21.1 | +++ | ++ | +++ | +++ | +++ | +++ |  |
| 821.3-821.4 | 23.1-23.3 |  | + | ++ | + | + | + |  |
| 815.3-815.4 | 17.5-18.0 | +++ | +++ | ++ | ++ | +++ | +++ | +++ |
| 771.3-771.4 | 23.4-34.5 | ++ | +++ | ++ | ++ | ++ | ++ | +++ |
| 750.3-750.4 | 23.1-23.2 | + |  | + |  | + | ++ |  |
| 739.3-739.4 | 23.4-23.5 |  | + | ++ | + | + | ++ |  |
| 728.2-728.3 | 17.6-18.0 | +++ | +++ | +++ | +++ | +++ | +++ | ++ |
| 711.3-711.4 | 20.8-21.1 | +++ | +++ | ++ | ++ | ++ | +++ |  |
| 709.3-709.4 | 21.2-23.1 | +++ | +++ | +++ | ++ | ++ | +++ |  |
| 658.3-658.4 | 23.5-23.7 |  |  |  | + | ++ |  |  |
| 657.3-657.6 | 33.3-34.0 |  |  | + |  |  | ++ |  |
| 641.2-641.3 | 17.7-17.9 | ++ |  | + |  | + |  |  |
| 606.3-606.4 | 21.5-21.9 |  |  | +++ | + | + | +++ | ++ |
| 582.3-582.6 | 18.8-18.8 | ++ |  |  |  |  |  |  |
| 562.4-562.4 | 21.3-21.6 |  |  |  |  | + |  | ++ |
| 525.2-525.4 | 21.3-21.4 |  |  |  |  |  |  | ++ |
| 453.2-453.3 | 19.8-19.9 |  |  |  |  |  |  | +++ |

Observed mass and elution time ranges are shown.
Number of + symbols indicate #/3 samples mass appeared in.
Only masses that observed in >1 repetition/sample are shown.

TABLE 10

Unidentified masses in SFD formulation lyophilized without AH.

| Observed Mass | Elution Time | Stock | SFD 0 wk | SFD 4 wk 4° C. | SFD 4 wk 40° C. | SFD 15 wk 4° C. | SFD 15 wk 40° C. | SFD 26 wk 40° C. |
|---|---|---|---|---|---|---|---|---|
| 2778.0-2778.2 | 30.2-31.2 |  | ++ | + | ++ |  | ++ | + |
| 2751.0-2751.5 | 35.3-35.6 |  | + |  | ++ |  |  |  |
| 2741.0-2741.3 | 21.7-22.0 | + | ++ | + |  | + | + | + |
| 2705.6-2706.2 | 33.4-33.5 | + | ++ |  |  |  |  |  |

TABLE 10-continued

Unidentified masses in SFD formulation lyophilized without AH.

| Observed Mass | Elution Time | Stock | SFD 0 wk | SFD 4 wk 4° C. | SFD 4 wk 40° C. | SFD 15 wk 4° C. | SFD 15 wk 40° C. | SFD 26 wk 40° C. |
|---|---|---|---|---|---|---|---|---|
| 2663.3-2663.4 | 33.3-34.1 |  | ++ | + | + | + | + |  |
| 2553.1-2553.2 | 31.6-31.6 |  |  |  |  |  |  | ++ |
| 2516.0-2516.1 | 31.4-31.5 | + |  |  |  |  |  | ++ |
| 2494.9-2495.1 | 31.0-31.6 | + | + |  | + | + |  | + |
| 2451.9-2452.1 | 27.6-28.1 |  | ++ | + | + | ++ | ++ |  |
| 2431.6-2432.3 | 24.6-25.2 |  | + | + |  |  | ++ | + |
| 2408.0-2408.1 | 23.8-24.6 |  |  |  | ++ |  |  |  |
| 2359.1-2359.4 | 33.3-34.0 | + |  |  | ++ |  | ++ |  |
| 2246.0-2246.3 | 33.3-33.9 | +++ |  | + |  | +++ | ++ |  |
| 2224.2-2224.8 | 26.2-26.6 | ++ |  |  |  |  |  | + |
| 2177.3-2177.9 | 23.6-23.7 |  |  |  |  | +++ |  |  |
| 2158.7-2158.8 | 22.1-22.3 | ++ |  | + | + | + |  |  |
| 2103.7-2103.9 | 31.1-31.9 | ++ | +++ | ++ | ++ | ++ | ++ |  |
| 2085.8-2085.8 | 31.2-31.5 | ++ |  | ++ |  | + |  |  |
| 2032.8-2033.0 | 26.2-26.2 |  | ++ |  |  |  |  |  |
| 1958.0-1958.0 | 20.5-20.5 |  |  |  |  |  |  | ++ |
| 1900.8-1900.9 | 20.1-20.2 | + | + | ++ | + |  |  |  |
| 1895.9-1895.9 | 23.3-23.4 |  |  |  |  |  |  | ++ |
| 1879.7-1880.0 | 18.6-18.9 |  |  | + |  | ++ | ++ | ++ |
| 1858.9-1858.9 | 19.1-19.3 | ++ |  |  |  |  |  |  |
| 1807.8-1807.9 | 36.5-36.9 | +++ |  | + | + |  |  |  |
| 1738.8-1738.9 | 29.4-30.4 | +++ | +++ | +++ | +++ | +++ | +++ | + |
| 1714.8-1714.8 | 23.0-23.0 |  |  |  |  |  |  | ++ |
| 1696.7-1687.0 | 28.3-29.0 | + | +++ | +++ | ++ | +++ | ++ | +++ |
| 1663.2-1663.5 | 31.0-31.0 | ++ |  |  |  |  |  |  |
| 1583.8-1583.9 | 28.5-29.0 |  | ++ | ++ |  | + | ++ |  |
| 1573.1-1573.4 | 33.4-33.7 | + | + |  |  | ++ |  |  |
| 1541.7-1541.7 | 20.0-20.2 |  |  |  |  | + | ++ |  |
| 1465.6-1465.8 | 25.2-25.9 | +++ | + | +++ | ++ | +++ | ++ | + |
| 1375.7-1375.8 | 23.8-24.4 | ++ |  |  |  |  |  |  |
| 1171.5-1171.6 | 27.9-28.7 | +++ | ++ | + | ++ | ++ | + |  |
| 1097.5-1097.7 | 21.1-21.4 |  |  |  | + | ++ |  | + |
| 1014.5-1014.6 | 22.5-22.8 | ++ | + |  |  | + | + |  |
| 985.4-985.5 | 28.1-28.5 | + | +++ | ++ | +++ | ++ | ++ |  |
| 972.3-972.3 | 17.8-18.0 |  |  |  |  |  |  | ++ |
| 968.2-968.2 | 32.2-33.1 | ++ |  |  |  |  |  |  |
| 950.3-950.5 | 17.7-18.0 | + |  | + | + | + |  | +++ |
| 901.4-901.5 | 22.5-22.8 |  | + | +++ | + | ++ | ++ |  |
| 889.4-889.9 | 25.0-26.6 |  | ++ | + | ++ |  | + |  |
| 884.4-884.6 | 23.5-23.6 | ++ | + | + | ++ | + |  |  |
| 881.7-881.9 | 25.5-26.0 | ++ | + | + |  |  |  |  |
| 862.5-862.5 | 27.0-27.1 | ++ |  |  |  |  |  |  |
| 856.3-856.4 | 21.1-21.4 | +++ | ++ | ++ | +++ | ++ | +++ | ++ |
| 847.5-847.9 | 26.2-26.8 | + |  |  | + | ++ |  |  |
| 832.0-832.4 | 31.2-31.5 |  | + |  |  |  | ++ |  |
| 824.3-824.5 | 20.8-21.0 | +++ | +++ | +++ | +++ | +++ | ++ |  |
| 815.3-815.4 | 17.6-18.0 | ++ | +++ | +++ | +++ | +++ | ++ | +++ |
| 771.3-771.4 | 23.4-23.8 | ++ | +++ | ++ | ++ | ++ | ++ | +++ |
| 768.1-768.4 | 24.5-25.3 |  |  | ++ |  | + |  |  |
| 750.0-750.4 | 21.5-23.2 | + |  |  |  | ++ |  | + |
| 739.3-739.4 | 23.4-23.5 |  | ++ | ++ |  |  |  |  |
| 728.3-728.4 | 17.6-18.0 | ++ | +++ | +++ | +++ | +++ | +++ | + |
| 711.3-711.4 | 20.8-21.2 | +++ | +++ | ++ | +++ | +++ | +++ |  |
| 709.3-709.4 | 21.2-23.3 | +++ | +++ | ++ | ++ | ++ | ++ |  |
| 666.5-666.8 | 32.2-32.6 | + |  |  | + |  | ++ |  |
| 658.2-658.3 | 23.5-23.8 |  |  |  | ++ | + |  | + |
| 641.2-641.3 | 17.7-17.9 | ++ |  |  |  |  | + |  |
| 634.4-634.5 | 20.1-20.3 |  |  |  | ++ |  | + |  |
| 619.9-620.4 | 18.5-19.1 | + |  | + |  |  | ++ |  |
| 606.3-606.4 | 21.5-21.9 |  |  | +++ | ++ |  | +++ | +++ |
| 582.2-582.6 | 18.8-19.0 | ++ |  | + |  | + |  |  |
| 580.2-580.3 | 18.8-19.2 |  |  |  |  | ++ | + |  |
| 569.3-569.4 | 21.6-21.7 |  |  |  |  |  |  | ++ |
| 562.3-562.4 | 21.3-21.7 |  |  | + | ++ | + | + | ++ |
| 518.3-518.3 | 21.0-21.2 |  |  |  |  | + |  | ++ |
| 493.3-493.4 | 45.8-45.9 |  |  |  |  |  |  | +++ |
| 474.3-474.3 | 20.6-20.6 |  |  |  |  |  |  | ++ |
| 453.2-453.3 | 19.8-19.9 |  |  |  |  |  |  | ++ |

Observed mass and elution time ranges are shown.
Number of + symbols indicate #/3 samples mass appeared in.
Only masses that observed in >1 repetition/sample are shown.

The potential chemical degradation of rBoNTE (Hc) in the formulations was monitored by studying the unidentified mass lists. Degradation of asparagine side-chain amide groups in proteins can occur via a succinimide intermediate to form an aspartic acid, or isoaspartic acid, carboxylic acid side-chain with a resultant change in mass of about +1.0 m/z. Degradation of methionine in proteins can occur via oxidation to methionine sulfoxide with a resultant change in mass of about +16.0 m/z. Tables 7-10 list the unidentified peptides observed for four rBoNTE (Hc) formulations. Tables 7 and 8 list the unidentified peptides observed for the FD and SFD formulations, respectively, for samples lyophilized with AH while Tables 9 and 10 list the unidentified peptides in FD and SFD preparations without adjuvant. Only peptide masses that occur more than once in any sample with similar residence times (range of ~2 minutes) are presented. Many of the unidentified peptides appear in most lyophilized formulation and in the stock preparation of the antigen. These include peptides with masses around 2103.8, 824.4, 815.4, and 771.3 Da. There are a number of masses that occur predominantly in the stock protein (i.e. masses around 2273.1, 1858.9, or 862.6 Da), that only occur in the lyophilized preparations (i.e. masses around 2779.1, 2451.9, or 901.4 Da), or that only show up later during incubation (i.e. mass around 606.4 Da).

Previously, Estey et al. detected oxidation and deamidation in rBoNTE(Hc) formulations. (Estey, T., C. Vessely, T. W. Randolph, I. Henderson, L. S. Jones, R. Nayar and J. F. Carpenter (In Preparation). The chemical degradation of a trivalent recombinant protein vaccine against botulinum neurotoxin by lysc peptide mapping and MALDI-TOF mass spectrometry). However, in the present study there are no obvious assignments to masses representing +16.0 m/z or +1.0 m/z changes to known peptides.

Immunogenicity of rBoNTE(Hc) Vaccines

The immunogenicity of the liquid rBoNTE(Hc) vaccines was tested at 0 and 15 weeks following storage at 4° C. and 30° C. for samples stored in the presence of AH (FIG. 25) and absence of AH (FIG. 26), where AH was added prior to injection.

Figure 25:
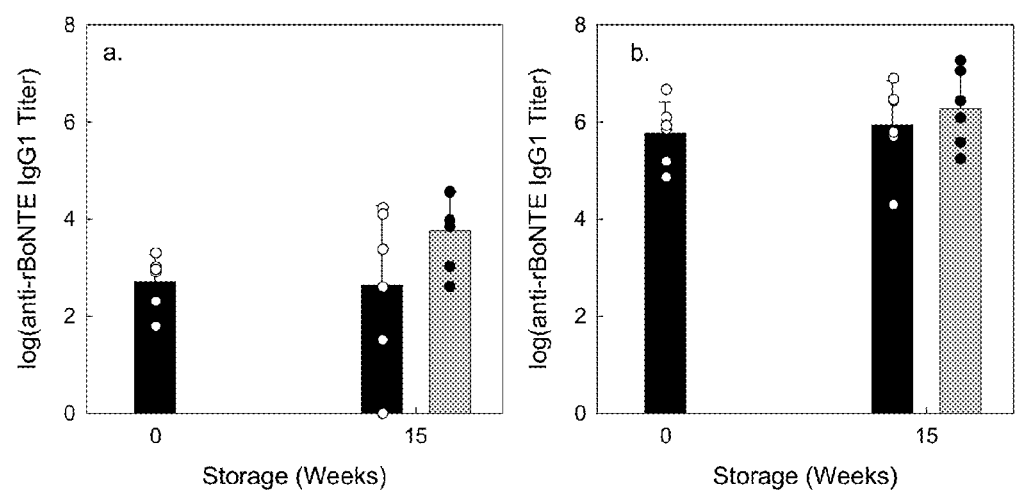

FIG. 25 shows (a.) primary and (b.) secondary IgG1 responses to liquid rBoNTE(Hc) vaccines formulated with AH. Samples were stored at 4° C. (black bars with white markers) and 30° C. (gray bars with black markers). Circles represent individual samples, with the bars representing the average of six replicates with standard deviations given with the error bars.

Figure 26:
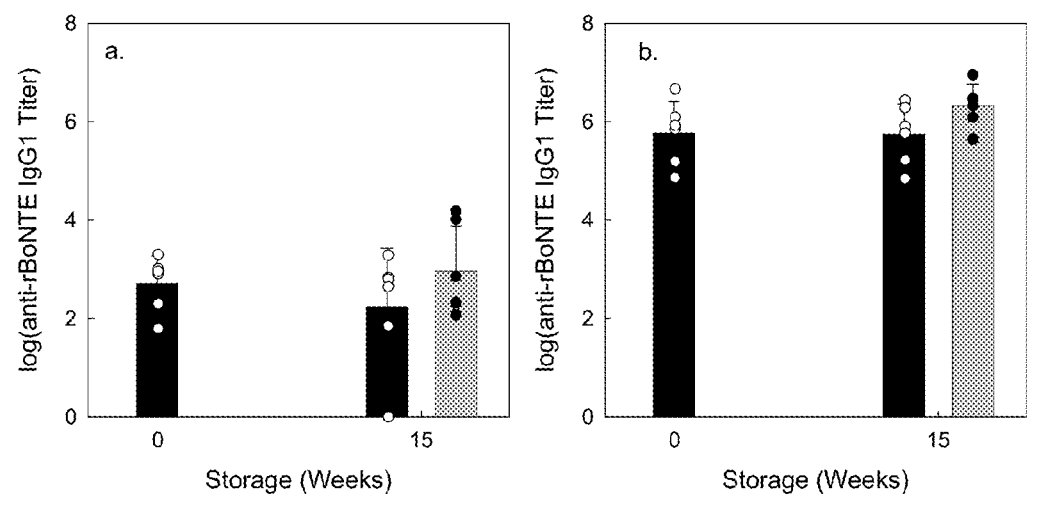

FIG. 26 shows (a.) primary and (b.) secondary IgG1 responses to liquid rBoNTE(Hc) vaccines formulated without AH. AH was added prior to injection. Samples were stored at 4° C. (black bars with white markers) and 30° C. (gray bars with black markers). Circles represent individual samples, with the bars representing the average of six replicates with standard deviations given with the error bars.

Following two injections (secondary response) the anti-rBoNTE(Hc) IgG1 titer is approximately three orders of magnitude larger than that following one injection (primary response). However, the incubation temperature or the presence of AH during storage did not affect the antibody titers to these vaccines.

Lyophilized rBoNTE(Hc) samples were tested at weeks 0, 15, and 28 following storage at 4° C. and 40° C. AH was added to sample lyophilized without AH prior to injection.

Figure 27:
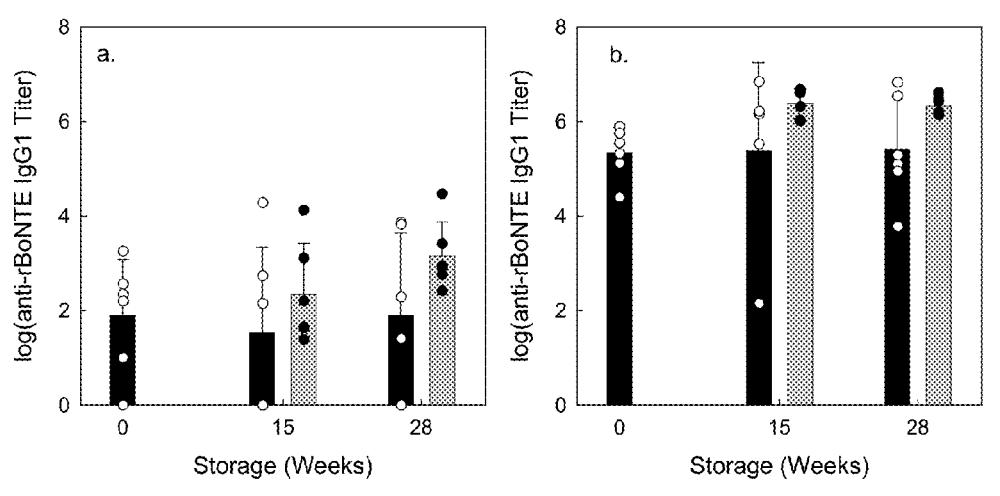

FIG. 27 shows (a.) primary and (b.) secondary IgG1 responses to FD rBoNTE(Hc) vaccines formulated with AH. Samples were stored at 4° C. (black bars with white markers) and 40° C. (gray bars with black markers). Circles represent individual samples, with the bars representing the average of six replicates with standard deviations given with the error bars.

Figure 28:
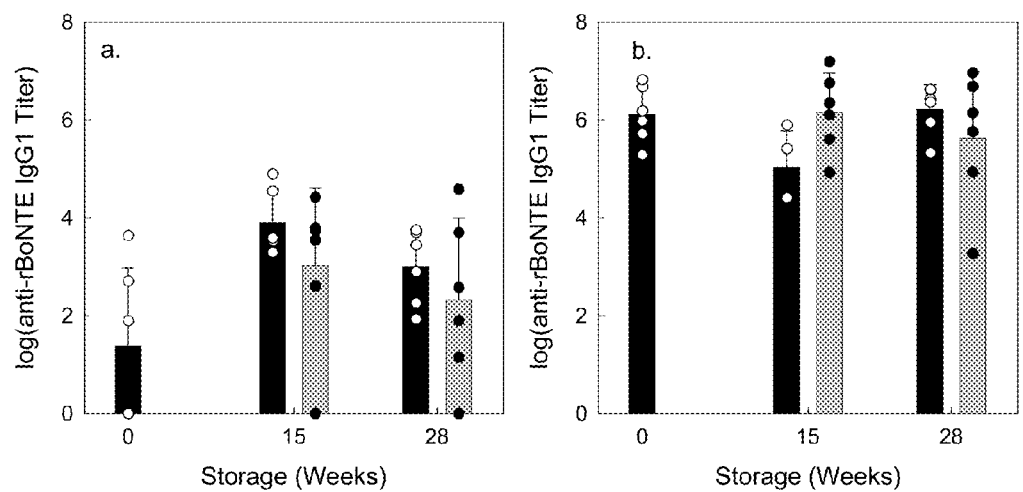
FIG. 28 shows (a.) primary and (b.) secondary IgG1 responses to FD rBoNTE(Hc) vaccines formulated without AH. AH was added during reconstitution. Samples were stored at 4° C. (black bars with white markers) and 40° C. (gray bars with black markers).

FIG. 28 shows (a.) primary and (b.) secondary IgG1 responses to FD rBoNTE(Hc) vaccines formulated without AH. AH was added during reconstitution. Samples were stored at 4° C. (black bars with white markers) and 40° C. (gray bars with black markers). Circles represent individual samples, with the bars representing the average of six replicates with standard deviations given with the error bars.

Figure 29:
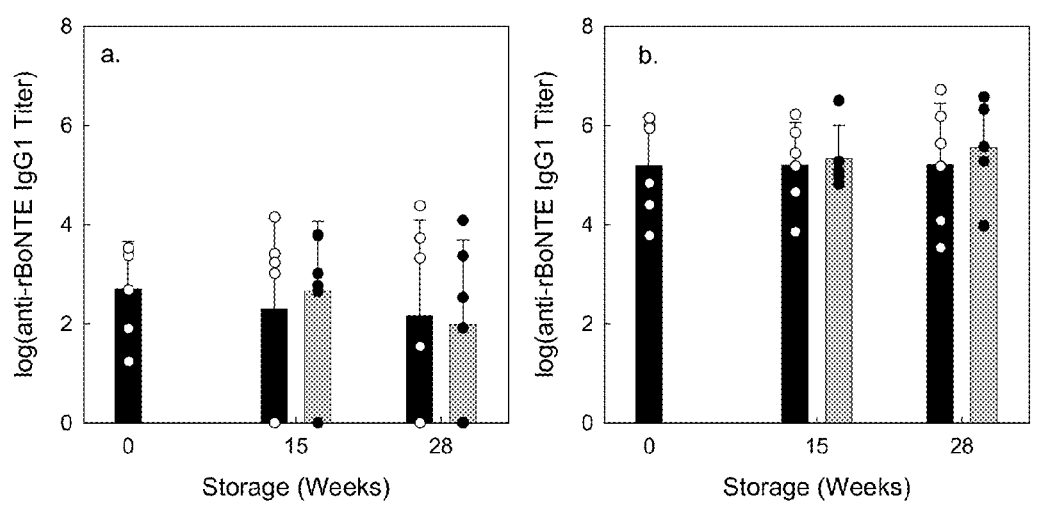

FIG. 29 shows (a.) primary and (b.) secondary IgG1 responses to SFD rBoNTE(Hc) vaccines formulated with AH. Samples were stored at 4° C. (black bars with white markers) and 40° C. (gray bars with black markers). Circles represent individual samples, with the bars representing the average of six replicates with standard deviations given with the error bars.

Figure 30:
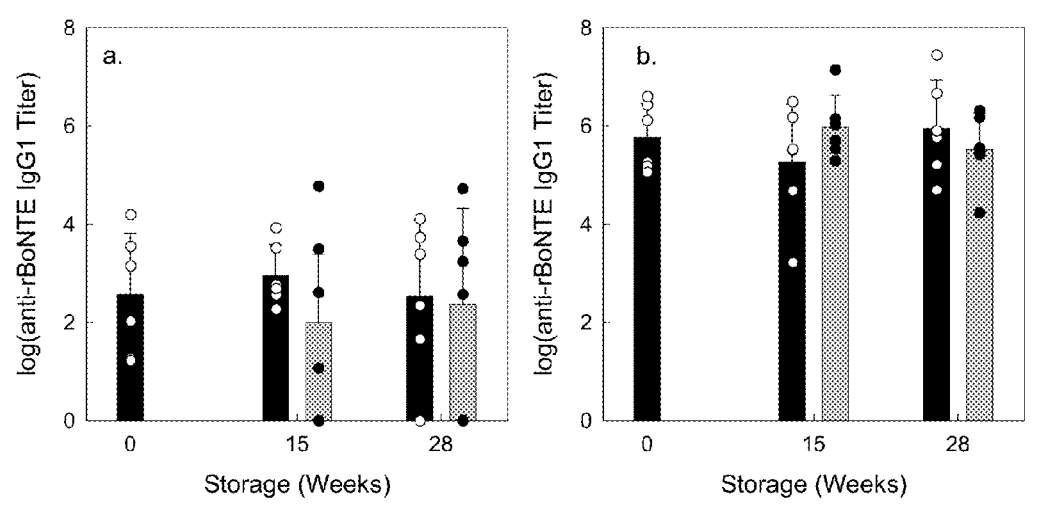

FIG. 30 shows (a.) primary and (b.) secondary IgG1 responses to SFD rBoNTE(Hc) vaccines formulated without AH. AH was added during reconstitution. Samples were stored at 4° C. (black bars with white markers) and 40° C. (gray bars with black markers). Circles represent individual samples, with the bars representing the average of six replicates with standard deviations given with the error bars.

The immunogenicities of FD vaccines lyophilized with or without AH (FIGS. 27 and 28, respectively) and of SFD vaccines lyophilized with or without AH (FIGS. 29 and 30, respectively) were also independent of storage temperature, and produced similar anti-rBoTNE(Hc) titers as the liquid vaccines. Small changes in the PSD of the adjuvant and the MS characterization were seen, while large changes in the ability to elute the antigen from the adjuvant were observed. However, these changes appear to occur on a longer time scale than previous studies with this antigen in a liquid formulation, and do not appear to affect the immunogenicity or potency of these vaccines.

Potency of rBoNTE(Hc) Vaccines

The potencies of two rBoNTE(Hc) vaccine formulations were tested in a murine model. A liquid vaccine (10 w/v % trehalose stored with AH) and a SFD vaccine (lyophilized with AH) were tested for their abilities to protect against a toxin challenge. ED-50 level, the dose required for 50% survival, was calculated for each sample with data presented in Table 11. The confidence intervals overlap for all samples.

TABLE 11

ED-50 values and 95% confidence intervals of data from potency assay of liquid and SFD vaccines stored at 4° C. All samples were stored in the presence of AH.

| Vaccine | ED50 | 95% Confidence Limits |
| --- | --- | --- |
| Liquid Vaccine-0 weeks | 170 ng | 71-375 ng |
| Liquid Vaccine-3 weeks | 94 ng | 0.47-649 ng |
| Liquid Vaccine-15 weeks | 239 ng | 87-602 ng |
| SFD Vaccine-0 weeks | 219 ng | 85-549 ng |
| SFD Vaccine-3 weeks | 249 ng | 117-539 ng |
| SFD Vaccine-15 weeks | 486 ng | 205 ng-1.29 µg |

Figure 31:
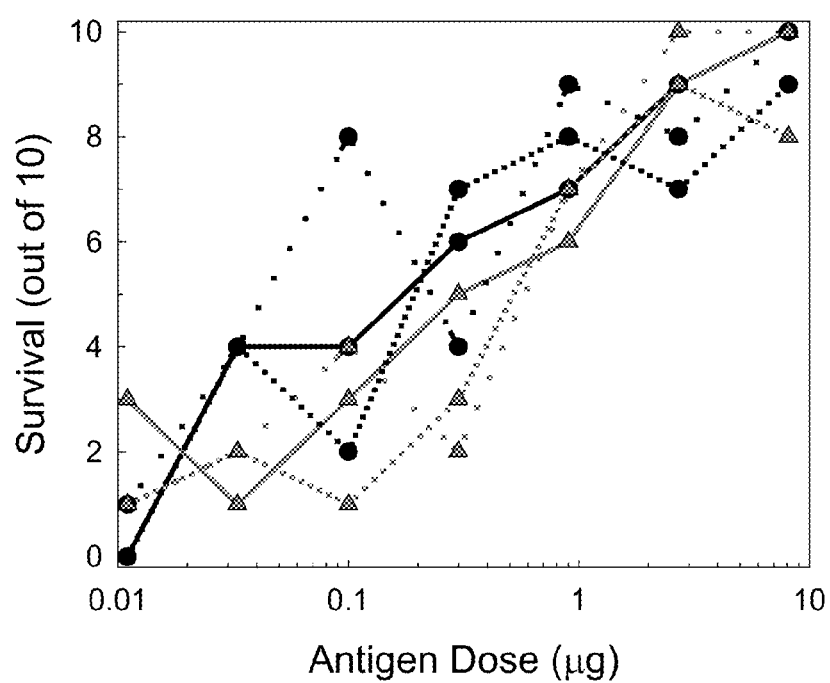
FIG. 31 shows a potency assay for liquid (black circles) and SFD (gray triangles) rBoNTE(Hc) vaccines. Survival after a challenge with BoNTE to mice immunized with rBoNTE (Hc) vaccines with AH previously stored for 0 weeks (solid lines), 3 weeks (dashed lines) or 15 weeks (dotted lines) at 4° C. prior to administration.

FIG. 31 shows potency assay data for liquid (black circles) and SFD (gray triangles) rBoNTE(Hc) vaccines. Survival after a challenge of 1000 mouse intraperitoneal lethal doses ($MIPLD_{50}$) of BoNTE to ten mice each group immunized with rBoNTE(Hc) vaccines previously stored 0 weeks (solid lines), 3 weeks (dashed lines) or 15 weeks (dotted lines) at 4° C. prior to administration is shown. All samples were stored in the presence of AH.

The freeze-dried and spray freeze-dried vaccines had equivalent immunogenicity as the liquid formulations when tested in a murine model whether or not they were lyophilized with adjuvant. The spray freeze-dried vaccine also exhibited a potency that was statistically equivalent to that of the liquid vaccine, both initially following lyophilization and after 3 and 15 weeks of storage. Liquid and SFD preparations were equally potent against botulinum neurotoxin challenges.

The present invention teaches stable vaccine adjuvant formulation conditions which cause minimal AH aggregation during lyophilization, including use of a high concentration of trehalose and faster cooling rates. The SFD samples do not exhibit aggregates, while the FD samples have about 20% aggregates following lyophilization and reconstitution. There is a small increase in the percentage of aggregates for the FD samples during storage, which is more pronounced for samples stored at 40° C. as compared to 4° C., and may be due to residual water remaining following lyophilization.

Lyophilized vaccine preparations prepared under these conditions maintain immunogenicity during storage Immediately following lyophilization, the FD and SFD preparations are equally immunogenic as the liquid preparations of vaccines in a murine model. This is independent on whether the AH is added prior to lyophilization or as part of the reconstitution buffer. Following 15 weeks of storage, the liquid and lyophilized vaccines remain immunogenic, with no change in the anti-rBoNTE titers. Following 26 weeks of storage, all of the lyophilized formulations have unchanged titers from the unaged samples, even when stored at 40° C., thus indicating that the changes observed in the desorption properties and the changes observed with LCMS do not have a significant effect on the immunogenicity of these vaccines.

Although immunogenicity does not always confer protection for vaccines, a potency assay shows both liquid and SFD vaccines of the present invention, when stored in the presence of AH at 4° C. have similar potency at all time points, with only insignificant differences in ED50 values.

We claim:

1. A freeze dried composition comprising:
   a. an aluminum-salt adjuvant,
   b. a glass-forming agent,
   c. a buffer salt, and
   d. a recombinant antigen, wherein the antigen is selected from the group consisting of toxins and viruses.

2. The composition of claim 1, wherein the aluminum-salt adjuvant is selected from the group consisting of aluminum hydroxide and aluminum phosphate.

3. The composition of claim 1, wherein the glass-forming agent is trehalose.

4. The composition of claim 1, wherein the buffer salt is selected from one or more of the group consisting of sodium succinate, potassium succinate, histidine, sodium phosphate and potassium phosphate.

5. The composition of claim 1, wherein the antigen is recombinant ricin A chain.

6. The composition of claim 1, wherein the antigen is recombinant anthrax protective antigen.

7. The composition of claim 1, wherein the antigen is recombinant human papillomavirus (HPV) antigen.

8. A method of controlling particle size in an adjuvant-bound dried vaccine composition, the method comprising:

a. selecting one or more each of an aluminum-salt adjuvant, a buffer system, a glass-forming agent and an antigen;

b. blending the adjuvant, the glass-forming agent and the antigen in the buffer system to create a liquid vaccine formulation;

c. cooling the liquid vaccine formulation rapidly to a frozen state to create a frozen vaccine formulation; and d. lyophilizing the frozen vaccine formulation to create a dried vaccine composition;

wherein following dilution of the dried vaccine composition with an aqueous diluent to form a reconstituted vaccine composition the mean particle diameter of the reconstituted vaccine composition is less than 10 micrometers.

9. The method of claim 8, wherein the one or more aluminum-salt adjuvant is selected from the group consisting of aluminum hydroxide, aluminum phosphate and aluminum sulfate.

10. The method of claim 9, wherein the aluminum-salt adjuvant is aluminum hydroxide.

11. The method of claim 8, wherein the one or more buffer system is selected from the group consisting of acetate, succinate, citrate, prolamine, carbonate, histidine, and phosphate buffer systems.

12. The method of claim 11, wherein the one or more buffer system is selected from succinate and phosphate buffer systems.

13. The method of claim 8, wherein the one or more glass-forming agent is selected from the group consisting of trehalose, sucrose, ficoll, dextran, sucrose, maltotriose, lactose, mannitol, hydroxyethyl starch, glycine, cyclodextrin, povidone and potassium salts.

14. The method of claim 8, wherein the glass-forming agent is trehalose.

15. The method of claim 14, wherein the trehalose is present in a weight to volume concentration of from about 5% to about 20% in the liquid vaccine formulation.

16. The method of claim 8, wherein the antigen is selected from the group consisting of rotavirus, foot and mouth disease virus, influenza A virus, influenza B virus, influenza C virus, H1N1, H2N2, H3N2, H5N1, H7N7, H1N2, H9N2, H7N2, H7N3, H10N7, human parainfluenza type 2, herpes simplex virus, Epstein Barr virus, varicella virus, porcine herpesvirus 1, cytomegalovirus, Lyssavirus, Poliovirus, Hepatitis A, Hepatitis B, Hepatitis C, Hepatitis E, distemper virus, venezuelan equine encephalomyelitis, feline leukemia virus, Reovirus, Respiratory syncytial virus, Lassa fever virus, polyoma tumor virus, canine parvovirus, Papilloma virus, tick borne encephalitis virus, Rinderpest virus, human rhinovirus species, Enterovirus species, Mengo virus, Paramyxovirus, avian infectious bronchitis virus, Human T-cell leukemia-lymphoma virus 1, Human immunodeficiency virus-1, Human immunodeficiency virus-2, lymphocytic choriomeningitis virus, Parovirus B19, Adenovirus, rubella virus, yellow fever virus, dengue virus, Bovine respiratory syncitial virus, Corona virus, *Bordetella pertussis, Bordetella bronchiseptica, Bordetella parapertussis, Brucella abortis, Brucella melitensis, Brucella suis, Brucella ovis, Brucella species, Escherichia coli, Salmonella* species, *salmonella typhi*, Streptococci, *Vibrio cholera, Vibrio parahaemolyticus, Shigella, Pseudomonas*, tuberculosis, avium, Bacille Calmette Guerin, *Micobacterium leprae*, Pneumococci, Staphlylococci, *Enterobacter* species, *Rochalimaia henselae, Pasterurella haemolytica, Pasterurella multocida, Chlamydia trachomatis, Chlamydia psittaci, Lymphogranuloma venereum, Treponema pallidum, Haemophilus* species, *Mycoplasma bovigenitalium, Mycoplasma pulmonis, Mycoplasma* species, *Borrelia burgdorferi, Legionalla pneumophila, Colstridium botulinum, Corynebacterium diphtheriae, Yersinia entercolitica, Rickettsia rickettsii, Rickettsia typhi, Rickettsia prowsaekii, Ehrlichia chaffeensis, Anaplasma phagocytophilum, Plasmodium falciparum, Plasmodium vivax, Plasmodium malariae*, Schistosomes, Trypanosomes, *Leishmania* species, Filarial nematodes, Trichomoniasis, Sarcosporidiasis, *Taenia saginata, Taenia solium, Leishmania, Toxoplasma gondii, Trichinella spiralis*, Coccidiosis, *Eimeria tenella, Cryptococcus neoformans, Candida albican, Apergillus fumigatus*, Coccidioidomycosis, *Neisseria gonorrhoeae*, Malaria circumsporozoite protein, Malaria merozoite protein, Trypanosome surface antigen protein, Pertussis, Alphaviruses, Adenovirus, Diphtheria toxoid, Tetanus toxoid, meningococcal outer membrane protein, Streptococcal M protein, Influenza hemagglutinin, cancer antigen, tumor antigens, toxins, exotoxins, Neurotoxins, cytokines, cytokine receptors, monokines, monokine receptors, plant pollens, animal dander, and dust mites.

* * * * *

SEQUENCE LISTING

```
<160> NUMBER OF SEQ ID NOS: 5

<210> SEQ ID NO 1
<211> LENGTH: 449
<212> TYPE: PRT
<213> ORGANISM: Artificial Sequence
<220> FEATURE:
<223> OTHER INFORMATION: C-terminal domain of heavy chain of Clostridium
      botulinum neurotoxin E

<400> SEQUENCE: 1

Met Gly Glu Ser Gln Gln Glu Leu Asn Ser Met Val Thr Asp Thr Leu
1               5                   10                  15

Asn Asn Ser Ile Pro Phe Lys Leu Ser Ser Tyr Thr Asp Asp Lys Ile
            20                  25                  30

Leu Ile Ser Tyr Phe Asn Lys Phe Phe Lys Arg Ile Lys Ser Ser Ser
        35                  40                  45

Val Leu Asn Met Arg Tyr Lys Asn Asp Lys Tyr Val Asp Thr Ser Gly
    50                  55                  60

Tyr Asp Ser Asn Ile Asn Ile Asn Gly Asp Val Tyr Lys Tyr Pro Thr
65                  70                  75                  80

Asn Lys Asn Gln Phe Gly Ile Tyr Asn Asp Lys Leu Ser Glu Val Asn
                85                  90                  95

Ile Ser Gln Asn Asp Tyr Ile Ile Tyr Asp Asn Lys Tyr Lys Asn Phe
            100                 105                 110

Ser Ile Ser Phe Trp Val Arg Ile Pro Asn Tyr Asp Asn Lys Ile Val
        115                 120                 125

Asn Val Asn Asn Glu Tyr Thr Ile Ile Asn Cys Met Arg Asp Asn Asn
    130                 135                 140

Ser Gly Trp Lys Val Ser Leu Asn His Asn Glu Ile Ile Trp Thr Leu
145                 150                 155                 160

Gln Asp Asn Ala Gly Ile Asn Gln Lys Leu Ala Phe Asn Tyr Gly Asn
                165                 170                 175

Ala Asn Gly Ile Ser Asp Tyr Ile Asn Lys Trp Ile Phe Val Thr Ile
            180                 185                 190

Thr Asn Asp Arg Leu Gly Asp Ser Lys Leu Tyr Ile Asn Gly Asn Leu
        195                 200                 205

Ile Asp Gln Lys Ser Ile Leu Asn Leu Gly Asn Ile His Val Ser Asp
    210                 215                 220

Asn Ile Leu Phe Lys Ile Val Asn Cys Ser Tyr Thr Arg Tyr Ile Gly
225                 230                 235                 240
```

```
Ile Arg Tyr Phe Asn Ile Phe Asp Lys Glu Leu Asp Glu Thr Glu Ile
                245                 250                 255

Gln Thr Leu Tyr Ser Asn Glu Pro Asn Thr Asn Ile Leu Lys Asp Phe
            260                 265                 270

Trp Gly Asn Tyr Leu Leu Tyr Asp Lys Glu Tyr Tyr Leu Leu Asn Val
        275                 280                 285

Leu Lys Pro Asn Asn Phe Ile Asp Arg Arg Lys Asp Ser Thr Leu Ser
    290                 295                 300

Ile Asn Asn Ile Arg Ser Thr Ile Leu Leu Ala Asn Arg Leu Tyr Ser
305                 310                 315                 320

Gly Ile Lys Val Lys Ile Gln Arg Val Asn Asn Ser Ser Thr Asn Asp
                325                 330                 335

Asn Leu Val Arg Lys Asn Asp Gln Val Tyr Ile Asn Phe Val Ala Ser
            340                 345                 350

Lys Thr His Leu Phe Pro Leu Tyr Ala Asp Thr Ala Thr Thr Asn Lys
        355                 360                 365

Glu Lys Thr Ile Lys Ile Ser Ser Ser Gly Asn Arg Phe Asn Gln Val
    370                 375                 380

Val Val Met Asn Ser Val Gly Asn Asn Cys Thr Met Asn Phe Lys Asn
385                 390                 395                 400

Asn Asn Gly Asn Asn Ile Gly Leu Leu Gly Phe Lys Ala Asp Thr Val
                405                 410                 415

Val Ala Ser Thr Trp Tyr Tyr Thr His Met Arg Asp His Thr Asn Ser
            420                 425                 430

Asn Gly Cys Phe Trp Asn Phe Ile Ser Glu Glu His Gly Trp Gln Glu
        435                 440                 445

Lys

<210> SEQ ID NO 2
<211> LENGTH: 450
<212> TYPE: PRT
<213> ORGANISM: Artificial Sequence
<220> FEATURE:
<223> OTHER INFORMATION: C-terminal domain of heavy chain of Clostridium
      botulinum neurotoxin C

<400> SEQUENCE: 2

Met Thr Ile Pro Phe Asn Ile Phe Ser Tyr Thr Asn Asn Ser Leu Leu
1               5                   10                  15

Lys Asp Ile Ile Asn Glu Tyr Phe Asn Asn Ile Asn Asp Ser Lys Ile
                20                  25                  30

Leu Ser Leu Gln Asn Arg Lys Asn Thr Leu Val Asp Thr Ser Gly Tyr
            35                  40                  45

Asn Ala Glu Val Ser Glu Gly Asp Val Gln Leu Asn Pro Ile Phe
    50                  55                  60

Pro Phe Asp Phe Lys Leu Gly Ser Ser Gly Glu Asp Arg Gly Lys Val
65                  70                  75                  80

Ile Val Thr Gln Asn Glu Asn Ile Val Tyr Asn Ser Met Tyr Glu Ser
                85                  90                  95

Phe Ser Ile Ser Phe Trp Ile Arg Ile Asn Lys Trp Val Ser Asn Leu
            100                 105                 110

Pro Gly Tyr Thr Ile Ile Asp Ser Val Lys Asn Asn Ser Gly Trp Ser
        115                 120                 125

Ile Gly Ile Ile Ser Asn Phe Leu Val Phe Thr Leu Lys Gln Asn Glu
    130                 135                 140
```

-continued

```
Asp Ser Glu Gln Ser Ile Asn Phe Ser Tyr Asp Ile Ser Asn Asn Ala
145                 150                 155                 160

Pro Gly Tyr Asn Lys Trp Phe Phe Val Thr Val Thr Asn Asn Met Met
                165                 170                 175

Gly Asn Met Lys Ile Tyr Ile Asn Gly Lys Leu Ile Asp Thr Ile Lys
            180                 185                 190

Val Lys Glu Leu Thr Gly Ile Asn Phe Ser Lys Thr Ile Thr Phe Glu
        195                 200                 205

Ile Asn Lys Ile Pro Asp Thr Gly Leu Ile Thr Ser Asp Ser Asp Asn
    210                 215                 220

Ile Asn Met Trp Ile Arg Asp Phe Tyr Ile Phe Ala Lys Glu Leu Asp
225                 230                 235                 240

Gly Lys Asp Ile Asn Ile Leu Phe Asn Ser Leu Gln Tyr Thr Asn Val
                245                 250                 255

Val Lys Asp Tyr Trp Gly Asn Asp Leu Arg Tyr Asn Lys Glu Tyr Tyr
            260                 265                 270

Met Val Asn Ile Asp Tyr Leu Asn Arg Tyr Met Tyr Ala Asn Ser Arg
        275                 280                 285

Gln Ile Val Phe Asn Thr Arg Arg Asn Asn Asn Asp Phe Asn Glu Gly
    290                 295                 300

Tyr Lys Ile Ile Ile Lys Arg Ile Arg Gly Asn Thr Asn Asp Thr Arg
305                 310                 315                 320

Val Arg Gly Gly Asp Ile Leu Tyr Phe Asp Met Thr Ile Asn Asn Lys
                325                 330                 335

Ala Tyr Asn Leu Phe Met Lys Asn Glu Thr Met Tyr Ala Asp Asn His
            340                 345                 350

Ser Thr Glu Asp Ile Tyr Ala Ile Gly Leu Arg Glu Gln Thr Lys Asp
        355                 360                 365

Ile Asn Asp Asn Ile Ile Phe Gln Ile Gln Pro Met Asn Asn Thr Tyr
    370                 375                 380

Tyr Tyr Ala Ser Gln Ile Phe Lys Ser Asn Phe Asn Gly Glu Asn Ile
385                 390                 395                 400

Ser Gly Ile Cys Ser Ile Gly Thr Tyr Arg Phe Arg Leu Gly Gly Asp
                405                 410                 415

Trp Tyr Arg His Asn Tyr Leu Val Pro Thr Val Lys Gln Gly Asn Tyr
            420                 425                 430

Ala Ser Leu Leu Glu Ser Thr Ser Thr His Trp Gly Phe Val Pro Val
        435                 440                 445

Ser Glu
450

<210> SEQ ID NO 3
<211> LENGTH: 434
<212> TYPE: PRT
<213> ORGANISM: Artificial Sequence
<220> FEATURE:
<223> OTHER INFORMATION: C-terminal domain of heavy chain of Clostridium
      botulinum neurotoxin A

<400> SEQUENCE: 3

Met Ser Thr Phe Thr Glu Tyr Ile Lys Asn Ile Ile Asn Thr Ser Ile
1               5                   10                  15

Leu Asn Leu Arg Tyr Glu Ser Asn His Leu Ile Asp Leu Ser Arg Tyr
            20                  25                  30

Ala Ser Lys Ile Asn Ile Gly Ser Lys Val Asn Phe Asp Pro Ile Asp
        35                  40                  45
```

Lys Asn Gln Ile Gln Leu Phe Asn Leu Glu Ser Ser Lys Ile Glu Val
     50                  55                  60

Ile Leu Lys Asn Ala Ile Val Tyr Asn Ser Met Tyr Glu Asn Phe Ser
 65                  70                  75                  80

Thr Ser Phe Trp Ile Arg Ile Pro Lys Tyr Phe Asn Ser Ile Ser Leu
                 85                  90                  95

Asn Asn Glu Tyr Thr Ile Ile Asn Cys Met Glu Asn Asn Ser Gly Trp
            100                 105                 110

Lys Val Ser Leu Asn Tyr Gly Glu Ile Ile Trp Thr Leu Gln Asp Thr
        115                 120                 125

Gln Glu Ile Lys Gln Arg Val Val Phe Lys Tyr Ser Gln Met Ile Asn
    130                 135                 140

Ile Ser Asp Tyr Ile Asn Arg Trp Ile Phe Val Thr Ile Thr Asn Asn
145                 150                 155                 160

Arg Leu Asn Asn Ser Lys Ile Tyr Ile Asn Gly Arg Leu Ile Asp Gln
                165                 170                 175

Lys Pro Ile Ser Asn Leu Gly Asn Ile His Ala Ser Asn Asn Ile Met
            180                 185                 190

Phe Lys Leu Asp Gly Cys Arg Asp Thr His Arg Tyr Ile Trp Ile Lys
        195                 200                 205

Tyr Phe Asn Leu Phe Asp Lys Glu Leu Asn Glu Lys Glu Ile Lys Asp
    210                 215                 220

Leu Tyr Asp Asn Gln Ser Asn Ser Gly Ile Leu Lys Asp Phe Trp Gly
225                 230                 235                 240

Asp Tyr Leu Gln Tyr Asp Lys Pro Tyr Tyr Met Leu Asn Leu Tyr Asp
                245                 250                 255

Pro Asn Lys Tyr Val Asp Val Asn Asn Val Gly Ile Arg Gly Tyr Met
            260                 265                 270

Tyr Leu Lys Gly Pro Arg Gly Ser Val Met Thr Thr Asn Ile Tyr Leu
        275                 280                 285

Asn Ser Ser Leu Tyr Arg Gly Thr Lys Phe Ile Ile Lys Lys Tyr Ala
    290                 295                 300

Ser Gly Asn Lys Asp Asn Ile Val Arg Asn Asn Asp Arg Val Tyr Ile
305                 310                 315                 320

Asn Val Val Val Lys Asn Lys Glu Tyr Arg Leu Ala Thr Asn Ala Ser
                325                 330                 335

Gln Ala Gly Val Glu Lys Ile Leu Ser Ala Leu Glu Ile Pro Asp Val
            340                 345                 350

Gly Asn Leu Ser Gln Val Val Val Met Lys Ser Lys Asn Asp Gln Gly
        355                 360                 365

Ile Thr Asn Lys Cys Lys Met Asn Leu Gln Asp Asn Asn Gly Asn Asp
    370                 375                 380

Ile Gly Phe Ile Gly Phe His Gln Phe Asn Asn Ile Ala Lys Leu Val
385                 390                 395                 400

Ala Ser Asn Trp Tyr Asn Arg Gln Ile Glu Arg Ser Ser Arg Thr Leu
                405                 410                 415

Gly Cys Ser Trp Glu Phe Ile Pro Val Asp Asp Gly Trp Gly Glu Arg
            420                 425                 430

Pro Leu

<210> SEQ ID NO 4
<211> LENGTH: 440
<212> TYPE: PRT

<213> ORGANISM: Artificial Sequence
<220> FEATURE:
<223> OTHER INFORMATION: C-terminal domain of heavy chain of Clostridium
      botulinum neurotoxin B

<400> SEQUENCE: 4

Met Ala Asn Lys Tyr Asn Ser Glu Ile Leu Asn Asn Ile Ile Leu Asn
1               5                   10                  15

Leu Arg Tyr Lys Asp Asn Asn Leu Ile Asp Leu Ser Gly Tyr Gly Ala
            20                  25                  30

Lys Val Glu Val Tyr Asp Gly Val Glu Leu Asn Asp Lys Asn Gln Phe
        35                  40                  45

Lys Leu Thr Ser Ser Ala Asn Ser Lys Ile Arg Val Thr Gln Asn Gln
    50                  55                  60

Asn Ile Ile Phe Asn Ser Val Phe Leu Asp Phe Ser Val Ser Phe Trp
65                  70                  75                  80

Ile Arg Ile Pro Lys Tyr Lys Asn Asp Gly Ile Gln Asn Tyr Ile His
                85                  90                  95

Asn Glu Tyr Thr Ile Ile Asn Cys Met Lys Asn Asn Ser Gly Trp Lys
            100                 105                 110

Ile Ser Ile Arg Gly Asn Arg Ile Ile Trp Thr Leu Ile Asp Ile Asn
        115                 120                 125

Gly Lys Thr Lys Ser Val Phe Phe Glu Tyr Asn Ile Arg Glu Asp Ile
    130                 135                 140

Ser Glu Tyr Ile Asn Arg Trp Phe Phe Val Thr Ile Thr Asn Asn Leu
145                 150                 155                 160

Asn Asn Ala Lys Ile Tyr Ile Asn Gly Lys Leu Glu Ser Asn Thr Asp
                165                 170                 175

Ile Lys Asp Ile Arg Glu Val Ile Ala Asn Gly Glu Ile Ile Phe Lys
            180                 185                 190

Leu Asp Gly Asp Ile Asp Arg Thr Gln Phe Ile Trp Met Lys Tyr Phe
        195                 200                 205

Ser Ile Phe Asn Thr Glu Leu Ser Gln Ser Asn Ile Glu Glu Arg Tyr
210                 215                 220

Lys Ile Gln Ser Tyr Ser Glu Tyr Leu Lys Asp Phe Trp Gly Asn Pro
225                 230                 235                 240

Leu Met Tyr Asn Lys Glu Tyr Tyr Met Phe Asn Ala Gly Asn Lys Asn
                245                 250                 255

Ser Tyr Ile Lys Leu Lys Lys Asp Ser Pro Val Gly Glu Ile Leu Thr
            260                 265                 270

Arg Ser Lys Tyr Asn Gln Asn Ser Lys Tyr Ile Asn Tyr Arg Asp Leu
        275                 280                 285

Tyr Ile Gly Glu Lys Phe Ile Ile Arg Arg Lys Ser Asn Ser Gln Ser
    290                 295                 300

Ile Asn Asp Asp Ile Val Arg Lys Glu Asp Tyr Ile Tyr Leu Asp Phe
305                 310                 315                 320

Phe Asn Leu Asn Gln Glu Trp Arg Val Tyr Thr Tyr Lys Tyr Phe Lys
                325                 330                 335

Lys Glu Glu Glu Lys Leu Phe Leu Ala Pro Ile Ser Asp Ser Asp Glu
            340                 345                 350

Leu Tyr Asn Thr Ile Gln Ile Lys Glu Tyr Asp Glu Gln Pro Thr Tyr
        355                 360                 365

Ser Cys Gln Leu Leu Phe Lys Lys Asp Glu Glu Ser Thr Asp Glu Ile
    370                 375                 380

```
Gly Leu Ile Gly Ile His Arg Phe Tyr Glu Ser Gly Ile Val Phe Glu
385                 390                 395                 400

Glu Tyr Lys Asp Tyr Phe Cys Ile Ser Lys Trp Tyr Leu Lys Glu Val
            405                 410                 415

Lys Arg Lys Pro Tyr Asn Leu Lys Leu Gly Cys Asn Trp Gln Phe Ile
            420                 425                 430

Pro Lys Asp Glu Gly Trp Thr Glu
        435                 440

<210> SEQ ID NO 5
<211> LENGTH: 432
<212> TYPE: PRT
<213> ORGANISM: Artificial Sequence
<220> FEATURE:
<223> OTHER INFORMATION: C-terminal domain of heavy chain of Clostridium
      botulinum neurotoxin F

<400> SEQUENCE: 5

Met Ser Tyr Thr Asn Asp Lys Ile Leu Ile Leu Tyr Phe Asn Lys Leu
1               5                   10                  15

Tyr Lys Lys Ile Lys Asp Asn Ser Ile Leu Asp Met Arg Tyr Glu Asn
            20                  25                  30

Asn Lys Phe Ile Asp Ile Ser Gly Tyr Gly Ser Asn Ile Ser Ile Asn
        35                  40                  45

Gly Asp Val Tyr Ile Tyr Ser Thr Asn Arg Asn Gln Phe Gly Ile Tyr
50                  55                  60

Ser Ser Lys Pro Ser Glu Val Asn Ile Ala Gln Asn Asn Asp Ile Ile
65                  70                  75                  80

Tyr Asn Gly Arg Tyr Gln Asn Phe Ser Met Ser Phe Trp Val Arg Ile
            85                  90                  95

Pro Lys Tyr Phe Asn Lys Val Asn Leu Asn Asn Glu Tyr Thr Ile Ile
            100                 105                 110

Asp Cys Ile Arg Asn Asn Asn Ser Gly Trp Lys Ile Ser Leu Asn Tyr
        115                 120                 125

Asn Lys Ile Ile Trp Thr Leu Gln Asp Thr Ala Gly Asn Asn Gln Lys
    130                 135                 140

Leu Val Phe Asn Tyr Thr Gln Met Ile Ser Ile Ser Asp Tyr Ile Asn
145                 150                 155                 160

Lys Trp Ile Phe Val Thr Ile Thr Asn Asn Arg Leu Gly Asn Ser Arg
                165                 170                 175

Ile Tyr Ile Asn Gly Asn Leu Ile Asp Glu Lys Ser Ile Ser Asn Leu
            180                 185                 190

Gly Asp Ile His Val Ser Asp Asn Ile Leu Phe Lys Ile Val Gly Cys
        195                 200                 205

Asn Asp Thr Arg Tyr Val Gly Ile Arg Tyr Phe Lys Val Phe Asp Thr
    210                 215                 220

Glu Leu Gly Lys Thr Glu Ile Glu Thr Leu Tyr Ser Asp Glu Pro Asp
225                 230                 235                 240

Pro Ser Ile Leu Lys Asp Phe Trp Gly Asn Tyr Leu Leu Tyr Asn Lys
                245                 250                 255

Arg Tyr Tyr Leu Leu Asn Leu Leu Arg Thr Asp Lys Ser Ile Thr Gln
            260                 265                 270

Asn Ser Asn Phe Leu Asn Ile Asn Gln Gln Arg Gly Val Tyr Gln Lys
        275                 280                 285

Pro Asn Ile Phe Ser Asn Thr Arg Leu Tyr Thr Gly Val Glu Phe Ile
    290                 295                 300
```

```
Ile Arg Lys Asn Gly Ser Thr Asp Ile Ser Asn Thr Asp Asn Phe Val
305                 310                 315                 320

Arg Lys Asn Asp Leu Ala Tyr Ile Asn Val Val Asp Arg Asp Val Glu
            325                 330                 335

Tyr Arg Leu Asn Ala Asp Ile Ser Ile Ala Lys Pro Glu Lys Ile Ile
            340                 345                 350

Lys Leu Ile Arg Thr Ser Asn Ser Asn Asn Ser Leu Gly Gln Ile Ile
        355                 360                 365

Val Met Asp Ser Ile Gly Asn Asn Cys Thr Met Asn Phe Gln Asn Asn
    370                 375                 380

Asn Gly Gly Asn Ile Gly Leu Leu Gly Phe His Ser Asn Asn Leu Val
385                 390                 395                 400

Ala Ser Ser Trp Tyr Tyr Asn Asn Ile Arg Lys Asn Thr Ser Ser Asn
            405                 410                 415

Gly Cys Phe Trp Ser Phe Ile Ser Lys Glu His Gly Trp Gln Glu Asn
            420                 425                 430
```